US006210950B1

(12) United States Patent
Johnson et al.

(10) Patent No.: US 6,210,950 B1
(45) Date of Patent: Apr. 3, 2001

(54) METHODS FOR DIAGNOSING, PREVENTING, AND TREATING DEVELOPMENTAL DISORDERS DUE TO A COMBINATION OF GENETIC AND ENVIRONMENTAL FACTORS

(75) Inventors: William G. Johnson, Short Hills; Edward Scott Stenroos, Harrison, both of NJ (US)

(73) Assignee: University of Medicine and Dentistry of New Jersey, New Brunswick, NJ (US)

(*) Notice: Subject to any disclaimer, the term of this patent is extended or adjusted under 35 U.S.C. 154(b) by 0 days.

(21) Appl. No.: 09/318,448

(22) Filed: May 25, 1999

(51) Int. Cl.[7] .......................... C07H 21/04; C07H 21/02; C12N 1/20; C12N 15/00; C12N 9/00

(52) U.S. Cl. .................. 435/252.3; 536/23.1; 536/24.31; 536/24.33; 435/183; 435/252.3; 435/320.1

(58) Field of Search ............................. 435/6, 91.1, 91.2, 435/183, 252.3, 320.1; 536/23.1, 23.5, 24.31, 24.33

(56) References Cited

PUBLICATIONS

Stratagene Cloning Systems Catalog, 1993, p. 94.*
Arinami, et al, Am J of Med. Genetics, 74: 526–28, (1997).
Joober et al., Mol Psychiatry, 5(3): 323–26, (2000).
Allen LH, Am J Clin Nutr Nov. 1995;62(5):1013–9.
Anderson JL, J Am Coll Cardiol Nov. 1, 1997;30(5):1206–11.
Andreasen NC, Science Oct. 14, 1994;266(5183):294–8.
Baird DD, Hum Reprod Dec. 1997;12(12):2607–13.
Baron M, Acta Psychiatr Scand Aug. 1995;92(2):81–6.
Bassett AS, Br J Psychiatry Sep. 1992;161:323–34.
Bates CJ, Eur J Clin Nutr Sep. 1994;48(9):660–8.
Benjamin J. Gershon ES, Biol Psychiatry Sep. 1, 1996;40(5):313–6.
Bogerts B, Arch Gen Psychiatry Aug. 1985;42(8):784–91.
Boyd JH, Schizophr Bull 1986;12(2):173–86.
Brixey SN, J Clin Psychol May 1993;49(3):447–56.
Carmel R, Arch Intern Med Nov. 1987;147(11):1995–6.
Carpenter WT Jr, Buchanan RW, N Engl J Med Mar. 10, 1994;330(10):681–90.
Chatkupt S, Am J Med Genet Nov. 1, 1992;44(4):508–12.
Chen MJ, J Biol Chem Mar. 25, 1984;259(6):3933–43.
Cooper BA, Rosenblatt DS, Annu Rev Nutr 1987;7:291–320.
Detera–Wadleigh SD, Nucleic Acids Res Aug. 11, 1989;17(15):6432.
Dohrenwend BP, Science Feb. 21, 1992;255(5047):946–52.
Duff EM, Cooper ES, Am J Public Health Mar. 1994;84(3):473–6.
Eaton WW, Schizophr Res Mar. 1992;6(3):181–92.
Falk CT, Rubinstein P, Ann Hum Genet Jul. 1987;51 (Pt 3):227–33.
Feder JN, Nucleic Acids Res Jul. 24, 1987;15(14):5906.
Fermo I, Ann Intern Med Nov. 15, 1995;123(10):747–53.
Freeman JM, N Engl J Med Mar. 6, 1975;292(10):491–6.
Gadowsky SL, J Adolesc Health Jun. 1995;16(6):465–74.
Gilliam TC, Genomics Nov. 1989;5(4):940–4.
Godfrey PS, Lancet Aug. 18, 1990;336(8712):392–5.
Gordon N, Brain Dev. Sep.–Oct. 1995;17(5):307–11.
Gottesman II, Clin Genet Jul. 1994;46(1 Spec No):116–23.
Grant SF, Nat Genet Oct. 1996;14(2):203–5.
Green MF, Psychiatry Res Aug. 1994;53(2):119–27.
Guaraldi GP, Ann Clin Psychiatry Jun. 1993;5(2):101–5.
Heutink P, Am J Hum Genet Aug. 1995;57(2):465–73.
Hitzig WH, Ciba Found Symp 1978;(68):77–91.
Horie N, Cell Struct Funct Jun. 1995;20(3):191–7.
Hornsby PP, Epidemiology Mar. 1998;9(2):193–8.
Jeste DV, Br J Psychiatry Oct. 1988;153:444–59.
Kendell RE, Kemp IW, Arch Gen Psychiatry Oct. 1989;46(10):878–82.
Kendell RE, Adams W, Br J Psychiatry Jun. 1991;158:758–63.
Kirch DG, Schizophr Bull 1993;19(2):355–70.
Kirke PN, Q J Med Nov. 1993;86(11):703–8.
Kovelman JA, Scheibel AB, Biol Psychiatry Dec. 1984;19(12):1601–21.
Lewis BA, Behav Genet May 1993;23(3):291–7.
Li N, Biochim Biophys Acta Oct. 18, 1994;1219(2):515–20.
Lombroso PJ, J Am Acad Child Adolesc Psychiatry Sep. 1994;33(7):921–38.
Louis–Ferdinand RT, Adverse Drug React Toxicol Rev Winter 1994;13(4):193–206.
McPartlin J, Lancet Jan. 16, 1993;341(8838):148–9.
Mednick SA, Arch Gen Psychiatry Feb. 1988;45(2):189–92.
Metz J, Am J Hematol Apr. 1995;48(4):251–5.
Molloy AM, Lancet May 31, 1997;349(9065):1591–3.
Morita H, Circulation Apr. 15, 1997;95(8):2032–6.
Naurath HJ, Lancet Jul. 8, 1995;346(8967):85–9.
O'Callaghan E, Br J Psychiatry Jun. 1991;158:764–9.
Owen MJ, Psychol Med May 1992;22(2):289–93.
Pauls DL, Adv Neurol 1992;58:151–7.
Pyper CM■ Eur J Contracept Reprod Health Care Jun. 1997;2(2):131–46.

(List continued on next page.)

*Primary Examiner*—Bradley L. Sisson
(74) *Attorney, Agent, or Firm*—Klauber & Jackson

(57) ABSTRACT

The present invention discloses a novel method for identifying an individual who may be susceptible to develop a developmental disorder. In one particular example, an individual is identified who is genetically susceptible to becoming schizophrenic. In addition, the present invention discloses a novel method for identifying individuals who are genetically susceptible to have offspring with a developmental disorder. Methods of diagnosing, preventing and treating developmental disorders such as schizophrenia are also provided.

23 Claims, 5 Drawing Sheets

OTHER PUBLICATIONS

Regland B, J Neural Transm Gen Sect 1994;98(2):143–52.
Reynolds EH, Lancet Jul. 28, 1984;2(8396):196–8.
Sanders TA, Reddy S, Am J Clin Nutr May 1994;59(5 Suppl):1176S–1181S.
Scholl TO, Am J Clin Nutr Apr. 1996;63(4):520–5.
Schorah CJ, Wild J, Lancet May 29, 1993;341(8857):1417.
Shapiro RM, Schizophr Res Oct. 1993;10(3):187–239.
Shen F, Biochemistry Feb. 8, 1994;33(5):1209–15.
Sherrington R, Nature Nov. 10, 1988;336(6195):164–7.
Shevell MI, Rosenblatt DS, Can J Neurol Sci Nov. 1992;19(4):472–86.
Spielman RS, Am J Hum Genet Mar. 1993;52(3):506–16.
Susser E, Arch Gen Psychiatry Jan. 1996;53(1):25–31.
Susser ES, Lin SP, Arch Gen Psychiatry Dec. 1992;49(12):983–8.
Terwilliger JD, Ott J, Hum Hered 1992;42(6):337–46.
Torrey EF, Bowler A, Schizophr Bull 1990;16(4):591–604.
Torrey EF, Schizophr Bull 1993;19(3):557–62.
Trakatellis A, Postgrad Med J Oct. 1997;73(864):617–22.
van der Put NM, Lancet Oct. 21, 1995;346(8982):1070–1.
Weiffenbach B, Genomics May 1991;10(1):173–85.
Weinberg CR, Wilcox AJ, Lie RT■ Am J Hum Genet Apr. 1998;62(4):969–78.
Weinberger DR, Arch Gen Psychiatry Jul. 1987;44(7):660–9.
Whitehead AS, QJM Nov. 1995;88(11):763–6.
Wilcox AJ, Am J Epidemiol Nov. 1, 1998;148(9):893–901.
Wilcox AJ, Hum Reprod Feb. 1998;13(2):394–7.
Wouters MG, Fertil Steril Nov. 1993;60(5):820–5.
Yang JK, J Mol Biol Jun. 25, 1984;176(2):169–87.

* cited by examiner

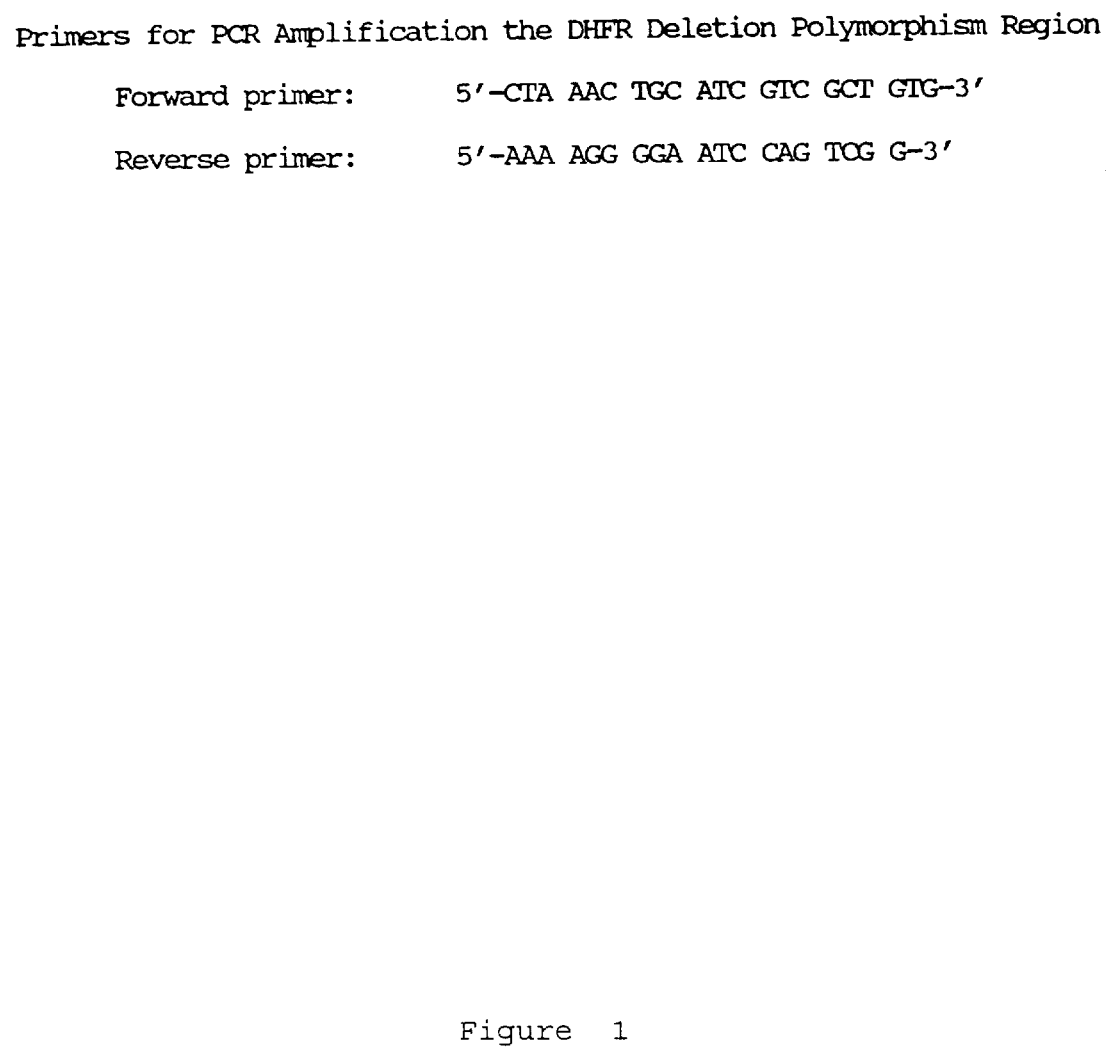

Primers for PCR Amplification the DHFR Deletion Polymorphism Region

Forward primer: 5′-CTA AAC TGC ATC GTC GCT GTG-3′

Reverse primer: 5′-AAA AGG GGA ATC CAG TCG G-3′

Figure 1

Genotypes of the DHFR 19 bp Deletion
by Non-denaturing Polyacrylamide Gel Electrophoresis Sequences of PCR Amplification Products
in the Region of the DHFR Deletion Polymorphism Region

```
                                             *
Allele 1   GCTGCCCACGGTCGGGGTACCTGGGCGGGACGCGCCAGGCCGACTCCCGGCGAGA
           ||||||||||||||||||                   ||||||||||||||||||
Allele 2   GCTGCCCACGGTCGGGGT...................GGCCGACTCCCGGCGAGA
```

Figure 3

1 CTGCAGCGCC AGGGTCCACC TGGTCGGCTG CACCTGTGGA GGAGGAGGTG
51 GATTTCAGGC TTCCCGTAGA CTGGAAGAAT CGGCTCAAAA CCGCTTGCCT
101 CGCAGGGGCT GAGCTGGAGG CAGCGAGGCC GCCCGACGCA GGCTTCCGGC
151 GAGACATGGC AGGGCAAGGA TGGCAGCCCG GCGGCAGGGC CCGGCGAGGA
201 GCGCGAACCC GCGGCCGCAG TTCCCAGGCG TCTGCGGGCG CGAGCACGCC
251 GCGACCCTGC GTGCGCCGGG GCGGGGGGGC GGGGCCTCGC CTGCACAAAT
301 AGGGACGAGG GGGCGGGGCG GCCACAATTT CGCGCCAAAC TTGACCGCGC
351 GTTCTGCTGT AACGAGCGGG CTCGGAGGTC CTCCCGCTGC TGTCATGGTT
401 GGTTCGCTAA ACTGCATCGT CGCTGTGTCC CAGAACATGG GCATCGGCAA
451 GAACGGGGAC CTGCCCTGGC CACCGCTCAG GTATCTGCCG GGCCGGGGCG
501 ATGGGACCCA AACGGGCGCA GGCTGCCCAC GGTCGGGGTA CCTGGGCGGG
551 ACGCGCCAGG CCGACTCCCG GCGAGAGGAT GGGGCCAGAC TTGCGGTCTG
601 CGCTGGCAGG AAGGGTGGGC CCGACTGGAT TCCCCTTTTC TGCTGCGCGG
651 GAGGCCCAGT TGCTGATTTC TGCCCGGATT CTGCTGCCCG GTGAGGTCTT
701 TGCCCTGCGG CGCCCTCGCC CAGGGCAAAG TCCCAGCCCT GGAGAAAACA
751 CCTCACCCCT ACCCACAGCG CTCCGTTTGT CAGGTGCCTT AGAGCTCGAG
801 CCCAAGGGAT AATGTTTCGA GTAACGCTGT TTCTCTAACT TGTAGGAATG
851 AATTCAGATA TTTCCAGAGA ATGACCACAA CCTCTTCAGT AGAAGGTAAT
901 GTGGGATTAA GTAGGGTCTT GCTTGATGAA GTTTACCAGT GCAAATGTTA
951 GTTAAATGGA AAGTTTTCCG TGTTAATCTG GGACCTTTTC TCTTATTATG
1001 GATCTGTATG ATCTGTATGC AGTTCCCAAG GTTCATTTAC CATTATTAAA
1051 AAATTTTTGT CTTAGAAATT TTATGTATGT CAACGCACGA GCAAATTATC
1101 AGGCATGGGG CAGAATTGGC AACTGGGTGG AGGCTTCGGT GGAGGTTAGC
1151 ACTCCGAAAG GAAAACAGAG TAGGCCTTTG GAACAGCTGC TGGAAGAGAT
1201 AAGGCCTGAA CAAGGGCAGT GGAGAAGAGA GGGTAAAAAT TTTTTAAGGT
1251 TACATGACCC TGGATTTTGG AGATC

Figure 4A

```
   1 CTGCAGCGCC AGGGTCCACC TGGTCGGCTG CACCTGTGGA GGAGGAGGTG
  51 GATTTCAGGC TTCCCGTAGA CTGGAAGAAT CGGCTCAAAA CCGCTTGCCT
 101 CGCAGGGGCT GAGCTGGAGG CAGCGAGGCC GCCCGACGCA GGCTTCCGGC
 151 GAGACATGGC AGGGCAAGGA TGGCAGCCCG GCGGCAGGGC CCGGCGAGGA
 201 GCGCGAACCC GCGGCCGCAG TTCCCAGGCG TCTGCGGGCG CGAGCACGCC
 251 GCGACCCTGC GTGCGCCGGG GCGGGGGGC GGGGCCTCGC CTGCACAAAT
 301 AGGGACGAGG GGGCGGGGCG GCCACAATTT CGCGCCAAAC TTGACCGCGC
 351 GTTCTGCTGT AACGAGCGGG CTCGGAGGTC CTCCCGCTGC TGTCATGGTT
 401 GGTTCGCTAA ACTGCATCGT CGCTGTGTCC CAGAACATGG GCATCGGCAA
 451 GAACGGGGAC CTGCCCTGGC CACCGCTCAG GTATCTGCCG GGCCGGGGCG
 501 ATGGGACCCA AACGGGCGCA GGCTGCCCAC GGTCGGGGT
 551         GG CCGACTCCCG GCGAGAGGAT GGGGCCAGAC TTGCGGTCTG
 601 CGCTGGCAGG AAGGGTGGGC CCGACTGGAT TCCCCTTTTC TGCTGCGCGG
 651 GAGGCCCAGT TGCTGATTTC TGCCCGGATT CTGCTGCCCG GTGAGGTCTT
 701 TGCCCTGCGG CGCCCTCGCC CAGGGCAAAG TCCCAGCCCT GGAGAAAACA
 751 CCTCACCCCT ACCCACAGCG CTCCGTTTGT CAGGTGCCTT AGAGCTCGAG
 801 CCCAAGGGAT AATGTTTCGA GTAACGCTGT TTCTCTAACT TGTAGGAATG
 851 AATTCAGATA TTTCCAGAGA ATGACCACAA CCTCTTCAGT AGAAGGTAAT
 901 GTGGGATTAA GTAGGGTCTT GCTTGATGAA GTTTACCAGT GCAAATGTTA
 951 GTTAAATGGA AAGTTTTCCG TGTTAATCTG GGACCTTTTC TCTTATTATG
1001 GATCTGTATG ATCTGTATGC AGTTCCCAAG GTTCATTTAC CATTATTAAA
1051 AAATTTTTGT CTTAGAAATT TTATGTATGT CAACGCACGA GCAAATTATC
1101 AGGCATGGGG CAGAATTGGC AACTGGGTGG AGGCTTCGGT GGAGGTTAGC
1151 ACTCCGAAAG GAAAACAGAG TAGGCCTTTG GAACAGCTGC TGGAAGAGAT
1201 AAGGCCTGAA CAAGGGCAGT GGAGAAGAGA GGGTAAAAAT TTTTTAAGGT
1251 TACATGACCC TGGATTTTGG AGATC
```

Figure 4B

SEQUENCE LISTING

```
<160> NUMBER OF SEQ ID NOS: 46

<210> SEQ ID NO 1
<211> LENGTH: 2187
<212> TYPE: DNA
<213> ORGANISM: Homo sapiens

<400> SEQUENCE: 1

gccatggtga acgaagccag aggaaacagc agcctcaacc cctgcttgga gggcagtgcc     60

agcagtggca gtgagagctc caaagatagt tcgagatgtt ccacccccggg cctggaccct   120

gagcggcatg agagactccg ggagaagatg aggcggcgat tggaatctgg tgacaagtgg    180

ttctccctgg aattcttccc tcctcgaact gctgagggag ctgtcaatct catctcaagg    240

tttgaccgga tggcagcagg tggcccccctc tacatagacg tgacctggca cccagcaggt   300

gaccctggct cagacaagga gacctcctcc atgatgatcg ccagcaccgc cgtgaactac    360

tgtggcctgg agaccatcct gcacatgacc tgctgccgtc agcgcctgga ggagatcacg    420

ggccatctgc acaaagctaa gcagctgggc ctgaagaaca tcatggcgct gcggggagac    480

ccaataggtg accagtggga agaggaggag ggaggcttca actacgcagt ggacctggtg    540

aagcacatcc gaagtgagtt tggtgactac tttgacatct gtgtggcagg ttaccccaaa    600

ggccaccccg aagcagggag ctttgaggct gacctgaagc acttgaagga gaaggtgtct    660

gcgggagccg atttcatcat cacgcagctt ttctttgagg ctgacacatt cttccgcttt    720

gtgaaggcat gcaccgacat gggcatcact tgccccatcg tccccgggat ctttcccatc    780

cagggctacc actcccttcg gcagcttgtg aagctgtcca agctggaggt gccacaggag    840

atcaaggacg tgattgagcc aatcaaagac aacgatgctg ccatccgcaa ctatggcatc    900

gagctggccg tgagcctgtg ccaggagctt ctggccagtg gcttggtgcc aggcctccac    960

ttctacaccc tcaaccgcga gatggctacc acagaggtgc tgaagcgcct ggggatgtgg   1020

actgaggacc ccaggcgtcc cctaccctgg gctctcagtg cccaccccaa gcgccgagag   1080

gaagatgtac gtcccatctt ctgggcctcc agaccaaaga gttacatcta ccgtacccag   1140

gagtgggacg agttccctaa cggccgctgg ggcaattcct cttcccctgc ctttggggag   1200

ctgaaggact actacctctt ctacctgaag agcaagtccc ccaaggagga gctgctgaag   1260

atgtgggggg aggagctgac cagtgaagca agtgtctttg aagtctttgt tctttacctc   1320

tcgggagaac caaaccggaa tggtcacaaa gtgacttgcc tgccctggaa cgatgagccc   1380

ctggcggctg agaccagcct gctgaaggag gagctgctgc gggtgaaccg ccagggcatc   1440

ctcaccatca actcacagcc caacatcaac gggaagccgt cctccgaccc catcgtgggc   1500

tggggcccca gcgggggcta tgtcttccag aaggcctact tagagttttt cacttcccgc   1560

gagacagcgg aagcacttct gcaagtgctg aagaagtacg agctccgggt taattaccac   1620
```

```
cttgtcaatg tgaagggtga aaacatcacc aatgcccctg aactgcagcc gaatgctgtc   1680

acttggggca tcttccctgg gcgagagatc atccagccca ccgtagtgga tcccgtcagc   1740

ttcatgttct ggaaggacga ggcctttgcc ctgtggattg agcggtgggg aaagctgtat   1800

gaggaggagt ccccgtcccg caccatcatc cagtacatcc acgacaacta cttcctggtc   1860

aacctggtgg acaatgactt cccactggac aactgcctct ggcaggtggt ggaagacaca   1920

ttggagcttc tcaacaggcc cacccagaat gcgagagaaa cggaggctcc atgaccctgc   1980

gtcctgacgc cctgcgttgg agccactcct gtcccgcctt cctcctccac agtgctgctt   2040

ctcttgggaa ctccactctc cttcgtgtct ctcccacccc ggcctccact cccccacctg   2100

acaatggcag ctagactgga gtgaggcttc caggctcttc ctggacctga gtcggcccca   2160

catgggaacc tagtactctc tgctcta                                        2187
```

<210> SEQ ID NO 2
<211> LENGTH: 7122
<212> TYPE: DNA
<213> ORGANISM: Homo sapiens

<400> SEQUENCE: 2

```
gcgcgtgtct ggctgctagg ccgacaccaa ggactggccg ggtacccggg aagaaagcac     60

gtgctccagc agttgccgcg cccagccccg agagaggccc tagggcgctg cgggctttcg    120

gggtccgcag tccccccgcg acgcgagcca acgggaggcg tcaaaagacc cgggccttgt    180

gtggcaggct cgcctggcgc tggctggcgt ggcccttggc cgtcgtcacc tgtggagagc    240

acgtcttctc tgccgcgccc tctgcgcaag gaggagactc gacaacatgt cacccgcgct    300

ccaagacctg tcgcaacccg aaggtctgaa gaaaaccctg cgggatgaga tcaatgccat    360

tctgcagaag aggattatgg tgctggatgg agggatgggg accatgatcc agcgggagaa    420

gctaaacgaa gaacacttcc gaggtcagga atttaaagat catgccaggc cgctgaaagg    480

caacaatgac attttaagta taactcagcc tgatgtcatt taccaaatcc ataaggaata    540

cttgctggct ggggcagata tcattgaaac aaatactttt agcagcacta gtattgccca    600

agctgactat ggccttgaac acttggccta ccggatgaac atgtgctctg caggagtggc    660

cagaaaagct gccgaggagg taactctcca gacaggaatt aagaggtttg tggcaggggc    720

tctgggtccg actaataaga cactctctgt gtccccatct gtggaaaggc cggattatag    780

gaacatcaca tttgatgagc ttgttgaagc ataccaagag caggccaaag gacttctgga    840

tggcggggtt gatatcttac tcattgaaac tatttttgat actgccaatg ccaaggcagc    900

cttgtttgca ctccaaaatc tttttgagga gaaatatgct ccccggccta tctttatttc    960

agggacgatc gttgataaaa gtgggcggac tctttccgga cagacaggag agggatttgt   1020

catcagcgtg tctcatggag aaccactcta cattggatta aattgtgctt tgggtgcagc   1080

tgaaatgaga ccttttattg aaataattgg aaaatgtaca acagcctatg tcctctgtta   1140

tcccaatgca ggtcttccca acacctttgg tgactatgat gaaacgcctt ctatgatggc   1200

caagcaccta aaggattttg ctatggatgg cttggtcaat atagttggag gatgctgtgg   1260

gtcaacacca gatcatatca gggaaattgc tgaagctgtg aaaaattgta agcctagagt   1320

tccacctgcc actgcttttg aaggacatat gttactgtct ggtctagagc ccttcaggat   1380

tggaccgtac accaactttg ttaacattgg agagcgctgt aatgttgcag gatcaaggaa   1440

gtttgctaaa ctcatcatgg caggaaacta tgaagaagcc ttgtgtgttg ccaaagtgca   1500

ggtggaaatg ggagcccagg tgttggatgt caacatggat gatggcatgc tagatggtcc   1560
```

```
aagtgcaatg accagatttt gcaacttaat tgcttccgag ccagacatcg caaaggtacc   1620
tttgtgcatc gactcctcca attttgctgt gattgaagct gggttaaagt gctgccaagg   1680
gaagtgcatt gtcaatagca ttagtctgaa ggaaggagag gacgacttct tggagaaggc   1740
caggaagatt aaaaagtatg gagctgctat ggtggtcatg gcttttgatg aagaaggaca   1800
ggcaacagaa acagacacaa aaatcagagt gtgcacccgg gcctaccatc tgcttgtgaa   1860
aaaactgggc tttaatccaa atgacattat ttttgaccct aatatcctaa ccattgggac   1920
tggaatggag gaacacaact tgtatgccat taattttatc catgcaacaa aagtcattaa   1980
agaaacatta cctggagcca gaataagtgg aggtctttcc aacttgtcct tctccttccg   2040
aggaatggaa gccattcgag aagcaatgca tggggttttc ctttaccatg caatcaagtc   2100
tggcatggac atggggatag tgaatgctgg aaacctccct gtgtatgatg atatccataa   2160
ggaacttctg cagctctgtg aagatctcat ctggaataaa gaccctgagg ccactgagaa   2220
gctcttacgt tatgcccaga ctcaaggcac aggagggaag aaagtcattc agactgatga   2280
gtggagaaat ggccctgtcg aagaacgcct tgagtatgcc cttgtgaagg gcattgaaaa   2340
acatattatt gaggatactg aggaagccag gttaaaccaa aaaaaatatc cccgacctct   2400
caatataatt gaaggacccc tgatgaatgg aatgaaaatt gttggtgatc tttttggagc   2460
tggaaaaatg tttctacctc aggttataaa gtcagcccgg gttatgaaga aggctgttgg   2520
ccaccttatc cctttcatgg aaaaagaaag agaagaaacc agagtgctta acggcacagt   2580
agaagaagag gacccttacc agggcaccat cgtgctggcc actgttaaag gcgacgtgca   2640
cgacataggc aagaacatag ttggagtagt ccttggctgc aataatttcc gagttattga   2700
tttaggagtc atgactccat gtgataagat actgaaagct gctcttgacc acaaagcaga   2760
tataattggc ctgtcaggac tcatcactcc ttccctggat gaaatgattt ttgttgccaa   2820
ggaaatggag agattagcta taaggattcc attgttgatt ggaggagcaa ccacttcaaa   2880
aacccacaca gcagttaaaa tagctccgag atacagtgca cctgtaatcc atgtcctgga   2940
cgcgtccaag agtgtggtgg tgtgttccca gctgttagat gaaaatctaa aggatgaata   3000
ctttgaggaa atcatggaag aatatgaaga tattagacag gaccattatg agtctctcaa   3060
ggagaggaga tacttaccct taagtcaagc cagaaaaagt ggtttccaaa tggattggct   3120
gtctgaacct cacccagtga agcccacgtt tattgggacc caggtctttg aagactatga   3180
cctgcagaag ctggtggact acattgactg gaagcctttc tttgatgtct ggcagctccg   3240
gggcaagtac ccgaatcgag gctttcccaa gatatttaac gacaaaacag taggtggaga   3300
ggccaggaag gtctacgatg atgcccacaa tatgctgaac acactgatta gtcaaaagaa   3360
actccgggcc cggggtgtgg ttgggttctg gccagcacag agtatccaag acgacattca   3420
cctgtacgca gaggctgctg tgccccaggc tgcagagccc atagccacct tctatgggtt   3480
aaggcaacag gctgagaagg actctgccag cacggagcca tactactgcc tctcagactt   3540
catcgctccc ttgcattctg gcatccgtga ctacctgggc ctgtttgccg ttgcctgctt   3600
tggggtagaa gagctgagca aggcctatga ggatgatggt gacgactaca gcagcatcat   3660
ggtcaaggcg ctgggggacc ggctggcaga ggcctttgca gaagagctcc atgaaagagt   3720
tcgccgagaa ctgtgggcct actgtggcag tgagcagctg gacgtcgcag acctgcgcag   3780
gctgcggtac aagggcatcc gcccggctcc tggctacccc agccagcccg accacaccga   3840
gaagctcacc atgtggagac tcgcagacat cgagcagtct acaggcatta ggttaacaga   3900
```

-continued

```
atcattagca atggcacctg cttcagcagt ctcaggcctc tacttctcca atttgaagtc   3960
caaatatttt gctgtgggga agatttccaa ggatcaggtt gaggattatg cattgaggaa   4020
gaacatatct gtggctgagg ttgagaaatg gcttggaccc attttgggat atgatacaga   4080
ctaacttttt tttttttgc ctttttttatt cttgatgatc ctcaaggaaa tacaacctag   4140
ggtgccttaa aaataacaac aacaaaaaac ctgtgtgcat ctggctgaca cttacctgct   4200
tctggttttc gaagactatt tagtggaacc ttgtagagga gcagggtctt cctgcagtgc   4260
ctggaaaaca ggcgctgttt ttttgggacc ttgcgtgaag agcagtgagc agggttcctg   4320
tggtttccct ggtccctctg agatggggac agactgaaga cagaggtcgt ttgatttcaa   4380
agcaagtcaa cctgcttttt tctgtttttta cagtggaatc taggaggcca cttagtcgtc   4440
tttttttcct cttagaagaa aagcctgaaa ctgagttgaa tagagaagtg tgaccctgtg   4500
acaaaatgat actgtgaaaa atggggcatt ttaatctaag tggttataac agtggattct   4560
gacggggaag gtgtagctct gttctcttcg gaagacctcg ttttctaaag gctggactaa   4620
atggctgcag aactcccttt ggcaaaaggc atgcgctcac tgcttgcttg tcagaaacac   4680
tgaagccatt tgccccagtg tggtcaagca gccatgcttt ctgggcattt tcgtcctccc   4740
ataatttcat atttccgtac ccctgaggaa acaaaaagga aatgaggaga gaaagttact   4800
gttaagggtg gttaacattt tttttgtttt gttttgtttt ggtttttttt ttttgagaca   4860
gagtctggct ctgtcgccca ggctggagtg caggggcgca atctcggctc atagcaagct   4920
ccgcctcctg ggttcatgcc attctcctgc ctcagcctcc agagtagctg ggactacagg   4980
tgcccaccac cacacccggc taattttttg tgtttttaca aaatacaaaa aagtagagac   5040
aggatttcac tgtgttagcc aggatggtct tgatctcccg acctcgtgat ctgcccacct   5100
cagcctccca aaatgctggg attacaggcg tgagccaccg agcctggccg gttaacatct   5160
tttaattgtt tccaggattg agcaggttct cagctgggct ctgatatccc gtgcggagtt   5220
ggacaagtgg gcagcataaa gtcactcatt tcttaccatt ttattcccct caattctcaa   5280
tatattcagt aatgaagaat ggtgccacca ctcaagcaac aagcctcaaa ctcaaccatg   5340
tcatcttttt cttggatgat tgcagttatt tcaaaaattt gcatgcaaaa tatacactca   5400
tcctacttca agatggtggt ggcaatagtc aggagaaggt aacattggag tcctggtttg   5460
attcgaagga tgaagacgaa gaagcaaggg aggaacaaat gaagaaccat ctttgttcat   5520
gaataggaat attcaagatt ataaaggtat caggtctcct aaaattgatc tatggattta   5580
ataccatttt caatggaaat tccaacagat tttattgaat gaaacaagca ggtgtttata   5640
tggagtagca aaggacttaa aattaccaaa tgcttctaaa tatgaaggag aggttgggga   5700
cacgcaccct atgtgatacc aagttttatt gtcaagacag tgtcatggtg cagaggtagg   5760
cattctgagc aggggaacaa aataagggcc tagaaactca cccgtgcata tgttgacctt   5820
tgcaaaatga cctggtgaca tggcaagtca gtggggacag gaaggaccac tccctaagta   5880
atcccagaac aatggctatt catgtgggaa aaaaagaaat tttactttct ctcaccttac   5940
ctggtgataa gttccaaata tgttaagggc tttaatacaa aaagcaaaaa ttgtcagtgt   6000
ttggatgaaa aaagccttag ggcaggaaag aatctcttga gacataaagt agtaatcata   6060
aaggacaaga tggttaagtc aattctgtta aaactcaagg cttatattaa gcaaacactt   6120
gaagtgagaa gatgatccac aacttgagaa gacatttata atacaaataa ctgatgaagg   6180
attcataatc acaaatatag agaattccta tttaaaaaaa tagaaaaata gtgaagacta   6240
cacaagagga aatagggctt ttaaataaat agatgttctg tagcattggt cagggaaata   6300
```

-continued

```
tgaattagga ccacaatgag attccatttt atatccataa gatttgcaaa ggttgggtct   6360

gacagtacca gttgttagat ctgtagggac ttgtacaaca ttgtggatgt gtaaacaggc   6420

accactgctt taaaaaacaa ttatccctta cagacttgaa catttgcaga cgttatgatc   6480

ttgcttccaa ctcccacctg tatgtccagc aaactcttgc atgtggccac taggaggaat   6540

gtgtaagaat gttcatagtt acatatttat aatagttaat aactggaaaa agtgaaatgt   6600

atgtctgtct acaggaaaat aggtgaataa ttagatatat atattcattc tacgggatat   6660

tattcagtag tggaaatgag tgaactacag ctatacctca caataagaat gaatctcaga   6720

aaatattaag gaaaaaagca agtttgaaga gaccacatgg ggcgtactat ttttattggg   6780

cccaaaaaca agcaaaacca aagaatatgt agtctaagca tacgtataca ataaaactat   6840

gctattaaaa aaaaaaggta actgataaac caaaattgag catagtaatt acccacagaa   6900

ggaggaagtg gaagggacag gagcacatag gtagatgcca agttatgcag ctgttctggt   6960

tcctcctggt aggcttacaa gtgtttacta tatgctatta atacattata ctttataact   7020

aatagataac agttttttac atattaaata tgttctactt aaatatatta taaaaaataa   7080

aggcaaagtg gaatgtttaa aaaaaaaaaa aaaaaaaaaa aa                       7122
```

<210> SEQ ID NO 3
<211> LENGTH: 564
<212> TYPE: DNA
<213> ORGANISM: Homo sapiens

<400> SEQUENCE: 3

```
atggttggtt cgctaaactg catcgtcgct gtgtcccaga acatgggcat cggcaagaac     60

ggggacctgc cctggccacc gctcaggaat gaattcagat atttccagag aatgaccaca    120

acctcttcag tagaaggtaa acagaatctg gtgattatgg gtaagaagac ctggttctcc    180

attcctgaga agaatcgacc tttaaagggt agaattaatt tagttctcag cagagaactc    240

aaggaacctc cacaaggagc tcattttctt tccagaagtc tagatgatgc cttaaaactt    300

actgaacaac cagaattagc aaataaagta gacatggtct ggatagttgg tggcagttct    360

gtttataagg aagccatgaa tcacccaggc catcttaaac tatttgtgac aaggatcatg    420

caagactttg aaagtgacac gtttttttcca gaaattgatt tggagaaata taaacttctg    480

ccagaatacc caggtgttct ctctgatgtc caggaggaga aaggcattaa gtacaaattt    540

gaagtatatg agaagaatga ttaa                                           564
```

<210> SEQ ID NO 4
<211> LENGTH: 2158
<212> TYPE: DNA
<213> ORGANISM: Homo sapiens

<400> SEQUENCE: 4

```
gcgcggcata acgacccagg tcgcggcgcg gcggggcttg agcgcgtggc cggtgccgca     60

ggagccgagc atggagtacc aggatgccgt gcgcatgctc aataccctgc agaccaatgc    120

cggctacctg gagcaggtga agcgccagcg gggtgaccct cagacacagt tggaagccat    180

ggaactgtac ctggcacgga gtgggctgca ggtggaggac ttggaccggc tgaacatcat    240

ccacgtcact gggacgaagg ggaagggctc cacctgtgcc ttcacggaat gtatcctccg    300

aagctatggc ctgaagacgg gattctttag ctctccccac ctggtgcagg ttcgggagcg    360

gatccgcatc aatgggcagc ccatcagtcc tgagctcttc accaagtact tctggcgcct    420
```

-continued

```
ctaccaccgg ctggaggaga ccaaggatgg cagctgtgtc tccatgcccc cctacttccg    480
cttcctgaca ctcatggcct tccacgtctt cctccaagag aaggtggacc tggcagtggt    540
ggaggtgggc attggcgggg cttatgactg caccaacatc atcaggaagc ctgtggtgtg    600
cggagtctcc tctcttggca tcgaccacac cagcctcctg gggggatacgg tggagaagat    660
cgcatggcag aaagggggca tctttaagca aggtgtccct gccttcactg tgctccaacc    720
tgaaggtccc ctggcagtgc tgagggaccg agcccagcag atctcatgtc ctctatacct    780
gtgtccgatg ctggaggccc tcgaggaagg ggggccgccg ctgaccctgg gcctggaggg    840
ggagcaccag cggtccaacg ccgccttggc cttgcagctg gcccactgct ggctgcagcg    900
gcaggaccgc catggtgctg gggagccaaa ggcatccagg ccagggctcc tgtggcagct    960
gcccctggca cctgtgttcc agcccacatc ccacatgcgg ctcgggcttc ggaacacgga   1020
gtggccgggc cggacgcagg tgctgcggcg cgggcccctc acctggtacc tggacggtgc   1080
gcacaccgcc agcagcgcgc aggcctgcgt gcgctggttc cgccaggcgc tgcagggccg   1140
cgagaggccg agcggtggcc ccgaggttcg agtcttgctc ttcaatgcta ccggggaccg   1200
ggacccggcg gccctgctga agctgctgca gccctgccag tttgactatg ccgtcttctg   1260
ccctaacctg acagaggtgt catccacagg caacgcagac caacagaact tcacagtgac   1320
actggaccag gtcctgctcc gctgcctgga acaccagcag cactggaacc acctggacga   1380
agagcaggcc agcccggacc tctggagtgc ccccagccca gagcccggtg ggtccgcatc   1440
cctgcttctg gcgccccacc caccccacac ctgcagtgcc agctccctcg tcttcagctg   1500
catttcacat gccttgcaat ggatcagcca aggccgagac cccatcttcc agccacctag   1560
tcccccaaag ggcctcctca cccaccctgt ggctcacagt ggggccagca tactccgtga   1620
ggctgctgcc atccatgtgc tagtcactgg cagcctgcac ctggtgggtg gtgtcctgaa   1680
gctgctggag cccgcactgt cccagtagcc aaggcccggg gttggaggtg ggagcttccc   1740
acacctgcct gcgttctccc catgaactta catactaggt gccttttgtt tttggctttc   1800
ctggttctgt ctagactggc ctaggggcca gggctttggg atgggaggcc gggagaggat   1860
gtctttttta aggctctgtg ccttggtctc tccttcctct tggctgagat agcagagggg   1920
ctccccgggt ctctcactgt tgcagtggcc tggccgttca gcctgtctcc cccaacaccc   1980
cgcctgcctc ctggctcagg cccagcttat tgtgtgcgct gcctggccag gccctgggtc   2040
ttgccatgtg ctgggtggta gatttcctcc tcccagtgcc ttctgggaag ggagagggcc   2100
tctgcctggg acactgcggg acagagggtg gctggagtga attaaagcct ttgttttt    2158
```

<210> SEQ ID NO 5
<211> LENGTH: 7720
<212> TYPE: DNA
<213> ORGANISM: Homo sapiens

<400> SEQUENCE: 5

```
taagttgaca cttctcaggt tgtcacaaga ttcaggtatg gctcactgtt gcaggacata     60
agctgggatc tcctgggaat tggtctgctt gcaggcccta gagagccttc cttcttggtt    120
gattttcctc tagagatcca actgtcttct caggctcccc tgcctgcctc ctccttgggt    180
cctttcttgt ggcattgcca gattactggg cccccatttt ccctacactt actgccactc    240
atagtctgat ggttcccaca tctgcatcca acctggactc ttcccctgag ctttcccctc    300
tacaaccacc ttccccgggc caagggcaca caggcacctc gacaaaacag tgttctatgt    360
ttcttcctgc ccaaacctgc cctccctct ccctttttccc atctgtggta ccaccatggg    420
```

-continued

```
ctcagagaat aaaaaaaatg aaggcttctg tcattgactg gggtggagat ggagggaaga    480
gttagcccag aatcacaggt gctgtagaaa ggatacctga gttgccggga gagggggtcc    540
atgagttggg gatggaagga gagcttggcc cttcaaacaa ttgaagatct gatcaaaaga    600
ttcagaacat ctgtgatttt gtggctggtg atgggtgaca cctgggctaa tggggttggg    660
ggagttggtg gctctacaat ttatggcctt gggagatcct tgctctctat agctgactgg    720
gaggttggaa gcctgggctc tagcccttgc cttgatcctc cggatctcat tttcctcatc    780
tgcctaacag gacagagggg ttggaaactg atgagattag ctcaaaggat cctggcagct    840
caggctgcaa gattttttc agacctcagt gtttgggaaa aaattgggta ggtggagctt    900
agggactggc cttaggcctg cactgttaat tcacccctc ccactacccc atggaggcct    960
ggctggtgct cacatacaat aattaactgc tgagtggcct tcgcccaatc ccaggctcca   1020
ctcctgggct ccattcccac tccctgcctg tctcctaggc cactaaacca cagctgtccc   1080
ctggaataag gcaaggggga gtgtagagca gagcagaagc ctgagccaga cggagagcca   1140
cctcctctcc caggtatgtg acactcccca tccccttca gaggccacac accctatggc   1200
attcccacca tgtgttaagg attttctgaa ctggaagggc cctctgtttg cctgaaggcc   1260
agagaatctt gaagtggaga ctgaggccca gaccagagtg tggcctgctc aagattaaac   1320
gacaagttag tgttcatccc cctgaactag tacctgggct ctagcccttc agtccagagc   1380
tgagttctca gctcttctag tctggggccc caaggttggg tgtgggggtc atgattgttg   1440
gtggggaggg gtcacagctg gactaagacc tgaaggtgag actaggcagg tgggaaagga   1500
gcttgcagag tgatgctgct caaaaggaca ggaagagagc ctggcttcag aagcagccac   1560
agcaagagag actactgact gaacaggtgg gctccactgg gggctccgga aaggattttc   1620
tcagcccccca tccccagcac tgtgtgttgg ccgcacccat gagagcctca gcactctgaa   1680
ggtgcagggg gcaaaggcca aaagagctct ggcctgaact tgggtggtcc ctactgtgtg   1740
acttggggca tggccctcat ctgtgctgaa atgattccac aaagattaaa ctggctatca   1800
tttgttgatt tccccttct tacatttaat ccttgcagga gaaagctaag cctcaagata   1860
gtttgcttct ctttcccccca aggccaagga gaaggtggag tgagggctgg ggtcgggaca   1920
ggttgaacgg gaaccctgtg ctctaaacag ttagggtttg ttcccgcagg aactgaaccc   1980
aaaggatcac ctggtattcc ctgagagtac agatttctcc ggcgtggccc tcaaggttag   2040
tgagtgagca ggtccacagg ggcatgattg gatcctggaa tgaatgaatc aaccatgaga   2100
gagtgaatga acactggaat caatagagta gcagagtaat ggattgtgga gcaggaaaga   2160
gagctgctgg gtgggaattc aattccaggc ttatatgagc cctgctgtgc agtcggcctg   2220
gagacagccc agctcaggcc ctgcctagac ccctgtcaag gaggccctgt caagaggaga   2280
ggaggggcag cacgggggca aggcaagctt gtgagcggga aaggcatgtc cactttagcg   2340
actggtatgt ggaagatgag ttagaggaga cagatggaga gaagtcatag gaaataaatt   2400
ctgagcattt taggagggcc cagacacctg gtgtccagtg gagtgaagga aacagtcgcc   2460
tcccaaaatt cagtgtctga ggtcaaagga ttgaagttct gtgatgacca aggagaagcc   2520
agctctgtgg taggggggcac aggagctccc caaggcccca gggctgtcca gctggctgtc   2580
ccctgccagc acccatgtcc tgtgacccca ccccaccaag atcccatggt ttccgggaag   2640
ggcctactaa actagcttga gtgatgaggc tagaaagggg ctgggaccaa ggtttaaaaa   2700
gcaaaacaaa ctaacaaaaa ccacactgca gcccccccaa ctaaaacatt tttataaact   2760
```

-continued

```
tttttttttt ttttgagatg gagtctcgct ctgtcaccca ggctagagtg caatggcaca   2820
atcttggctc actgtaacct ccacctcctg gattcaagtg attctcctgc ctcagcctcc   2880
cacgtagctg ggactacagg cacacgacac cgcacccagc tcattttgta tttttagtag   2940
agacagggtt tcactatgtt ggccaggctg gtctcaaact tctgacctca ggtgatccac   3000
ccacctcagc cttccaaagt gctgggatta caggcatgag ccaccgcgcc cagcccattt   3060
ttgtaaactt ttacaatgaa gtaatttggt gtcaaaatct gacctgaaaa ttaatgtgag   3120
tttatgtata gttttaattt atcccactag tgtaactgtt tcaccccaga atatacactt   3180
gattattggg tatatgaaaa aaatattttc tttgaatcac ctttgatgaa atcctaaaaa   3240
attttaaccc tgaaacattt gaataaggca ttgtggacct atggcaaact cctggctatt   3300
tctgcatttt gcccaaatcc atccttgaat tatatcacct gaacctcgtg accacctgga   3360
gaaggcaatg aggctcaagc cagggagggg tggtgtctaa tcctaccttt cattggatct   3420
gggaaaactg agggagatgg gggcagggct ctatctgccc caggcttccg tccaggcccc   3480
accctcctgg agccctgcac acaacttaag gccccacctc cgcattcctt ggtgccactg   3540
accacagctc tttcttcagg gacagacatg gctcagcgga tgacaacaca gctgctgctc   3600
cttctagtgt gggtggctgt agtaggggag gctcagacaa ggattgcatg ggccaggact   3660
gagcttctca atgtctgcat gaacgccaag caccacaagg aaaagccagg ccccgaggac   3720
aagttgcatg agcaggtggg ccagggggtg atctggggtg gtgagggact ggctcaggaa   3780
gaggaaacga ggacatggaa atgccaaacc ccattggcac tggtgaactg aagtggagga   3840
gcccttcagt ttgcattaat atgggtgact tatttcagag acactgtgcc aaatgtcggt   3900
acaatgccaa cagttcacct tcttggttgt tgagtttccg cattacagaa ataaggaagc   3960
aggcccaaag gagagcctgg gaaatgaagt tggagtgacc catcctgggg ttgcttgatt   4020
tagggattta gactgggaat gactcctcca aagatctgag ggaagaaact gcacactgtg   4080
catagtggcc tcttttctgc cagccctaaa cagctcaaga agggagagtc tctcacatta   4140
tgaggctgtg tgcaaagcat tcttttttttt ttttcctgag acaaagtctc catatgttgc  4200
ccaggctggt ctcaaattcc tggactcaag tgatcctccc acctcagccc tcccaaagtg   4260
tgggattaca gaaatgagcc gtacgccctc ctgaagcatc ttggttcatg catctcgcaa   4320
aactttgggc tgtgtctctc gaccacattg gacctgaggt ctccctataa catttatttt   4380
gctaccaccc ctttaatatc ctgaacatga tgatataact aaagaaaaag cagaggaaaa   4440
gtaatttgta ggccaggtgt tacggctcac gcctgtaatc ccaacactgt gggatgtcga   4500
gatgggcaga tcacttgagc tcaggagttc gagaccagcc tggcaagat ggcaaaaccc   4560
catctctact aaaaaataaa aaaaattagt caggtgtggt ggcacatgcc tgcagtccca   4620
gctactcagg aggctgaggt gggcaggtca gttgagccca ggaggcagag attgtagatc   4680
gtgccactgc actccagcct gggcaacaga gtgagacctt gtcaaaagaa agaaagaacg   4740
aaaaaaagaa agaaaggaag gaaggaaggg gaggaaggaa agggagggag gaaagggagg   4800
gaggaaaggg agggaggcaa gggagagaaa cttgtaatac gcatttcttt ttttttttct   4860
tgagatagag ttttgctctt gttgcccagg gtggatggca gtggcacaat ctcagctcac   4920
tgcaacctcc acctcccagg ttcaagtgat tctcctgcct cagcctcctg agtaggcaca   4980
cgccaccaca cccagctaat tttttgtttg tttgtttgtt ttgtttgttg gtatttttag   5040
tagagatggg ggtttcacca tgttggccag gctggtctcg aactcctcac ctcataatcc   5100
gcccctcttg gcctcccaaa gtgctgagat tacaggtgtg agccactgcg cccggcctta   5160
```

-continued

```
agtgcacatt ttatttattt atttatttat ttatttattg agatggagtc ttgctctgtt   5220
gcccaggctg gagtgcagtg gcacaatctc agctcactgc aacctccacc tcccaggttc   5280
aagcaattct tctgccttgg cctccagagt agctgggact ataggcacct gccaccatgc   5340
ctagctaatt tttgtatttt tagtagaaat ggggttttgc catgttggcc aggctggtct   5400
ccattcttga ccttaagtga tctgtccacc tccacctccc aaagtgctgg gattacaggc   5460
actatgtgag ccactgtgcc ggcccacatt ttaatattta gcttgtcagc cttaagtaat   5520
gagattcagg aagcttgagg ataggcacac aggagcatag tttcaagttg tcctgaattt   5580
tgcagccatc acaagttagt ttttaaggaa aaagattagt tcctaagttg tttctcaata   5640
acttataata aaataacatc cacaattgat tggctataca ttgttttttt gtatcacaaa   5700
ttccacaaac agataatggg tgaggcagct agtcagggac aaaacacttc ccaagtagct   5760
gggattacag gtgtccgcca ccacacttgg ctagtttttt gtttgtttat tttttgagat   5820
ggagtcttgc tctgtcgccc aggctggagt gcagtggcat gatctcggct cactgcaagc   5880
tccacctgcc gggttcacac cattctcctg cctcagcctc ccaagtagct gggactacag   5940
gtgccagcca ccacgcccgg ctaatttttt gtatttttag tagagacggg gtttcaccat   6000
gttggccagg atggtcttga tctcttagcc tcgtgatcca cccgcctcgg cctcccaaaa   6060
tgctgggatt acaggcgtga gccaccgcac ccggcctaat ttttatattt ttagtagaga   6120
cggggtttca ccatgttggc caggctggtc tcaaactctt gatctcaggt gatccacctg   6180
ccttggcctc ccaaagtgct gggattacac aagtaagcca ctgcacccag cctggggtta   6240
caatttaaat tgcttttttta ccttcaaatc tttgacacct cagtgaggct taatctgacc   6300
gcactattac actacaagtc cccatccgtc tctgcttaat ttttgtccaa agcaaaaatc   6360
aggtgatgtg ttcattgttg taaccccagt ttctacaaaa gtacctgggt gagagtaagt   6420
aggatctcaa taaaggttga attaacaaat tttgtaatga ctgcaactcc agcaggagct   6480
cccttttggg ctcccactgt ctctgacggc cctctcccct aaagaggtcc caatagcaag   6540
tattttcctg ggtgacttcc agtgggctgg ggaatcaagg actaagaggg gagacactgc   6600
atgtggaata ttctggctgt gctggctgtg ctggctgtgg actgagtcct ctgtcttccc   6660
ccatccagtg tcgaccctgg aggaagaatg cctgctgttc taccaacacc agccaggaag   6720
cccataagga tgtttcctac ctatatagat tcaactggaa ccactgtgga gagatggcac   6780
ctgcctgcaa acggcatttc atccaggaca cctgcctcta cgagtgctcc cccaacttgg   6840
ggccctggat ccagcaggta tgcatggctt cctgcaggta caagacctag cggagcagct   6900
gagctttcca ggcatctctg caggctgcaa ccccagctcc agttctattc ggggctgagt   6960
tgctgggatt cttgaacctg agcccttctt ttgtatcaaa atcacccagg tggatcagag   7020
ctggcgcaaa gagcgggtac tgaacgtgcc cctgtgcaaa gaggactgtg agcaatggtg   7080
ggaagattgt cgcacctcct acacctgcaa gagcaactgg cacaagggct ggaactggac   7140
ttcaggtgag ggctggggtg ggcaggaatg gagggatttg gaagtggagg tgtgtgggtg   7200
tggaacaggt atgtgacaat ttggagttgt agggctggca gacctcaaga tagttccggg   7260
cccagtggct aaaggtcttc cctcctctct acagggttta acaagtgcgc agtgggagct   7320
gcctgccaac ctttccattt ctacttcccc acacccactg ttctgtgcaa tgaaatctgg   7380
actcactcct acaaggtcag caactacagc cgagggagtg gccgctgcat ccagatgtgg   7440
ttcgacccag cccagggcaa ccccaatgag gaggtggcga ggttctatgc tgcagccatg   7500
```

-continued

```
agtggggctg ggccctgggc agcctggcct ttcctgctta gcctggccct aatgctgctg   7560

tggctgctca gctgacctcc ttttaccttc tgatacctgg aaatccctgc cctgttcagc   7620

cccacagctc ccaactattt ggttcctgct ccatggtcgg gcctctgaca gccactttga   7680

ataaaccaga caccgcacat gtgtcttgag aattatttgg                         7720
```

<210> SEQ ID NO 6
<211> LENGTH: 255
<212> TYPE: PRT
<213> ORGANISM: Homo sapiens

<400> SEQUENCE: 6

```
Met Val Trp Lys Trp Met Pro Leu Leu Leu Leu Leu Val Cys Val Ala
  1               5                  10                  15

Thr Met Cys Ser Ala Gln Asp Arg Thr Asp Leu Leu Asn Val Cys Met
             20                  25                  30

Asp Ala Lys His His Lys Thr Lys Pro Gly Pro Glu Asp Lys Leu His
         35                  40                  45

Asp Gln Cys Ser Pro Trp Lys Lys Asn Ala Cys Cys Thr Ala Ser Thr
     50                  55                  60

Ser Gln Glu Leu His Lys Asp Thr Ser Arg Leu Tyr Asn Phe Asn Trp
 65                  70                  75                  80

Asp His Cys Gly Lys Met Glu Pro Ala Cys Lys Arg His Phe Ile Gln
                 85                  90                  95

Asp Thr Cys Leu Tyr Glu Cys Ser Pro Asn Leu Gly Pro Trp Ile Gln
            100                 105                 110

Gln Val Asn Gln Thr Trp Arg Lys Glu Arg Phe Leu Asp Val Pro Leu
        115                 120                 125

Cys Lys Glu Asp Cys Gln Arg Trp Trp Glu Asp Cys His Thr Ser His
    130                 135                 140

Thr Cys Lys Ser Asn Trp His Arg Gly Trp Asp Trp Thr Ser Gly Val
145                 150                 155                 160

Asn Lys Cys Pro Ala Gly Ala Leu Cys Arg Thr Phe Glu Ser Tyr Phe
                165                 170                 175

Pro Thr Pro Ala Ala Leu Cys Glu Gly Leu Trp Ser His Ser Tyr Lys
            180                 185                 190

Val Ser Asn Tyr Ser Arg Gly Ser Gly Arg Cys Ile Gln Met Trp Phe
        195                 200                 205

Asp Ser Ala Gln Gly Asn Pro Asn Glu Glu Val Ala Arg Phe Tyr Ala
    210                 215                 220

Ala Ala Met His Val Asn Ala Gly Glu Met Leu His Gly Thr Gly Gly
225                 230                 235                 240

Leu Leu Leu Ser Leu Ala Leu Met Leu Gln Leu Trp Leu Leu Gly
                245                 250                 255
```

<210> SEQ ID NO 7
<211> LENGTH: 817
<212> TYPE: DNA
<213> ORGANISM: Homo sapiens

<400> SEQUENCE: 7

```
cgcaggaata gatggacatg gcctggcaga tgatgcagct gctgcttctg gctttggtga     60

ctgctgcggg gagtgcccag cccaggagtg cgcgggccag gacggacctg ctcaatgtct    120

gcatgaacgc caagcaccac aagacacagc ccagccccga ggacgagctg tatggccagt    180

gcagtccctg gaagaagaat gcctgctgca cggccagcac cagccaggag ctgcacaagg    240
```

```
acacctcccg cctgtacaac tttaactggg atcactgtgg taagatggaa cccacctgca    300
agcgccactt tatccaggac agctgtctct gagtgctcac ccaacctggg gccctggatc    360
cggcaggtca accagagctg gcgcaaagag cgcattctga acgtgcccct gtgcaaagag    420
gactgtgagc gctggtggga ggactgtcgc acctcctaca cctgcaaaag caactggcac    480
aaaggctgga attggacctc agggattaat gagtgtccgg ccggggccct ctgcagcacc    540
tttgagtcct acttccccac tccagccgcc ctttgtgaag gcctctggag ccactccttc    600
aaggtcagca actatagtcg agggagcggc cgctgcatcc agatgtggtt tgactcagcc    660
cagggcaacc ccaatgagga ggtggccaag ttctatgctg cggccatgaa tgctggggcc    720
ccgtctcgtg ggattattga ttcctgatcc aagaagggtc ctctggggtt cttccaacaa    780
cctattctaa tagacaaatc cacatgaaaa aaaaaaa                             817
```

```
<210> SEQ ID NO 8
<211> LENGTH: 1669
<212> TYPE: DNA
<213> ORGANISM: Homo sapiens

<400> SEQUENCE: 8
```

```
gctaggcagc ttcgaaccag tgcaatgacg atgccagtca acggggccca caaggatgct     60
gacctgtggt cctcacatga caagatgctg gcacaacccc tcaaagacag tgatgttgag    120
gtttacaaca tcattaagaa ggagagtaac cggcagaggg ttggattgga gctgattgcc    180
tcggagaatt tcgccagccg agcagttttg gaggccctag gctcttgctt aaataacaaa    240
tactctgagg ggtacccggg ccagagatac tatggcggga ctgagtttat tgatgaactg    300
gagaccctct gtcagaagcg agccctgcag gcctataagc tggacccaca gtgctggggg    360
gtcaacgtcc agccctactc aggctcccct gcaaactttg ctgtgtacac tgccctggtg    420
gaaccccatg ggcgcatcat gggcctggac cttccggatg gggccacct gacccatggg    480
ttcatgacag acaagaagaa aatctctgcc acgtccatct tctttgaatc tatgccctac    540
aaggtgaacc cagatactgg ctacatcaac tatgaccagc tggaggagaa cgcacgcctc    600
ttccacccga agctgatcat cgcaggaacc agctgctact cccgaaacct ggaatatgcc    660
cggctacgga agattgcaga tgagaacggg gcgtatctca tggcggacat ggctcacatc    720
agcgggctgg tggcggctgg cgtggtgccc tccccatttg aacactgcca tgtggtgacc    780
accaccactc acaagaccct gcgaggctgc cgagctggca tgatcttcta caggaaagga    840
gtgaaaagtg tggatcccaa gactggcaaa gagattctgt acaacctgga gtctcttatc    900
aattctgctg tgttccctgg cctgcaggga ggtccccaca accacgccat tgctggggtt    960
gctgtggcac tgaagcaagc tatgactctg gaatttaaag tttatcaaca ccaggtggtg   1020
gccaactgca gggctctgtc tgaggccctg acggagctgg gctacaaaat agtcacaggt   1080
ggttctgaca accatttgat ccttgtggat ctccgttcca aaggcacaga tggtggaagg   1140
gctgagaagg tgctagaagc ctgttctatt gcctgcaaca agaacacctg tccaggtgac   1200
agaagcgctc tgcggcccag tggactgcgg ctggggaccc cagcactgac gtcccgtgga   1260
cttttggaaa aagacttcca aaaagtagcc cactttattc acagagggat agagctgacc   1320
ctgcagatcc agagcgacac tggtgtcaga gccaccctga aagagttcaa ggagagactg   1380
gcaggggata agtaccaggc ggccgtgcag gctctccggg aggaggttga gagcttcgcc   1440
tctctcttcc ctctgcctgg cctgcctgac ttctaaagga gcgggcccac tctggaccca   1500
```

-continued

```
cctggcgcca cagaggaagc tgcctgccgg agacccccac ctgagagatg gatgagctgc   1560

tccaaaggga actgttgaca ctcgggccct ttgagggggt ttcttttgga cttttttcat   1620

gttttcttca caaatcaaaa tttgtttaag tctcattgtt agtaattct               1669


<210> SEQ ID NO 9
<211> LENGTH: 3112
<212> TYPE: DNA
<213> ORGANISM: Homo sapiens

<400> SEQUENCE: 9

gtggaacctc gatattggtg gtgtccatcg tgggcagcgg actaataaag gccatggcgc     60

cagcagaaat cctgaacggg aaggagatct ccgcgcaaat aagggcgaga ctgaaaaatc    120

aagtcactca gttgaaggag caagtacctg gtttcacacc acgcctggca atattacagg    180

ttggcaacag agatgattcc aatctttata taaatgtgaa gctgaaggct gctgaagaga    240

ttgggatcaa agccactcac attaagttac caagaacaac cacagaatct gaggtgatga    300

agtacattac atctttgaat gaagactcta ctgtacatgg gttcttagtg cagctacctt    360

tagattcaga gaattccatt aacactgaag aagtgatcaa tgctattgca cccgagaagg    420

atgtggatgg attgactagc atcaatgctg ggagacttgc tagaggtgac ctcaatgact    480

gtttcattcc ttgtacgcct aagggatgct tggaactcat caaagagaca ggggtgccga    540

ttgccggaag gcatgctgtg gtggttgggc gcagtaaaat agttggggcc ccgatgcatg    600

acttgcttct gtggaacaat gccacagtga ccacctgcca ctccaagact gcccatctgg    660

atgaggaggt aaataaaggt gacatcctgg tggttgcaac tggtcagcct gaaatggtta    720

aggggagtgg gatcaaacct ggggcaatag tcatcgactg tggaatcaat tatgtcccag    780

atgataaaaa accaaatggg agaaaagttg tgggtgatgt ggcatacgac gaggccaaag    840

agagggcgag cttcatcact cctgttcctg gcggcgtagg gcccatgaca gttgcaatgc    900

tcatgcagag cacagtagag agtgccaagc gtttcctgga gaaatttaag ccaggaaagt    960

ggatgattca gtataacaac cttaacctca agacacctgt tccaagtgac attgatatat   1020

cacgatcttg taaaccgaag cccattggta agctggctcg agaaattggt ctgctgtctg   1080

aagaggtaga attatatggt gaaacaaagg ccaaagttct gctgtcagca ctagaacgcc   1140

tgaagcaccg gcctgatggg aaatacgtgg tggtgactgg aataactcca acacccctgg   1200

gagaagggaa aagcacaact acaatcggcc tagtgcaagc ccttggtgcc catctctacc   1260

agaatgtctt tgcgtgtgtg cgacagcctt ctcagggccc cacctttgga ataaaaggtg   1320

gcgctgcagg aggcggctac tcccaggtca ttcctatgga agagtttaat ctccacctca   1380

caggtgacat ccatgccatc actgcagcta ataacctcgt tgctgcggcc attgatgctc   1440

ggatatttca tgaactgacc cagacagaca aggctctctt taatcgtttg gtgccatcag   1500

taaatggagt gagaaggttc tctgacatcc aaatccgaag gttaaagaga ctaggcattg   1560

aaaagactga ccctaccaca ctgacagatg aagagataaa cagatttgca agattggaca   1620

ttgatccaga aaccataact tggcaaagag tgttggatac caatgataga ttcctgagga   1680

agatcacgat tggacaggct ccaacggaga agggtcacac acggacggcc cagtttgata   1740

tctctgtggc cagtgaaatt atggctgtcc tggctctcac cacttctcta gaagacatga   1800

gagagagact gggcaaaatg gtggtggcat ccagtaagaa aggagagccc gtcagtgccg   1860

aagatctggg ggtgagtggt gcactgacag tgcttatgaa ggacgcaatc aagcccaatc   1920

tcatgcagac actggagggc actccagtgt ttgtccatgc tggcccgttt gccaacatcg   1980
```

```
cacatggcaa ttcctccatc attgcagacc ggatcgcact caagcttgtt ggcccagaag   2040
ggtttgtagt gacggaagca ggatttggag cagacattgg aatggaaaag ttttttaaca   2100
tcaaatgccg gtattccggc ctctgccccc acgtggtggt gcttgttgcc actgtcaggg   2160
ctctcaagat gcacgggggc ggccccacgg tcactgctgg actgcctctt cccaaggctt   2220
acatacagga gaacctggag ctggttgaaa aaggcttcag taacttgaag aaacaaattg   2280
aaaatgccag aatgtttgga attccagtag tagtggccgt gaatgcattc aagacggata   2340
cagagtctga gctggacctc atcagccgcc tttccagaga acatggggct tttgatgccg   2400
tgaagtgcac tcactgggca gaagggggca agggtgcctt agccctggct caggccgtcc   2460
agagagcagc acaagcaccc agcagcttcc agctccttta tgacctcaag ctcccagttg   2520
aggataaaat caggatcatt gcacagaaga tctatggagc agatgacatt gaattacttc   2580
ccgaagctca acacaaagct gaagtctaca cgaagcaggg ctttgggaat ctccccatct   2640
gcatggctaa aacacacttg tctttgtctc acaacccaga gcaaaaaggt gtccctacag   2700
gcttcattct gcccattcgc gacatccgcg ccagcgttgg ggctggtttt ctgtacccct   2760
tagtaggaac gatgagcaca atgcctggac tccccacccg gccctgtttt tatgatattg   2820
atttggaccc tgaaacagaa caggtgaatg gattattcta aacagatcac catccatctt   2880
caagaagcta ctttgaaagt ctggccagtg tctattcagg cccactggga gttaggaagt   2940
ataagtaagc caagagaagt cagcccctgc ccagaagatc tgaaactaat agtaggagtt   3000
tccccagaag tcattttcag ccttaattct catcatgtat aaattaacat aaatcatgca   3060
tgtctgttta ctttagtgac gttccacaga ataaaaggaa acaagtttgc ca           3112
```

<210> SEQ ID NO 10
<211> LENGTH: 1792
<212> TYPE: DNA
<213> ORGANISM: Homo sapiens

<400> SEQUENCE: 10

```
cgcagcccag actcagactg gggaagcaaa caggggctgg acaggccagg agagcctgtc     60
ggacagtgat cctgagatgt gggagttgct gcagagggag aaggacaggc agtgtcgtgg    120
cctggagctc attgcctcag agaacttctg cagccgagct gcgctggagg ccctggggtc    180
ctgtctgaac aacaagtact cggagggtta tcctggcaag agatactatg gggagcaga     240
ggtggtggat gaaattgagc tgctgtgcca gcgccgggcc ttggaagcct ttgacctgga    300
tcctgcacag tggggagtca atgtccagcc ctactccggg tccccagcca acctggccgt    360
ctacacagcc cttctgcaac ctcacgaccg gatcatgggg ctggacctgc ccgatggggg    420
ccatctcacc cacggctaca tgtctgacgt caagcggata tcagccacgt ccatcttctt    480
cgagtctatg ccctataagc tcaaccccaa aactggcctc attgactaca accagctggc    540
actgactgct cgacttttcc ggccacggct catcatagct ggcaccagcg cctatgctcg    600
cctcattgac tacgcccgca tgagagaggt gtgtgatgaa gtcaaagcac acctgctggc    660
agacatggcc cacatcagtg gcctggtggc tgccaaggtg attccctcgc ctttcaagca    720
cgcggacatc gtcaccacca ctactcacaa gactcttcga ggggccaggt caggctcat     780
cttctaccgg aaaggggtga aggctgtgga ccccaagact ggccgggaga tcctttacac    840
atttgaggac cgaatcaact ttgccgtgtt cccatccctt caggggggcc cccacaatca    900
tgccattgct gcagtagctg tggccctaaa gcaggcctgc acccccatgt tccgggagta    960
```

-continued

```
ctccctgcag gttctgaaga atgctcgggc catggcagat gccctgctag agcgaggcta   1020

ctcactggta tcaggtggta ctgacaacca cctggtgctg gtggacctgc ggcccaaggg   1080

cctggatgga gctcgggctg agcgggtgct agagcttgta tccatcactg ccaacaagaa   1140

cacctgtcct ggagaccgaa gtgccatcac accgggcggc ctgcggcttg ggcccccagc   1200

cttaacttct cgacagttcc gtgaggatga cttccggaga gttgtggact ttatagatga   1260

aggggtcaac attggcttag aggtgaagag caagactgcc aagctccagg atttcaaatc   1320

cttcctgctt aaggactcag aaacaagtca gcgtctggcc aacctcaggc aacgggtgga   1380

gcagtttgcc agggccttcc ccatgcctgg ttttgatgag cattgaaggc acctgggaaa   1440

tgaggcccac agactcaaag ttactctcct tcccccctacc tgggccagtg aaatagaaag   1500

cctttctatt ttttggtgcg ggagggaaga cctctcactt agggcaagag ccaggtatag   1560

tctcccttcc cagaatttgt aactgagaag atcttttctt tttccttttt ttggtaacaa   1620

gacttagaag gagggcccag gcactttctg tttgaacccc tgtcatgatc acagtgtcag   1680

agacgcgtcc tctttcttgg ggaagttgag gagtgccctt cagagccagt agcaggcagg   1740

ggtgggtagg caccctcctt cctgttttta tctaataaaa tgctaacctg ca           1792
```

```
<210> SEQ ID NO 11
<211> LENGTH: 18596
<212> TYPE: DNA
<213> ORGANISM: Homo sapiens

<400> SEQUENCE: 11

cctgtagtcc cagctacgcg agaggctgag gcagcagaat tacttgaacc caggaggcgg     60

aggttgcagt gagccgagat cgcgccactg cactccagcc tgggtgagag agcgagactc    120

tgtctcaaaa aaaaaaaaaa aagaccgcca gggctcaaac aaaaaacctc ggaaaagccc    180

tggcggtctt tttttttttt tttttttttt ttttttggga cagtcttgct ctgtcgccca    240

ggctggagta caatggtcgg atcttggctc actgcaacct ctgcctccca ggttcaagca    300

attcttctgc ctcagcctcc caagtagcca ccacgcccag ctaatttttg tacttttagt    360

agagacgggg gtttcaccat gttgtccagg ctggtcttga actcctgacc tcaggtgatc    420

cacccgcctc ggccccccaa agtactagga ttacaggcgt gagccaccgc gtccagcgcc    480

ctggcggttt ttaatcaagt agaaaagctg cattatacca cttgcttcgg ttgcttcagt    540

gagaacgaag aaatggaaat gcaaatccct tattagttgt aggaaacaga tctcaaacag    600

cagttttgtt gacaagaccg caggaaaacg tgggaactgt gctgctggct tagagaaggc    660

gcggtcgacc agacggttcc caaagggcgc agtccttccc agccaccgca cctgcatcca    720

ggttcccggg tttcctaaga ctctcagctg tggccctggg ctccgttctg tgccacaccc    780

gtggctcctg cgtttccccc tggcgcacgc tctctagagc gggggccgcc gcgaccccgc    840

cgagcaggaa gaggcggagc gcgggacggc cgcgggaaaa ggcgcgcgga aggggtcctg    900

ccaccgcgcc acttggcctg cctccgtccc gccgcgccac ttggcctgcc tccgtcccgc    960

cgcgccactt cgcctgcctc cgtcccccgc ccgccgcgcc atgcctgtgg ccggctcgga   1020

gctgccgcgc cggcccttgc cccccgccgc acaggagcgg gacgccgagc cgcgtccgcc   1080

gcacggggag ctgcagtacc tggggcagat ccaacacatc ctccgctgcg gcgtcaggaa   1140

ggacgaccgc acgggcaccg gcaccctgtc ggtattcggc atgcaggcgc gctacagcct   1200

gagaggtgac gccgcgggcc cctgcgggac gggtggcggg aaggagggag gcgcggctgg   1260

ggagagcgct cgggagctgc cgggcgctgc ggaccccgtt tagtcctaac ctcaatcctg   1320
```

-continued

```
ccagggaggg gacgcatcgt cctcctcgcc ttacagacgc cgaaacggag ggtcccatta   1380

gggacgtgac tggcgcgggc aacacacaca gcagcgacag ccgggaggta agccgcgtcc   1440

cagcggctcc gcggccgggc tcgcagtcgc cccagtgatg ccgtggcccc cgaggcgggc   1500

gtcatcgggc agcgtttgcc cagtgctgga gggttaggga gagctgcctg ggcttgaccg   1560

cgcgccggtc tcaaagtcct ggctttggcc cctcctccgt tttcccctgt ggaccattcc   1620

gcttcgcagc gttttcaaaa actggagcga aagtgatgtg ggcggggcaa aggcggcggg   1680

aagaggacag cactgaagct ggcgcgggaa cttggtttcc tggtggcctc ccatccaatc   1740

cccacgaacc agctttcctc ttaaaccttg aaaagagaaa ttcgggagtt cgagttctta   1800

gtcgtccttt cctctttcct ttccgacagg agcaccccag gcaaaaaatg tctcgcgggt   1860

cattggcgcc aggctttcag ggacagtgg ggcggggcgg ggtgggcaca ggacgttagg   1920

cagccgttgg ccctccctaa ggccacaccg tcctgccgtc ctggatcctg cgccagctgc   1980

gcgggggagg ggactcgaag gtgtgtgagc caggggctga ccttgaccgc tcagataaat   2040

ggagcgcagc cttgacacag gggtggaggt ggttttgaat ggggaaaccc attcgtggtg   2100

aagcagattc actgtagcta gcggaaaagc cctccggccc acggacccat ctagagacga   2160

atacatagca gctgctgtgg ctgattggcg tgggacagcg tggggagttt tgtctgagga   2220

gagggatcca cttttctgca gctccaagcc caggggcctt tgatgagcca tagacctcat   2280

ttttaaccca cctttctgct tagacattga gcaagttact tctcatatag cttccctata   2340

tgttaaaaat ggagaaaata atgcttagta ggcaattctg ataaaagcag gtgcttgcaa   2400

aaatctctct gttgtctgaa tataaactgt accacaagcg agtgcggatg aacgaggact   2460

gcatttaaag ataagttttt acactttcat ttctctgtgg ctcgacactt ctgatgcctc   2520

ccttttttgtt cctgggacac atgcttggtg ttgtcttcac acctttgtga caggattagc   2580

actagtgggc agtggatgat agctcctcct cccttttgcc acatgttcat ccctgccctc   2640

gccaccatct cactgtgtgg aattcctgtg tccactggtc accggggcac agaagtgctg   2700

tctcagcctg aatcgggcca ctgatgggac ttgcagcctg ggagctccac cgtgatctct   2760

ggcccacttt gcgggagtct aggctttctg gatgctccag gcctcacgtc ccagggcagt   2820

tttcttccct gaagaaagtt ggatggcatg atctgtcttc ccatcttgaa accgtatggc   2880

aaattgtttt tcagatgaat tccctctgct gacaaccaaa cgtgtgttct ggaagggtgt   2940

tttggaggag ttgctgtggt ttatcaaggt aaagaagtcg ctgctattag aagtcagtag   3000

tctgttctca acacagcagc cagtgagatc ctttcaaaac tcaaagcagc caggtgtggt   3060

ggctcacgcc tgtaatccca ccgctttggg aggctgagtc agatcacctg aggttaggaa   3120

tttgggacca gcctggccaa catggcgaca ccccagtctc tactaataac acaaaaaatt   3180

agccaggtgt gctggtgcat gtctgtaatc ccagctactc aggaggctga ggcatgagaa   3240

ttgctcacga ggcggaggtt gtagtgagct gagatcgtgg cactgtactc cagcctggcg   3300

acagagggag aacccatgtc aaaaacaaaa aaagacacca ccaaaggtca aagcatatca   3360

ttcctcaccc tcaagccctt agtggctcca tttcactcag taagagccac ggtccttatg   3420

gtgtccgttt ttcagctctg accttagctg ctgctctctg caccaccctg ctgttcttgt   3480

gagtttttga gcacaccggg acatccccac tccctggaac cttcttcccc cacacttggc   3540

ttcttccttt gagtctctac tccactcggg caagccttcc tagacctcct gatttaaaac   3600

tgtgactctc ccccaacctc cttggtgttt ctccgtagac gaacatcacc atctgatgta   3660
```

-continued

```
tgtcagcctt tcccttcccc tgttagaagg gggacagcag gtagtaaaag tgaaatgtgc   3720
tgtaagcttt atgagggcag aggatttgtt tctcgtgttc actgttgtat cgccagggcc   3780
tcaaacacag cctgccacat agtaggagtc aacatatatt gatcactaaa tgtagatacc   3840
acctgtgttc ccatgttcat ataaattcta gaagagtctc ttcagtaaca aggtgaaccc   3900
cttccagagg gctgagtagg tacctcaggc cggggccaga gtgctgtgaa gacagcagca   3960
gcccagacca agcttctctg tgttccgtgt cctggtctag aaccagcgat gttctttctg   4020
accagtgctt tttggaaggt ggctgaggtc tgggctcagg tctgggccat actagaagct   4080
gggatccctt ctatagagca cttggtatgg cttgtatggt cttggggcaa gccagaccca   4140
agccctctta tcccatttta gaaagggctt caatttggat ccagccccag gtctgcctta   4200
gctctgtatt cttggggtat tttgttctgt attggcctat cttgactaac aatgagcctt   4260
ggatttgaaa catatcatca gaaacctcag aagacaacat tcttaaactg gctagagcct   4320
ggtctgaatg gatgaaaagg agagactttt gaagcaatat gtaaaagatt gagaaatgat   4380
ttgttggaaa tttctcaatt ggagaaattt ctttgatttg ttggaaattt ctttgattct   4440
ttctcaatca aagaaaatcg ggacaaactc aacaatagaa agggaggaag caagatactc   4500
agaaataaaa tgcattcccc tgtttcaact taatgcttca attcaggatt ctaaggaatc   4560
cttgccagga atgtcagact caccttgata gttggagtta ctccattggt gactcgatca   4620
aatacaggag ttgaggcacc tgcactgtaa aatactgatt agtctgatca ttaggaatat   4680
cctgtatgcc aggtagaaga tacattgaac agattgcatg taggcattaa attcattttg   4740
gggtattaca tatagacaac acatttcatt aagaaacata aaactgtcag atcggtggaa   4800
tacttaaaag cacttggagg tgtttagcct aaaaagctta gttgagggga atggaagaaa   4860
agatctggga gggtggttcc aaagaaggga tcagactatc ctaaagccct caggaatctg   4920
ggctgggacc acctacttaa agataggatg ggcagctggg tgtggtggct cacgcctgta   4980
atcccagcac ttcgggaggc cgaagcgggc ggatcacctg aggtcaggag ttcgaggcca   5040
gcctgaccaa catggagaaa cgctgtctct actaaaaata caaaattagc tgggtgtagt   5100
ggcgcatgcc tgtaatccca gctactcggg aggctgaggc aggggaatcg cttgaacctg   5160
ggaggtggag ggtgccgtga gccacgatcg cgccattgca ctccagcctg ggcaacaaga   5220
gcgaaactct caaaaaacaa aaaaaaggat gggttccata tgggtggtgt caagtgccca   5280
cctcctagca agtcagcagg ggccagaggc ccttgtaagt ggtgtctcgg ggggatcaac   5340
tgagatggct taagatttac ctggatgcct gctctgctct ccccatctct tccagggatc   5400
cacaaatgct aaagagctgt cttccaaggg agtgaaaatc tgggatgcca atggatcccg   5460
agactttttg gacagcctgg gattctccac cagagaagaa ggggacttgg gcccagttta   5520
tggcttccag tggaggcatt ttggggcaga atacagagat atggaatcag gtgaggagat   5580
agaacaatgc cttccatttc cgggtgccct tcctagcacg tgtttgctcc gttgttttag   5640
ataaggtctg ggggatgagt caatgtcaca ggagctgatg tatagctttg accttgtgag   5700
gggtggtgcc aggttgaagc cacaattaac gcctactgaa ggccgtttca catctttttt   5760
tttttttttt ttttaattat tatactttaa gttttagggt acatgtgcac aatgtgcagg   5820
ttagttacat atgtatacat gtgccatgct ggtgcgctgc accactaact caccatctag   5880
catcaggtat atctcccaat gctatccctc ccccctcctc ccaccccaca acatccccag   5940
agtgtgatgt tccccttcct gtgtccatat gttctcgttg ttcgattccc actatgagtg   6000
agaatatgcg gtgtttggtt ttttgttctt gcgatagttt actgagaatg atgatttcca   6060
```

-continued

```
tttcaccacg tccctacaga ggacatgaac tcatcatttt ttatggctgc atagtattcc   6120
atggtgtata tgtgccacat tttcttaatc cagtctatca tgttggacat ttgggttggt   6180
tccaagtctt tgcctattgt gaatagtgcc acaataaaca tacgtgtgca tgtgtcttta   6240
tagcagcatg atttaatagt cctttgggta tatacccagt aatgggatgg ctgggtcaaa   6300
tggtatttct agttctagat ccccgaggaa tcgccacact gacttccaca atggttgaac   6360
tagtttacag tcccaccaac agtgtcaaag tgtcctattt ctccacatcc tctccagcac   6420
ctgttgtttc ctgacttttt aatgattgcc attctaactg gtgtgagatg gtatctcatt   6480
gtggttttga tttgcgtttc tctgatggcc agtgatggtg agcatttttt catgtgtttt   6540
ttggctgcat aaatgtcttc ttttgagaag tgtctgttca tgtccttcgc ccactttttg   6600
atggggttgt ttttttctta taaatttgtt tgagttcatt gtagattctg gatattagcc   6660
ctttgtcaga tgagtaggtt gcaaaaatgt tctcccattt tgtgggttgc ctgttcactc   6720
tgatggtagt ttcttttgct gtgcagaagc tctttagttt aattagatcc catttgtcaa   6780
ttttggcttt tgttgccatt gcttttggca taggcatgaa gtccttgccc atgcctatgt   6840
cctgaatggt aatgcctagg ttttcttcta gggtttttat ggttttaggt ctaacgttta   6900
agtctttaat ccatcttgaa ttgatttttg tataaggtgt aaggaaggga tccagtttca   6960
gctttttaca tatggctagc cagttttccc agcaccattt attacatagg gaatcctttc   7020
cccattgctt gtttttctca ggtttgtcaa agatcagata gttgtagata tgcggcgtta   7080
tttctgaggg ctctgttctg ttccattgat ctatgtgtct gttttggtac cagtaccata   7140
ctgttttggt tactgtagcc ttgtagtata gtttgaagtc aggtagcgtg atgcctccag   7200
ctttgttctt ttggcttagg attgacttgg cgatgcgggc tctttttttgg ttccatatga   7260
actttaaagt agtttttttcc aattctgtga agaaagtcat tggtagcttg atggggatgg   7320
cattgaatct ataaattacc ttgggcagta tggccatttt cacgatattg attcttccta   7380
cccatgagca tggaatggtc ttccatttct ttgtatcctc ttttatttca ttgagcagtg   7440
gtttgtagtt ctccttgaag aggtccttca catccctttt aaggtggatt cctaggtatt   7500
ttattctctt tgaagcaatt gtgagtggaa gttcactcat gatttggctc tctgtttgtc   7560
tgttattggt gtataagaat gcttgtgatt tttgcagatt gattttatat cctgagactt   7620
tgctgaagct gcttatcagc ttaaggagat tttgggctga gacaatgggg ttttctagat   7680
atacaatcat gtcgtctgca aacagggaca atttgacttc ctcttttcct aattgaatac   7740
cctttatttc cttctcctgc ctaattgccc tggccagaac ttccaacact atgttgaata   7800
ggagtggtga gagagggcat ccctgtcttg tgccagtttt caaagggaat gcttccagtt   7860
tttgcccatt cactatgata ttggctgtgg ctttgtcata gatagctctt attattttga   7920
aatatgttcc atcaatacct aatttattga gagtttttag catgatgtgt tgttgaattt   7980
tgtcaaaggc tttttctgca tctattgaga taatcatgtg gtttttgtct ttggatctgt   8040
ttatatgctg gattacattt attgatttgc gtatattgaa ccagccttgc atcctaggga   8100
tgaagcccac atgatcatgg tggataagct ttttgatgtg ctgctggatt cggtttgcca   8160
gtattttatt gaggattttt gcatcaatgt tcatcaagga tattggtcta aaattctctt   8220
ttttggtgtg tctctgccca gctttggtat caggatgatg ttggcttcat aaaatgagtt   8280
agggaggatt ccctcttttt ctattgattg gaatagtttc agaaggaatg gtaccagttc   8340
ctctttgtac ctctggagaa ttcggctgtg aatccatctg gtcctggact ctctttggtt   8400
```

-continued

```
ggtaagctat tgattattgc cacaatttca gctcctgtta ttggtctatt cagagattca   8460
acttcttcct ggtttagtct tgggagagtg tatgtgtcaa ggaatttatc catttcttct   8520
agattttcta gtttatttgc gtagaggtgt ttgtagtaat ctctgatggt agtttgtatt   8580
tctgtgggat cggtggtgat atcccctttta tcatttttta ttgcgtctat ttgattcttc   8640
tctttttctt tattagtctt gctagcggtc tataaatttt gttgatcctt tcaaaaaacc   8700
agctcctgga ttcattaatt ttttgaaggg ttttttgtgt ctctatttcc ttcagttctg   8760
ctctgatttt agttatttct tgccttctgc tagcttttga atatgtttgc tcttgctttt   8820
ctagttcttt taattgtgat gttagggtgt caattttgga tctttcctgc tttctcttgt   8880
gggcatttag tgctataaat ttccctctac acactgcttt gaatgtgtcc cagaggttct   8940
ggtatgttgt gtctttgttc ttgttggttt caaagaacat ctttatttct gccttcattt   9000
cgttatgtac ccagtagtca ttcaggagca ggttgttcag tttccatgta gttgagcagt   9060
tttgagtgag attcttaatc ctgagttcta gtttgattgc actgtggtct gagagatagt   9120
ttgttataat ttctgttctt ttacatttgc tgaggagagc tttacttcca actatgtggt   9180
cggttttgga ataggtgtgg tgtggtgctg aaaaaaatgt atattctgtt gatttgggat   9240
ggagttctgt agatgtctat taggtctgct tggtgcagag ctgagttcaa ttcctgggta   9300
tccttgttga ctttctgtct cgttgatctg tgtactgttg acagtgggtg ttaaagtctc   9360
ccattattaa tgtgtggagt ctaagtctct ttgtaggtca ctcagatgat tggcacttac   9420
tgggcgcttg gcactttcca tactgtgtca tcggcagata gctgcatggt tggtgttcgt   9480
gctggggaat gggaagttca tcggtgggac aaggacaaaa tgcccccatt gctttgttgt   9540
ggctttaatc tccctttcga ggctgagcca cagcgtgctg taggtggcgc tgctgtgaag   9600
cgcagtacca gggtcacact ccactcccag ctctgcagag gtggagaaag aatgaaacat   9660
ctcactcctg gacttccact ttcctgtcac tgttggtgtc acctcttact ggatgtcaca   9720
gagcccagcc cctcccacct gtgcctagga aaagcagatg ccaccttgga atgtggggtt   9780
tgtgtgtgca atttactagc tgggcagaga ccagcaacct ggagagcagg tgtctcgtct   9840
aaggggacag tcacatttca cctccagcca cctggaggaa tttgggcctg gtgatgtcag   9900
aattcttcaa taaaagccta aaatctatat tttatgtgcg gtcatgagat ctgttaaatg   9960
ttagcaactt caggaagttt aaaaatgctg tgtggaccta gaataggcaa gttcttaaag  10020
gcagaaagtg gaatgctagt ttccagggac tggggaacag ggaggaatgg ggagttcatg  10080
tttaatgggc acagaggttt tgttagggat gacgaaaaag ttcgggagat ggtgatggtg  10140
atggagatgg tgatggtgat ggagatggtg atggtgatgg tgatggtgat gggtgatggt  10200
gatggtgatg gtgatggtga tggagatggt gatggtgatg gtgatggaga tggtgatggt  10260
gatggtgatg gtgatggaga tggtgatggt gatggagatg gtgatggtga tggtgatgga  10320
gatggtgatg gtgatggtga tggtgatggt gatggtgatg gtgatggaga tggagatggt  10380
gatggtgatg gttgcctaac atcaggaacg tgcttaatgc ttctgaattg cacacaaaaa  10440
tggcaagttt aatattatgt gtactttatc acaatgaaaa aagctgctgc gtgggccaag  10500
ttacttgtgc aggtaatgtt ctgcaggtgg ttgcctgcac ctcagttgta gggtgtccgt  10560
aggatgtgag gccagtcccc gggcttaatg atgctttaaa tcctgcctag tattcaatta  10620
tttcttgtcg cttaaaaggc ctaataaaat tatggtctta gtttacagtg gtatgaatgc  10680
ttagctgttg gattttagta ggaaagttcg tcccttttttg tttttaattt tgttttacag  10740
attcacagga attttttttt tttttttttt tttttttttt taatgcacag aaagtttccc  10800
```

-continued

```
tggactctct acccagtttc cccagtgata atatcttggg taacatcctg tatacattca  10860
cattggtgca ttcctcagag ttgtcagatt ttgctagttt tacgtgcact tgtgtatgtg  10920
tgtatttgca attttagcac gtgtagactc ttgtaaccac tacaatcaag ttacagaact  10980
acactaccaa ggttcatctt tttaaaatct ttgatgttac ctttttttgga acagtgacca  11040
tgagaggact ttcctcccaa aattttgaaa actactgaac cagaatatag tctgacacta  11100
ataggtagaa atttaaccaa aggagattat gaagctctgc acttgagtta acaaaatcac  11160
ttctcagctt ccagttccat ctcagaagga aggaaaaggg attaaaaatc cagagaccag  11220
aaaatgggag caaagtacaa ggtggtgtaa tcattacaga ggtttcctga tgtttccaag  11280
tcagtcgtgt gttgagctgc taaactctaa agtaatttta ggtggaatgt tggaaacatg  11340
ctgctgaggt gatagaaagg aatccatggt cctctgttag ttggaaagta tatggaatac  11400
tatattctac ataagataca atactctctg tgagacaagg ataaagtaga ttttgtcagt  11460
gaaattgtga caagaatcgc tgatgggttt agagcctaag tttgcgagga gcactggaag  11520
aaattaagat tgttgagatt ggaaagggtt agctatgggg gaacaggagg aggtgactcc  11580
atgacagacc aaatattcaa aggactgtgt agaagaggaa aaagactttg ttagggctcc  11640
agaggacaga gccaggagtc agacagggcc ttgaactcaa cccaccgaga tctgcaaact  11700
ttgcaggatg caccagatgt cttgtagcca tgggtcaagg ggggaccctg ggtaagagac  11760
tgtaatagat gacctctaag gccatctcat gacatgtgtg attaatgtat gtacctgtcc  11820
tctctttttg acaattctac agattattca ggacagggag ttgaccaact gcaaagagtg  11880
attgacacca tcaaaaccaa ccctgacgac agaagaatca tcatgtgcgc ttggaatcca  11940
agaggttgaa agaaccccgt cgtcttcatt tatactaacc atactcttag agggaagcaa  12000
tctggttttg tgcagaggca ctgagggagg caggaccctg ggcaacttcc cccagccaca  12060
tggttgtgtg acgttgggca agtcacattt tgctgcactt tcaccttcag atcatgaggt  12120
tgggcccaga ggattttttt tttttttttt ttttttgaga cagagttttg ctctgttgcc  12180
caggctggaa tgcaacggcg tgatcttggc tcactgtaac ctctgcctcc tgggttcgag  12240
tgattctcct gcctcagcct ccaagtagct gggattacag catgtgccac catgcctggc  12300
taattttgta tttttagtag agacgggttc acatgttggt caggctggtc ttgactcctg  12360
accctcagat gatctgcctt gcctcagcct cccaaccgag tgatcttaag ttgtgtatta  12420
tactcattct tacacaaaaa gggctttaaa tgcctagaaa ctacatgaag atgttaacat  12480
tttaaatgga agcagatgaa gttccagctc gctgccacct cactaacatt tttaacaatt  12540
atattgtaaa attcaactct accagggtgt agagccaggt gtggtggctc acacctgtaa  12600
ttccaacaac tccagaggcc aaggcgagag gatcatttga acccacggaa tttgaggctg  12660
tagtgagtca tgatcacgcc attgcactcc atcctgggca acagagtgag accctgaata  12720
tttaaaaaca acaacaacaa caaaactcta tcaggatatc ataagtactt agagtgaaat  12780
acttgcatct gtaatagaga cttatttttt ttttttttga gacacagtct caccctgttg  12840
cccaggctgg agtgcagtgg tttgatctcc gctcacggca acctccatct cccaggttca  12900
agtgagttcc cattcctcag ccccagagct gggaccacag gcgcgcgaat ttttgtattt  12960
ttagcagaga cggggtttca ctatgttggc caggctagtc tcaaactcaa gttggcctca  13020
agtgatctgc ccaccctggc gtcccagtgt tgggatttca ggcatgagcc actgtgcctg  13080
gccatgtaat agagactttt aatataggag ggtgtaccag aagcaccagt ttcctgtggc  13140
```

-continued

```
aaacagaatt attcctgctg tatttgtaat ttggtgccac gaggtagccc agatcccttc  13200
agctctgatg gaagagcatt gcttcagccg taaatggaca cctgcagaaa ccttgcaccg  13260
atggatagtc tccctcagct ccgtgccatc gctgcagggg ctgttatgga catcactgca  13320
gcccagtggc tctctctcct ggtctccacc atatgagttg gcttctgttt ctctcctgtt  13380
ttactttgcc tttagctgtg gtctttcaaa ccaccatccc tccttatctt cctctgctgg  13440
ttcctcagat cttcctctga tggcgctgcc tccatgccat gccctctgcc agttctatgt  13500
ggtgaacagt gagctgtcct gccagctgta ccagagatcg ggagacatgg gcctcggtgt  13560
gcctttcaac atcgccagct acgccctgct cacgtacatg attgcgcaca tcacgggcct  13620
gaaggtgggc tgtctcggga agggtgactt gccagcctac cacatgagct cttcagttct  13680
ttaatatggg aaaacaaatt gcagagttta gtctctgatt agcttttaaa tttgatatgt  13740
gtaagtaaga catgaaccag cttttacttt gaaaccttcc ttttctggaa ggttttctgg  13800
ccctgtggta tatgcactaa cagatctata caggttgttt gtgatacagc ttctatggat  13860
cttctcaaaa gctatgctga ggttgggtat ggtggctcat gcctgtaatc ccagcacttt  13920
ggaagactga gacaggagca attgcttgag gtctggagtt caataccagc ctgggcaaca  13980
taacaagatg ctgttgctac aaaaaaatgg aaaagctaca ctaaattatt tttttaaaaa  14040
aagccttgcg gtgtctgcat attctaatgt ttttaaatga tgttttaaag aattgaaact  14100
aacatactgt tctgctttct cccggtttat agccaggtga ctttatacac actttgggag  14160
atgcacatat ttacctgaat cacatcgagc cactgaaaat tcaggtaaga attagatgtt  14220
atacttttgg gtttggtacc ttctcttgat aaaaggttga ctgtggaaca ggtatctgct  14280
caatgctgtg tccaagataa agatgactgc tccaaatgtg gggcttcagt ttagggagaa  14340
gtggtgggca ggtgggcagg acaaggcagg catctgcctc agcaaccatg gcacttaact  14400
tgtcaggtgc tgtgaggtac taagcaccag taccagagag ggaagagcca cattcaagcc  14460
aggggattgt ccaaaaggag gcattttaac tcattttaac ttgaaggaga attgaagtgc  14520
aaatgttttt ccttttcttt ttttttgaga tggagtcttt ctctgtcggc caggctggag  14580
tgtgccgtgg tgcgatctca gctcactgca acctccacct cccgggttca agcaattctt  14640
ctgcctcagc ctcccaggta gctgggatta caggcacatg ccaccacacc cagctaattt  14700
tttgtattat tagtagagat ggggtttcgt catgttggcc aggctgatct caaactcctg  14760
acttcaagtg taccacctgc ctcagcctcc gaaagttctg gaattacagg cataagccac  14820
caccctggcc ataaatattt tttgttaatt ttacattaag tacaatattt aggtccaaac  14880
ttcaaaagtc tgttgaaatc cctgaagtta tagcagccaa caattgatat gaaatggcaa  14940
taaaaatgta agttcatctg cttcatgagc cttaaggaaa aaaactcaga accagacact  15000
ttttagcccc ttccaggtta gatccaggtt ttaaaagtta ttcctttgag ggagtttggc  15060
tgcttttgag tggaggtgac ttcaggctta ttctctctgg ctctctgctc tggtcatttt  15120
tagacatagt aataggttgt gacctgtctt cacatcctaa ttgccactgt ctgttcatcc  15180
caggaatcct ggctttcatc cctttctgtt cactgtccat gcatgtcatc tttccttctt  15240
tctgccaggg accagatggg ttagggattg tgaattcaag taaacgtaga gctactatga  15300
gttacagatt gactgtgttc ctgtctttaa taaatttgcc aagagtggtt ataagaactt  15360
acacctgatg aggcaccagg ctcctgatgc tgtgtaatgt cacaaaatac ccctcactct  15420
cgatctgtgc aagagaacag ctggttgcgc tccaatcatg ttacataacc tacgcgaagg  15480
tatcgacagg atcatactcc tgtaaaatag aactttgttg atcacatcct gtgtacttgt  15540
```

-continued

```
ttcacggaca tgaggagcaa ttacaacagg tcgtacaatt atggcaaaat aatggcctta  15600
ttttgttttt agcttcagcg agaacccaga cctttcccaa agctcaggat tcttcgaaaa  15660
gttgagaaaa ttgatgactt caaagctgaa gactttcaga ttgaagggta caatccgcat  15720
ccaactatta aaatggaaat ggctgtttag ggtgctttca aaggagctcg aaggatattg  15780
tcagtcttta ggggttgggc tggatgccga ggtaaaagtt ctttttgctc taaaagaaaa  15840
aggaactagg tcaaaaatct gtccgtgacc tatcagttat taatttttaa ggatgttgcc  15900
actggcaaat gtaactgtgc cagttctttc cataataaaa ggctttgagt taactcactg  15960
agggtatctg acaatgctga ggttatgaac aaagtgagga gaatgaaatg tatgtgctct  16020
tagcaaaaac atgtatgtgc atttcaatcc cacgtactta taaagaaggt tggtgaattt  16080
cacaagctat ttttggaata tttttagaat attttaagaa tttcacaagc tattccctca  16140
aatctgaggg agctgagtaa caccatcgat catgatgtag agtgtggtta tgaactttaa  16200
agttatagtt gttttatatg ttgctataat aaagaagtgt tctgcattcg tccacgcttt  16260
gttcattctg tactgccact tatctgctca gttccttcct aaaatagatt aaagaactct  16320
ccttaagtaa acatgtgctg tattctggtt tggatgctac ttaaaagagt atattttaga  16380
aataatagtg aatatatttt gccctatttt tctcatttta actgcatctt atcctcaaaa  16440
tataatgacc atttaggata gagttttttt tttttttttt taaactttta taaccttaaa  16500
gggttatttt aaaataatct atggactacc attttgccct cattagcttc agcatggtgt  16560
gacttctcta ataatatgct tagattaagc aaggaaaaga tgcaaaacca cttcggggtt  16620
aatcagtgaa atatttttcc cttcgttgca taccagatac ccccggtgtt gcacgactat  16680
ttttattctg ctaatttatg acaagtgtta aacagaacaa ggaattattc caacaagtta  16740
tgcaacatgt tgcttatttt caaattacag tttaatgtct aggtgccagc ccttgatata  16800
gctatttttg taagaacatc ctcctggact ttgggttagt taaatctaaa cttatttaag  16860
gattaagtag gataacgtgc attgatttgc taaaagaatc aagtaataat tacttagctg  16920
attcctgagg gtggtatgac ttctagctga actcatcttg atcggtagga ttttttaaat  16980
ccatttttgt aaaactattt ccaagaaatt ttaagccctt tcacttcaga aagaaaaaag  17040
ttgttggggc tgagcactta attttcttga gcaggaagga gtttcttcca aacttcacca  17100
tctggagact ggtgtttctt tacagattcc tccttcattt ctgttgagta gccgggatcc  17160
tatcaaagac caaaaaaatg agtcctgtta acaaccacct ggaacaaaaa cagattttat  17220
gcatttatgc tgctccaaga aatgctttta cgtctaagcc agaggcaatt aattaatttt  17280
tttttttttg acatggagtc actgtccgtt gcccaggctg cagtgcagtg gcgcaatctt  17340
ggctcactgc aacctccacc tcccaggttc aagtgattct cctgcctcag cctcccatgt  17400
agctgggatc acaggcacct gccaccatgc ccggctaatt ttttgtattt tttgtagaga  17460
cagggtttca ccatgttggc caggctggtc tcaaacacct gacctcaaat gatccacctg  17520
cctcagcctc ccaaagtgtt gggattacag gcgtaagcca ccatgcccag ccctgaatta  17580
atatttttaa aataagtttg gagactgttg gaaataatag ggcagaggaa catattttac  17640
tggctacttg ccagagttag ttaactcatc aaactctttg ataatagttt gacctctgtt  17700
ggtgaaaatg agccatgatc tcttgaacat gatcagaata aatgccccag ccacacaatt  17760
gtagtccaaa ctttttaggt cactaacttg ctagatggtg ccaggttttt ttgcacaagg  17820
agtgcaaatg ttaagatctc cactagtgag gaaaggctag tattacagaa gccttgtcag  17880
```

-continued

```
aggcaattga acctccaagc cctggccctc aggcctgagg attttgatac agacaaactg  17940

aagaaccgtt tgttagtgga tattgcaaac aaacaggagt caaagcttgg tgctccacag  18000

tctagttcac gagacaggcg tggcagtggc tggcagcatc tcttctcaca ggggccctca  18060

ggcacagctt accttgggag gcatgtagga agcccgctgg atcatcacgg gatacttgaa  18120

atgctcatgc aggtggtcaa catactcaca caccctagga ggagggaatc agatcggggc  18180

aatgatgcct gaagtcagat tattcacgtg gtgctaactt aaagcagaag gagcgagtac  18240

cactcaattg acagtgttgg ccaaggctta gctgtgttac catgcgtttc taggcaagtc  18300

cctaaacctc tgtgcctcag gtccttttct tctaaaatat agcaatgtga ggtggggact  18360

ttgatgacat gaacacacga agtccctctg agaggttttg tggtgccctt taaaagggat  18420

caattcagac tctgtaaata tccagaatta tttgggttcc tctggtcaaa agtcagatga  18480

atagattaaa atcaccacat tttgtgatct atttttcaag aagcgtttgt atttttttcat  18540

atggctgcag cagctgccag gggcttgggg ttttttttggc aggtagggtt gggagg      18596
```

```
<210> SEQ ID NO 12
<211> LENGTH: 3291
<212> TYPE: DNA
<213> ORGANISM: Homo sapiens

<400> SEQUENCE: 12

accgggcaag cgggaaccag gtggccaccc ggtgtcggtt tcattttcct ttggaatttc     60

tgctttacag acagaacaat ggcagcccga gtacttataa ttggcagtgg aggaagggaa    120

catacgctgg cctggaaact tgcacagtct catcatgtca aacaagtgtt ggttgcccca    180

ggaaacgcag gcactgcctg ctctgaaaag atttcaaata ccgccatctc aatcagtgac    240

cacactgccc ttgctcaatt ctgcaaagag aagaaaattg aatttgtagt tgttggacca    300

gaagcacctc tggctgctgg gattgttggg aacctgaggt ctgcaggagt gcaatgcttt    360

ggcccaacag cagaagcggc tcagttagag tccagcaaaa ggtttgccaa agagtttatg    420

gacagacatg gaatcccaac cgcacaatgg aaggctttca ccaaacctga agaagcctgc    480

agcttcattt tgagtgcaga cttccctgct ttggttgtga aggccagtgg tcttgcagct    540

ggaaaagggg tgattgttgc aaagagcaaa gaagaggcct gcaaagctgt acaagagatc    600

atgcaggaga aagcctttgg ggcagctgga gaaacaattg tcattgaaga acttcttgac    660

ggagaagagg tgtcgtgtct gtgtttcact gatggcaaga ctgtggcccc catgccccca    720

gcacaggacc ataagcgatt actggaggga gatggtggcc ctaacacagg ggggaatggga    780

gcctattgtc cagcccctca ggtttctaat gatctattac taaaaattaa agatactgtt    840

cttcagagga cagtggatgg catgcagcaa gagggtactc catatacagg tattctctat    900

gctggaataa tgctgaccaa gaatggccca aaagttctag agtttaattg ccgttttggt    960

gatccagagt gccaagtaat cctcccactt cttaaaagtg atctttatga agtgattcag   1020

tccaccttag atggactgct ctgcacatct ctgcctgttt ggctagaaaa ccacaccgcc   1080

ctaactgttg tcatggcaag taaaggttat cctggagact acaccaaggg tgtagagata   1140

acagggtttc ctgaggctca agctctagga ctggaggtgt tccatgcagg cactgccctc   1200

aaaaatggca aagtagtaac tcatggggggt agagttcttg cagtcacagc catccgggaa   1260

aatctcatat cagcccttga ggaagccaag aaaggactag ctgctataaa gtttgaggga   1320

gcaatttata ggaaagacgt cggctttcgt gccatagctt tcctccagca gcccaggagt   1380

ttgacttaca aggaatctgg agtagatatc gcagctggaa atatgctggt caagaaaatt   1440
```

```
cagcctttag caaaagccac ttccagatca ggctgtaaag ttgatcttgg aggttttgct   1500
ggtctttttg atttaaaagc agctggtttc aaagatcccc ttctggcctc tggaacagat   1560
ggcgttggaa ctaaactaaa gattgcccag ctatgcaata aacatgatac cattggtcaa   1620
gatttggtag caatgtgtgt taatgatatt ctggcacaag gagcagagcc cctcttcttc   1680
cttgattact tttcctgtgg aaaacttgac ctcagtgtaa ctgaagctgt tgttgctgga   1740
attgctaaag cttgtggaaa agctggatgt gctctccttg gaggtgaaac agcagaaatg   1800
cctgacatgt atcccccctgg agagtatgac ctagctgggt ttgccgttgg tgccatggag   1860
cgagatcaga aactccctca cctggaaaga atcactgagg gtgatgttgt tgttggaata   1920
gcttcatctg gtcttcatag caatggattt agccttgtga ggaaaatcgt tgcaaaatct   1980
tccctccagt actcctctcc agcacctgat ggttgtggtg accagacttt aggggactta   2040
cttctcacgc ctaccagaat ctacagccat tcactgttac ctgtcctacg ttcaggacat   2100
gtcaaagcct ttgcccatat tactggtgga ggattactag agaacatccc cagagtcctc   2160
cctgagaaac ttggggtaga tttagatgcc cagacctgga ggatccccag ggtttttctca   2220
tggttgcagc aggaaggaca cctctctgag gaagagatgg ccagaacatt taactgtggg   2280
gttggcgctg tccttgtggt atcaaaggag cagacagagc agattctgag ggatatccag   2340
cagcacaagg aagaagcctg ggtgattggc agtgtggttg cacgagctga aggttcccca   2400
cgtgtgaaag tcaagaatct gattgaaagc atgcaaataa atgggtcagt gttgaagaat   2460
ggctccctga caaatcattt ctcttttgaa aaaaaaaagg ccagagtggc tgtcttaata   2520
tctggaacag gatcgaacct gcaagcactt atagacagta ctcgggaacc aaatagctct   2580
gcacaaattg atattgttat ctccaacaaa gccgcagtag ctgggttaga taaagcggaa   2640
agagctggta ttcccactag agtaattaat cataaactgt ataaaaatcg tgtagaattt   2700
gacagtgcaa ttgacctagt ccttgaagag ttctccatag acatagtctg tcttgcagga   2760
ttcatgagaa ttctttctgg cccctttgtc caaaagtgga atggaaaaat gctcaatatc   2820
cacccatcct tgctcccttc ttttaagggt tcaaatgccc atgagcaagc cctggaaacc   2880
ggagtcacag ttactgggtg cactgtacac tttgtagctg aagatgtgga tgctggacag   2940
attattttgc aagaagctgt tcccgtgaag aggggtgata ctgtcgcaac tctttctgaa   3000
agagtaaaat tagcagaaca taaaatattt cctgcagccc ttcagctggt ggccagtgga   3060
actgtacagc ttggagaaaa tggcaagatc tgttgggtta aagaggaatg aagcctttta   3120
attcagaaat ggggccagtt tagaaagaat tatttgctgt ttgcatggtg gtttttttatc   3180
atggacttgg cccaaaagaa aaactgctaa aagacaaaaa agacctcacc cttacttcat   3240
ctattttttt aataaataga gactcactaa aaaaaaaaaa aaaaaaaaaa a            3291
```

<210> SEQ ID NO 13
<211> LENGTH: 1776
<212> TYPE: DNA
<213> ORGANISM: Homo sapiens

<400> SEQUENCE: 13

```
atggtgccct ccagcccagc ggtggagaag caggtgcccg tggaacctgg gcctgacccc     60
gagctccggt cctggcggcg cctcgtgtgc tacctttgct tctacggctt catggcgcag    120
atacggccag gggagagctt catcaccccc tacctcctgg ggcccgacaa gaacttcacg    180
cgggacgagg tcacgaacga gatcacgccg gtgctgtcgt actcctacct ggccgtgctg    240
```

-continued

```
gtgcccgtgt tcctgctcac cgactacctg cgctacacgc cggtgctgct gctgcagggg    300
ctcagcttcg tgtcggtgtg gctgctgctg ctgctgggcc actcggtggc gcacatgcag    360
ctcatggagc tcttctacag cgtcaccatg gccgcgcgca tcgcctattc ctcctacatc    420
ttctctctcg tgcggcccgc gcgctaccag cgtgtggccg gctactcgcg cgctgcggtg    480
ctgctgggcg tgttcaccag ctccgtgctg ggccagctgc tggtcactgt gggccgagtc    540
tccttctcca cgctcaacta catctcgctg gccttcctca ccttcagcgt ggtcctcgcc    600
ctcttcctga agcgccccaa gcgcagcctc ttcttcaacc gcgacgaccg ggggcggtgc    660
gaaacctcgg cttcggagct ggagcgcatg aatcctggcc caggcgggaa gctgggacac    720
gccctgcggg tggcctgtgg ggactcagtg ctggcgcgga tgctgcggga gctgggggac    780
agcctgcggc ggccgcagct gcgcctgtgg tccctctggt gggtcttcaa ctcggccggc    840
tactacctgg tggtctacta cgtgcacatc ctgtggaacg aggtggaccc caccaccaac    900
agtgcgcggg tctacaacgg cgcggcagat gctgcctcca cgctgctggg cgccatcacg    960
tccttcgccg cgggcttcgt gaagatccgc tgggcgcgct ggtccaagct gctcatcgcg   1020
ggcgtcacgg ccacgcaggc ggggctggtc ttccttctgg cgcacacgcg ccacccgagc   1080
agcatctggc tgtgctatgc ggccttcgtg ctgttccgcg gctcctacca gttcctcgtg   1140
cccatcgcca cctttcagat tgcatcttct ctgtctaaag agctctgtgc cctggtcttc   1200
ggggtcaaca cgttctttgc caccatcgtc aagaccatca tcactttcat tgtctcggac   1260
gtgcggggcc tgggcctccc ggtccgcaag cagttccagt tatactccgt gtacttcctg   1320
atcctgtcca tcatctactt cttgggggcc atgctggatg gcctgcgcga ctgccagcgg   1380
ggccaccacc cgcggcagcc cccggcccag ggcctgagga gtgccgcgga ggagaaggca   1440
gcacagcgac tgagcgtgca ggacaagggc ctcggaggcc tgcagccagc ccagagcccg   1500
ccgctttccc cagaagacag cctgggggct gtggggccag cctccctgga gcagagacag   1560
agcgacccat acctggccca ggccccggcc ccgcaggcag ctgaattcct gagcccagtg   1620
acaacccctt cccccctgcac tctgtcgtcc gcccaagcct caggccctga ggctgcagat   1680
gagacttgtc cccagctggc tgtccatcct cctggtgtca gcaagctggg tttgcagtgt   1740
cttccaagcg acggtgttca gaatgtgaac cagtga                              1776
```

<210> SEQ ID NO 14
<211> LENGTH: 2500
<212> TYPE: DNA
<213> ORGANISM: Homo sapiens

<400> SEQUENCE: 14

```
tgaatcgccc ggggtcgccg tctccgcctc gccgcagtcg gggcagccgc tgccctcttt     60
tccatgtatc gtccaggatc ccatgacaga ttctgttgtc acgtctcctt acagagtttg    120
agcggtgctg aactgtcagc acatctgtcc ggtccagcat gccttctgag accccccagg    180
cagaagtggg gcccacaggc tgcccccacc gctcagggcc acactcggcg aaggggagcc    240
tggagaaggg gtccccagag gataaggaag ccaaggagcc cctgtggatc cggcccgatg    300
ctccgagcag gtgcacctgg cagctgggcc ggcctgcctc cgagtcccca catcaccaca    360
ctgccccggc aaaatctcca aaaatcttgc cagatattct gaagaaaatc ggggacaccc    420
ctatggtcag aatcaacaag attgggaaga agttcggcct gaagtgtgag ctcttggcca    480
agtgtgagtt cttcaacgcg ggcgggagcg tgaaggaccg catcagcctg cggatgattg    540
aggatgctga gcgcgacggg acgctgaagc ccggggacac gattatcgag ccgacatccg    600
```

-continued

```
ggaacaccgg gatcgggctg gccctggctg cggcagtgag gggctatcgc tgcatcatcg    660
tgatgccaga gaagatgagc tccgagaagg tggacgtgct gcgggcactg gggggctgaga   720
ttgtgaggac gcccaccaat gccaggttcg actccccgga gtcacacgtg ggggtggcct    780
ggcggctgaa gaacgaaatc cccaattctc acatcctaga ccagtaccgc aacgccagca    840
acccccctggc tcactacgac accaccgctg atgagatcct gcagcagtgt gatgggaagc   900
tggacatgct ggtggcttca gtgggcacgg gcggcaccat cacgggcatt gccaggaagc    960
tgaaggagaa gtgtcctgga tgcaggatca ttggggtgga tcccgaaggg tccatcctcg   1020
cagagccgga ggagctgaac cagacggagc agacaaccta cgaggtggaa gggatcggct   1080
acgacttcat ccccacggtg ctggacagga cggtggtgga caagtggttc aagagcaacg   1140
atgaggaggc gttcaccttt gcccgcatgc tgatcgcgca agaggggctg ctgtgcggtg   1200
gcagtgctgg cagcacggtg gcggtggccg tgaaggctgc gcaggagctg caggagggcc   1260
agcgctgcgt ggtcattctg cccgactcag tgcggaacta catgaccaag ttcctgagcg   1320
acaggtggat gctgcagaag ggctttctga aggaggagga cctcacggag aagaagccct   1380
ggtggtggca cctccgtgtt caggagctgg gcctgtcagc cccgctgacc gtgctcccga   1440
ccatcacctg tgggcacacc atcgagatcc tccgggagaa gggcttcgac caggcgcccg   1500
tggtggatga ggcgggggta atcctgggaa tggtgacgct tgggaacatg ctctcgtccc   1560
tgcttgccgg gaaggtgcag ccgtcagacc aagttggcaa agtcatctac aagcagttca   1620
aacagatccg cctcacggac acgctgggca ggctctcgca catcctggag atggaccact   1680
tcgccctggt ggtgcacgag cagatccagt accacagcac cgggaagtcc agtcagcggc   1740
agatggtgtt cggggtggtc accgccattg acttgctgaa cttcgtggcc gcccaggagc   1800
gggaccagaa gtgaagtccg gagcgctggg cggtgcggag cgggcccgcc acccttgccc   1860
acttctcctt cgctttcctg agccctaaac acacgcgtga ttggtaactg cctggcctgg   1920
caccgttatc cctgcagacg gcacagagca tccgtctccc ctcgttaaca catggcttcc   1980
taaatggccc tgtttacggc ctatgagatg aaatatgtga ttttctctaa tgtaacttcc   2040
tcttaggatg tttcaccaag gaaatattga gagagaagtc ggccaggtag gatgaacaca   2100
ggcaatgact gcgcagagtg gattaaaggc aaaagagaga agagtccagg aaggggcggg   2160
gagaagcctg ggtggctcag catcctccac gggctgcgcg tctgctcggg gctgagctgg   2220
cgggagcagt ttgcgtgttt gggtttttta attgagatga aattcaaata acctaaaaat   2280
caatcacttg aaagtgaaca atcagcggca tttagtacat ccagaaagtt gtgtaggcac   2340
cacctctgtc acgttctgga acattctgtc atcaccccgt gaagcaatca tttcccctcc   2400
cgtcttcctc ctcccctggc aactgctgat cgactttgtg tctctgttgt ctaaaatagg   2460
ttttccctgt tctggacatt tcatataaat ggaatcacac                          2500

<210> SEQ ID NO 15
<211> LENGTH: 2068
<212> TYPE: DNA
<213> ORGANISM: Homo sapiens

<400> SEQUENCE: 15

cggcagccct cctacctgcg cacgtggtgc cgctgctgct gcctcccgct cgccctgaac     60
ccagtgcctg cagccatggc tcccggccag ctcgccttat ttagtgtctc tgacaaaacc    120
ggccttgtgg aatttgcaag aaacctgacc gctcttggtt tgaatctggt cgcttccgga    180
```

-continued

```
gggactgcaa aagctctcag ggatgctggt ctggcagtca gagatgtctc tgagttgacg    240
ggatttcctg aaatgttggg gggacgtgtg aaaactttgc atcctgcagt ccatgctgga    300
atcctagctc gtaatattcc agaagataat gctgacatgg ccagacttga tttcaatctt    360
ataagagttg ttgcctgcaa tctctatccc tttgtaaaga cagtggcttc tccaggtgta    420
actgttgagg aggctgtgga gcaaattgac attggtggag taaccttact gagagctgca    480
gccaaaaacc acgctcgagt gacagtggtg tgtgaaccag aggactatgt ggtggtgtcc    540
acggagatgc agagctccga gagtaaggac acctccttgg agactagacg ccagttagcc    600
ttgaaggcat tcactcatac ggcacaatat gatgaagcaa tttcagatta tttcaggaaa    660
cagtacagca aaggcgtatc tcagatgccc ttgagatatg gaatgaaccc acatcagacc    720
cctgcccagc tgtacacact gcagcccaag cttcccatca cagttctaaa tggagcccct    780
ggatttataa acttgtgcga tgctttgaac gcctggcagc tggtgaagga actcaaggag    840
gctttaggta ttccagccgc tgcctctttc aaacatgtca gcccagcagg tgctgctgtt    900
ggaattccac tcagtgaaga tgaggccaaa gtctgcatgg tttatgatct ctataaaacc    960
ctcacaccca tctcagcggc atatgcaaga gcaagagggg ctgataggat gtcttcattt   1020
ggtgattttg ttgcattgtc cgatgtttgt gatgtaccaa ctgcaaaaat tatttccaga   1080
gaagtatctg atggtataat tgccccagga tatgaagaag aagccttgac aatactttcc   1140
aaaaagaaaa atggaaacta ttgtgtcctt cagatggacc aatcttacaa accagatgaa   1200
aatgaagttc gaactctctt tggtcttcat ttaagccaga agagaaataa tggtgtcgtc   1260
gacaagtcat tatttagcaa tgttgttacc aaaaataaag atttgccaga gtctgccctc   1320
cgagacctca tcgtagccac cattgctgtc aagtacactc agtctaactc tgtgtgctac   1380
gccaagaacg ggcaggttat cggcattgga gcaggacagc agtctcgtat acactgcact   1440
cgccttgcag gagataaggc aaactattgg tggcttagac accatccaca agtgctttcg   1500
atgaagttta aaacaggagt gaagagagca gaaatctcca atgccatcga tcaatatgtg   1560
actggaacca ttggcgagga tgaagatttg ataaagtgga aggcactgtt tgaggaagtc   1620
cctgagttac tcactgaggc agagaagaag gaatgggttg agaaactgac tgaagtttct   1680
atcagctctg atgccttctt ccctttccga gataacgtag acagagctaa aaggagtggt   1740
gtggcgtaca ttgcggctcc ctccggttct gctgctgaca aagttgtgat tgaggcctgc   1800
gacgaactgg gaatcatcct cgctcatacg aaccttcggc tcttccacca ctgattttac   1860
cacacactgt tttttggctt gcttatgtgt aggtgaacag tcacgcctga aactttgagg   1920
ataacttttt aaaaaaataa aacagtatct cttaaaacaa tgttttgatc tacataaaca   1980
ttgtaaaaat tttcaatcac gctttttaac tttcttacca caaaaaaatg ataagtgggt   2040
gaagtgatgg ttatgttaat tagcgtgc                                      2068
```

<210> SEQ ID NO 16
<211> LENGTH: 857
<212> TYPE: DNA
<213> ORGANISM: Homo sapiens

<400> SEQUENCE: 16

```
gcgtgggcgt gagatggcgg cggcagcggt gagcagcgcc aagcggagcc tgcggggaga     60
gctgaagcag cgtctgcggg cgatgagtgc cgaggagcgg ctacgccagt cccgcgtact    120
gagccagaag gtgattgccc acagtgagta tcaaaagtcc aaaagaattt ccatctttct    180
gagcatgcaa gatgaaattg agacagaaga gatcatcaag gacattttcc aacgaggcaa    240
```

```
aatctgcttc atccctcggt accggttcca gagcaatcac atggatatgg tgagaataga    300

atcaccagag gaaatttctt tacttcccaa aacatcctgg aatatccctc agcctggtga    360

gggtgatgtt cgggaggagg ccttgtccac agggggactt gatctcatct tcatgccagg    420

ccttgggttt gacaaacatg gcaaccgact ggggaggggc aagggctact atgatgccta    480

tctgaagcgc tgtttgcagc atcaggaagt gaagccctac accctggcgt tggctttcaa    540

agaacagatt tgcctccagg tcccagtgaa tgaaaacgac atgaaggtag atgaagtcct    600

ttacgaagac tcgtcaacag cttaaatctg gattactaca gccaaataat cagtgtttta    660

tatgagagta aagcaaagta tgtgtatttt tcccttgtca aaaattagtt gaaattgttc    720

attaatgtga atacagactg cattttaaaa ttgtaattat gaaatacctt atataaaacc    780

atctttaaaa accaatagaa gtgtgaatag tagaatatta attaaaatgg aggctatcag    840

cctgtgattt tcagctt                                                   857
```

<210> SEQ ID NO 17
<211> LENGTH: 3762
<212> TYPE: DNA
<213> ORGANISM: Homo sapiens

<400> SEQUENCE: 17

```
cccgcgagcg tccatccatc tgtccggccg actgtccagc gaaaggggct ccaggccggg     60

cgcacgtcga cccgggggac cgaggccagg agaggggcca agagcgcggc tgacccttgc    120

gggccggggc aggggacggt ggccgcggcc atgcagtcct gtgccagggc gtgggggctg    180

cgcctgggcc gcggggtcgg gggcggccgc cgcctggctg gggcatcggg gccgtgctgg    240

gcgccgcgga gccgggacag cagcagtggc ggcggggaca gcgccgcggc tggggcctcg    300

cgcctcctgg agcgccttct gcccagacac gacgacttcg ctcggaggca catcggccct    360

ggggacaaag accagagaga gatgctgcag accttggggc tggcgagcat tgatgaattg    420

atcgagaaga cggtccctgc caacatccgt ttgaaaagac ccttgaaaat ggaagaccct    480

gtttgtgaaa atgaaatcct tgcaactctg catgccattt caagcaaaaa ccagatctgg    540

agatcgtata ttggcatggg ctattataac tgctcagtgc cacagacgat tttgcggaac    600

ttactggaga actcaggatg gatcacccag tatactccat accagcctga ggtgtctcag    660

gggaggctgg agagtttact caactaccag accatggtgt gtgacatcac aggcctggac    720

atggccaatg catccctgct ggatgagggg actgcagccg cagaggcact gcagctgtgc    780

tacagacaca acaagaggag gaaatttctc gttgatcccc gttgccaccc acagacaata    840

gctgttgtcc agactcgagc caaatatact ggagtcctca ctgagctgaa gttaccctgt    900

gaaatggact tcagtggaaa agatgtcagt ggagtgttgt tccagtaccc agacacggag    960

gggaaggtgg aagactttac ggaactcgtg gagagagctc atcagagtgg gagcctggcc   1020

tgctgtgcta ctgacctttt agctttgtgc atcttgaggc cacctggaga atttggggta   1080

gacatcgccc tgggcagctc ccagagattt ggagtgccac tgggctatgg gggaccccat   1140

gcagcatttt ttgctgtccg agaaagcttg gtgagaatga tgcctggaag aatggtgggg   1200

gtaacaagag atgccactgg gaaagaagtg tatcgtcttg ctcttcaaac cagggagcaa   1260

cacattcgga gagacaaggc taccagcaac atctgtacag ctcaggccct cttggcgaat   1320

atggctgcca tgtttcgaat ctaccatggt tcccatgggc tggagcatat tgctaggagg   1380

gtacataatg ccactttgat tttgtcagaa ggtctcaagc gagcagggca tcaactccag   1440
```

-continued

```
catgacctgt tctttgatac cttgaagatt cattgtggct gctcagtgaa ggaggtcttg   1500
ggcagggcgg ctcagcggca gatcaatttt cggctttttg aggatggcac acttggtatt   1560
tctcttgatg aaacagtcaa tgaaaaagat ctggacgatt tgttgtggat ctttggttgt   1620
gagtcatctg cagaactggt tgctgaaagc atgggagagg agtgcagagg tattccaggg   1680
tctgtgttca agaggaccag cccgttcctc acccatcaag tgttcaacag ctaccactct   1740
gaaacaaaca ttgtccggta catgaagaaa ctggaaaata aagacatttc ccttgttcac   1800
agcatgattc cactgggatc ctgcaccatg aaactgaaca gttcgtctga actcgcacct   1860
atcacatgga aagaatttgc aaacatccac ccctttgtgc ctctggatca agctcaagga   1920
tatcagcagc ttttccgaga gcttgagaag gatttgtgtg aactcacagg ttatgaccag   1980
gtctgtttcc agccaaacag cggagcccag ggagaatatg ctggactggc cactatccga   2040
gcctacttaa accagaaagg agaggggcac agaacggttt gcctcattcc gaaatcagca   2100
catgggacca acccagcaag tgcccacatg gcaggcatga agattcagcc tgtggaggtg   2160
gataaatatg ggaatatcga tgcagttcac ctcaaggcca tggtggataa gcacaaggag   2220
aacctagcag ctatcatgat tacataccca tccaccaatg ggtgtttga agagaacatc   2280
agtgacgtgt gtgacctcat ccatcaacat ggaggacagg tctacctaga cggggcaaat   2340
atgaatgctc aggtgggaat ctgtcgccct ggagacttcg ggtctgatgt ctcgcaccta   2400
aatcttcaca agaccttctg cattccccac ggaggaggtg gtcctggcat ggggcccatc   2460
ggagtgaaga aacatctcgc ccgtttttg cccaatcatc ccgtcatttc actaaagcgg   2520
aatgaggatg cctgtcctgt gggaaccgtc agtgcggccc catggggctc cagttccatc   2580
ttgcccattt cctgggctta tatcaagatg atgggaggca agggtcttaa acaagccacg   2640
gaaactgcga tattaaatgc caactacatg gccaagcgat tagaaacaca ctacagaatt   2700
cttttcaggg gtgcaagagg ttatgtgggt catgaattta ttttggacac gagacccttc   2760
aaaaagtctg caaatattga ggctgtggat gtggccaaga gactccagga ttatggattt   2820
cacgccccta ccatgtcctg gcctgtggca gggaccctca tggtggagcc cactgagtcg   2880
gaggacaagg cagagctgga cagattctgt gatgccatga tcagcattcg gcaggaaatt   2940
gctgacattg aggagggccg catcgacccc agggtcaatc cgctgaagat gtctccacac   3000
tccctgacct gcgttacatc ttcccactgg gaccggcctt attccagaga ggtggcagca   3060
ttcccactcc ccttcatgaa accagagaac aaattctggc caacgattgc ccggattgat   3120
gacatatatg gagatcagca cctggtttgt acctgcccac ccatggaagt ttatgagtct   3180
ccattttctg aacaaaagag ggcgtcttct tagtcctctc tccctaagtt taaaggactg   3240
atttgatgcc tctccccaga gcatttgata agcaagaaag atttcatctc ccaccccagc   3300
ctcaagtagg agttttatat actgtgtata tctctgtaat ctctgtcaag gtaaatgtaa   3360
atacagtagc tggagggagt cgaagctgat ggttggaaga cggatttgct ttggtattct   3420
gcttccacat gtgccagttg cctggattgg gagccatttt gtgttttgcg tagaaagttt   3480
taggaacttt aacttttaat gtggcaagtt tgcagatgtc atagaggcta tcctggagac   3540
ttaatagaca tttttttgtt ccaaaagagt ccatgtggac tgtgccatct gtgggaaatc   3600
ccagggcaaa tgtttacatt ttgtataccc tgaagaactc tttttcctct aatatgccta   3660
atctgtaatc acatttctga gtgttttcct ctttttctgt gtgaggtttt tttttttttt   3720
aatctgcatt tattagtatt ctaataaaag cattttgatc gg                      3762
```

<210> SEQ ID NO 18
<211> LENGTH: 1192
<212> TYPE: DNA
<213> ORGANISM: Homo sapiens

<400> SEQUENCE: 18

```
ggctccctcc ggccgcgaac tgcccctccc cgccccgcct cccggcgcgg gtggccgagg     60

cgtagcgccg cgacccccgc acccctgcga acatggcgct gcgagtggtg cggagcgtgc    120

gggccctgct ctgcaccctg cgcgcggtcc cgttacccgc cgcgccctgc ccgccgaggc    180

cctggcagct gggggtgggc gccgtccgta cgctgcgcac tggacccgct ctgctctcgg    240

tgcgtaaatt cacagagaaa cacgaatggg taacaacaga aaatggcatt ggaacagtgg    300

gaatcagcaa ttttgcacag gaagcgttgg gagatgttgt ttattgtagt ctccctgaag    360

ttgggacaaa attgaacaaa caagatgagt ttggtgcttt ggaaagtgtg aaagctgcta    420

gtgaactata ttctccttta tcaggagaag taactgaaat taatgaagct cttgcagaaa    480

atccaggact tgtaaacaaa tcttgttatg aagatggttg gctgatcaag atgacactga    540

gtaacccttc agaactagat gaacttatga gtgaagaagc atatgagaaa tacataaaat    600

ctattgagga gtgaaaatgg aactcctaaa taaactagta tgaaataacg aagccagcag    660

agttgtctta aattagtggt ggatagagac ttagaataga aacttttagt attaccgatg    720

gggcaaaaaa aaactactgt taacactgct aatgaaagaa aatgcccttt aactttgtaa    780

tgattataga taaatataat atgcgtcttt ttcacaatat cctatgattt ttagactagg    840

ctctagtgtt cagaattcat gaaattatcc atggtaaaaa ctagttataa aaattacata    900

attcaaagat aacattgtta ttcttaagcc ttatataata ttgtaacttg catgtatcca    960

tacctggatt tgggatgaaa tacttaatga tctttccatt ggaaataact ggaagtgaag   1020

aggttttgtt gcttgtacag tgtcagatga ggaacaccac tatcttaatt ttgcgataca   1080

ctgcatttgc tggtgctatt tttatacagt gaagcaacag ctttgcagca aaataataaa   1140

atacttcttc gttaaaaaaa aaaaaaaaaa aaaaaaaaaa aaaaaaaaaa aa           1192
```

<210> SEQ ID NO 19
<211> LENGTH: 2102
<212> TYPE: DNA
<213> ORGANISM: Homo sapiens

<400> SEQUENCE: 19

```
tgcccacgcc cccttcagat cctttgctcc ggagagagac ctgtccgagc agaggcctgg     60

actacatctc ccggcgtgcc tggcagtgtg gtggcctctg tgcgccgtct gcactcgttg    120

caggcgacga tgcagagggc tgtaagtgtg gtggcccgtc tgggctttcg cctgcaggca    180

ttccccccgg ccttgtgtcg tccacttagt tgcgcacagg aggtgctccg caggacaccg    240

ctctatgact tccacctggc ccacggcggg aaaatggtgg cgtttgcggg ttggagtctg    300

ccagtgcagt accgggacag tcacactgac tcgcacctgc acacacgcca gcactgctcg    360

ctctttgacg tgtctcatat gctgcagacc aagatacttg gtagtgaccg ggtgaagctg    420

atggagagtc tagtggttgg agacattgca gagctaagac caaaccaggg gacactgtcg    480

ctgtttacca acgaggctgg aggcatctta gatgacttga ttgtaaccaa tacttctgag    540

ggccacctgt atgtggtgtc caacgctggc tgctgggaga aagatttggc cctcatgcag    600

gacaaggtca gggagcttca gaaccagggc agagatgtgg gcctggaggt gttggataat    660

gccctgctag ctctgcaagg ccccactgca gcccaggtac tacaggccgg cgtggcagat    720
```

```
gacctgagga aactgccctt catgaccagt gctgtgatgg aggtgtttgg cgtgtctggc    780

tgccgcgtga cccgctgtgg ctacacagga gaggatggtg tggagatctc ggtgccggta    840

gcgggggcag ttcacctggc aacagctatt ctgaaaaacc cagaggtgaa gctggcaggg    900

ctggcagcca gggacagcct gcgcctggag gcaggcctct gcctgtatgg gaatgacatt    960

gatgaacaca ctacacctgt ggagggcagc ctcagttgga cactggggaa gcgccgccga   1020

gctgctatgg acttccctgg agccaaggtc attgttcccc agctgaaggg cagggtgcag   1080

cggaggcgtg tggggttgat gtgtgagggg gcccccatgc gggcacacag tcccatcctg   1140

aacatggagg gtaccaagat tggtactgtg actagtggct gcccctcccc ctctctgaag   1200

aagaatgtgg cgatgggtta tgtgccctgc gagtacagtc gtccagggac aatgctgctg   1260

gtagaggtgc ggcggaagca gcagatggct gtagtcagca agatgccctt tgtgcccaca   1320

aactactata ccctcaagtg aagctggctc agggtggggc tgtcccttcc aggagttttg   1380

cccctacaag ggttagtca agaagctgag gcagaactca ctgggggtgg gcagttaagg   1440

tggaggctga ttctaattgt ctggttgagg ggccacacca cctattcccc ccacctaact   1500

catgccattc cagcttcctt caggaccctg cttctgagtg acggaccagc tcacacaatg   1560

tcttgtttca gtccatgatc ccactgacct actcttgcct gctggagggt aatgagaagc   1620

tttggttctg ccatctctcc cactctgcca ggtgctggct gtggagcaaa ggctcacctt   1680

tgtggagagg ataaaacctg cccaacctac ctcaccatgg tttttcacat tgcaaagggt   1740

aataacatgg gcagtgcgga cttaggctac cccctccagt ttgctttccg taaatgcaaa   1800

ttgtccttac tgcaagtcag gaatgattgc tgactcacag tagggctgct atgcctgtgt   1860

gtaaacttgg ggatggctga gggaacatag actcactctt ccacattccc aagttggtct   1920

agtgtgctgc ccagtagcaa accatggcag actcaccacc tattctgagt tccagggctg   1980

ctgtagggca gggtgggctt cctcccagac ttgccttacc ctgggctgat ctttgcccct   2040

ggtatgcatt aatggactcc actgaatcct gaaaaaaaaa ttaaacttcc ttcttacttg   2100

cc                                                                  2102
```

<210> SEQ ID NO 20
<211> LENGTH: 3228
<212> TYPE: DNA
<213> ORGANISM: Homo sapiens

<400> SEQUENCE: 20

```
aaaaaactca ggcaaagtca cagcctcaaa attgttcact gaaagaacgc tgagtggaga     60

agtgtgagaa gatgaatgga ccggtggatg gcttgtgtga ccactctcta agtgaaggag    120

tcttcatgtt cacatcggag tctgtgggag agggacaccc ggataagatc tgtgaccaga    180

tcagtgatgc agtgctggat gcccatctca agcaagaccc caatgccaag gtggcctgtg    240

agacagtgtg caagaccggc atggtgctgc tgtgtggtga gatcacctca atggccatgg    300

tggactacca gcgggtggtg agggacacca tcaagcacat cggctacgat gactcagcca    360

agggctttga cttcaagact tgcaacgtgc tggtggcttt ggagcagcaa tccccagata    420

ttgcccagtg cgtccatctg gacagaaatg aggaggatgt gggggcagga gatcagggtt    480

tgatgttcgg ctatgctacc gacgagacag aggagtgcat gcccctcacc atcatccttg    540

ctcacaagct caacgcccgg atggcagacc tcaggcgctc cggcctcctc ccctggctgc    600

ggcctgactc taagactcag gtgacagttc agtacatgca ggacaatggc gcagtcatcc    660

ctgtgcgcat ccacaccatc gtcatctctg tgcagcacaa cgaagacatc acgctggagg    720
```

-continued

```
agatgcgcag ggccctgaag gagcaagtca tcagggccgt ggtgccggcc aagtacctgg    780
acgaagacac cgtctaccac ctgcagccca gtgggcggtt tgtcatcgga ggtccccagg    840
gggatgcggg tgtcactggc cgtaagatta ttgtggacac ctatggcggc tggggggctc    900
atggtggtgg ggccttctct gggaaggact acaccaaggt agaccgctca gctgcatatg    960
ctgcccgctg ggtggccaag tctctggtga aagcagggct ctgccggaga gtgcttgtcc   1020
aggtttccta tgccattggt gtggccgagc cgctgtccat ttccatcttc acctacggaa   1080
cctctcagaa gacagagcga gagctgctgg atgtggtgca taagaacttc gacctccggc   1140
cgggcgtcat tgtcagggat ttggacttga agaagcccat ctaccagaag acagcatgct   1200
acggccattt cggaagaagc gagttcccat gggaggttcc caggaagctt gtattttaga   1260
gccaggggga gctgggcctg gtctcaccct ggaggcacct ggtggccatg ctcctcttcc   1320
ccagacgcct ggctgctgat cgccttcccc acccaccaac cctcagggca aagccaggtc   1380
cctctcattt agcctgtcct gtcatcatca tggccagctg gaggcagggg cttcctggtg   1440
ctggaggttg gatcttgatg taaggatggg catggtgttc tcctgctgct ccctcagact   1500
ggggcaatgt taatttagtg gaaaaggcac ccccgtcaag agtgaattcc ctcactcgtc   1560
tcccccaaca gctggaccct gaccagctcc ccctccctcc ccttgcctgt gccaggtgag   1620
gtcagcacat ctcaacaggc ctcagggctc cttgtgggcc tgggctcctg gacccccctt   1680
tcacaggcag ccagtgccct gagccagggt ctccagaaag ccccacccag gccaggcatg   1740
tggcaggggt tagagcagga ctgatgtctc ctaagcacct gtaatgtgcg agggacccag   1800
ctaataactg atctcgtttt ttcttcactg caacatgatg aggtagtacc ttttatatcc   1860
catttataga tgggggaaag caaagcacag agagtctgga taacttccac agggtcccac   1920
agccacgtgt ttagacctag atgtataact aggagctttg actcaggagc ctgtgacata   1980
ccccttccc caccgttgtc tcatgccagt aacaggctca aacaatgaca aagcagattc    2040
agaaatgagg ccatggactc tgtcctgaag gcctgaggtt actggaaatt aggggattaa   2100
cccactagct cttgttgagc cgtgggcaat tgtctgaaaa gtgaagacag aaccacaggg   2160
ctattttgtt tgcttcatgt gtcccagaag atgactgagg gtgagttggc ttacctggcc   2220
catcagggta ggctggagtt agggactgac cagcagcttt agaatcccag ccccctgacc   2280
actcagagac atgcagagat tgggtttttg gacttctggg gtaagtggtc taagtccagt   2340
ccagtcctat gtgggcttcc tggagcagaa gcagcaactt gtcctagcac agatggccag   2400
ccccttagac agaggccctc aagtctttct ctttccctgg tcccttgtat cccctgcagg   2460
ctgagtgcat ttggagggag tgagtggccc tttcggatcc agggaggctg gtcctatggc   2520
ctcatgttaa ataggcgggg cttgccttct ggtgttggac aagcttctga gacgtcatga   2580
ggagattctg cctttgccag gtgactgtct ggggagcggg tctgctccca aggggcctga   2640
gcagtccttg gcctgctaag gtcttggaac ttgcctgcct ttccatccat ggccagcagc   2700
acctgcccta cctgccccac ttgtccttag cctggacctc tgacagcagc atctctacct   2760
tctccccagc tcccaggacc acaggctcag gcagggcctc catgggcccc aggggaacac   2820
tggggacttg gcctctctct agggtacatg gtgctgggag aggcagccca ggaagtctca   2880
tctggggagc aggcagccag catctgggcc ttggcctgga gcacaaagac cctggctttc   2940
attttctctc aggtgaaagg aaattaaggc aacaaaagaa gcccggctcc tggtcaccta   3000
ggaagcctca gattccttcc catggaggga gggagtggtt tgcaggtggc caagttcctc   3060
```

-continued

```
taacttggct cacactcgac atgaaaattc agaattttat actttcccta ccctctagag   3120

aaataagatc ttttttgtca gtttgtttgt atgaaactaa agctttattt gttaatagtt   3180

cctgctaaaa caatgaataa aaactcaagg agcaactaaa aaaaaaa                 3228


<210> SEQ ID NO 21
<211> LENGTH: 344
<212> TYPE: PRT
<213> ORGANISM: Homo sapiens

<400> SEQUENCE: 21

Met Ser Ala Leu Ala Ala Arg Leu Leu Gln Pro Ala His Ser Cys Ser
  1               5                  10                  15

Leu Arg Leu Arg Pro Phe His Leu Ala Ala Val Arg Asn Glu Ala Val
             20                  25                  30

Val Ile Ser Gly Arg Lys Leu Ala Gln Gln Ile Lys Gln Glu Val Arg
         35                  40                  45

Gln Glu Val Glu Glu Trp Val Ala Ser Gly Asn Lys Arg Pro His Leu
     50                  55                  60

Ser Val Ile Leu Val Gly Glu Asn Pro Ala Ser His Ser Tyr Val Leu
 65                  70                  75                  80

Asn Lys Thr Arg Ala Ala Ala Val Val Gly Ile Asn Ser Glu Thr Ile
                 85                  90                  95

Met Lys Pro Ala Ser Ile Ser Glu Glu Glu Leu Leu Asn Leu Ile Asn
            100                 105                 110

Lys Leu Asn Asn Asp Asp Asn Val Asp Gly Leu Leu Val Gln Leu Pro
        115                 120                 125

Leu Pro Glu His Ile Asp Glu Arg Arg Ile Cys Asn Ala Val Ser Pro
    130                 135                 140

Asp Lys Asp Val Asp Gly Phe His Val Ile Asn Val Gly Arg Met Cys
145                 150                 155                 160

Leu Asp Gln Tyr Ser Met Leu Pro Ala Thr Pro Trp Gly Val Trp Glu
                165                 170                 175

Ile Ile Lys Arg Thr Gly Ile Pro Thr Leu Gly Lys Asn Val Val Val
            180                 185                 190

Ala Gly Arg Ser Lys Asn Val Gly Met Pro Ile Ala Met Leu Leu His
        195                 200                 205

Thr Asp Gly Ala His Glu Arg Pro Gly Gly Asp Ala Thr Val Thr Ile
    210                 215                 220

Ser His Arg Tyr Thr Pro Lys Glu Gln Leu Lys Lys His Thr Ile Leu
225                 230                 235                 240

Ala Asp Ile Val Ile Ser Ala Ala Gly Ile Pro Asn Leu Ile Thr Ala
                245                 250                 255

Asp Met Ile Lys Glu Gly Ala Ala Val Ile Asp Val Gly Ile Asn Arg
            260                 265                 270

Val His Asp Pro Val Thr Ala Lys Pro Lys Leu Val Gly Asp Val Asp
        275                 280                 285

Phe Glu Gly Val Arg Gln Lys Ala Gly Tyr Ile Thr Pro Val Pro Gly
    290                 295                 300

Gly Val Gly Pro Met Thr Val Ala Met Leu Met Lys Asn Thr Ile Ile
305                 310                 315                 320

Ala Ala Lys Lys Val Leu Arg Leu Glu Glu Arg Glu Val Leu Lys Ser
                325                 330                 335

Lys Glu Leu Gly Val Ala Thr Asn
            340
```

<210> SEQ ID NO 22
<211> LENGTH: 1283
<212> TYPE: DNA
<213> ORGANISM: Homo sapiens

<400> SEQUENCE: 22
tttcgcagcc gctgccgcct cgccgctgct ccttcgtaag gccacttccg cacaccgaca 60
ccaacatgaa cggacagctc aacggcttcc acgaggcgtt catcgaggag ggcacattcc 120
ttttcacctc agagtcggtc ggggaaggcc acccagataa gatttgtgac caaatcagtg 180
atgctgtcct tgatgcccac cttcagcagg atcctgatgc caaagtagct tgtgaaactg 240
ttgctaaaac tggaatgatc cttcttgctg gggaaattac atccagagct gctgttgact 300
accagaaagt ggttcgtgaa gctgttaaac acattggata tgatgattct tccaaaggtt 360
ttgactacaa gacttgtaac gtgctggtag ccttggagca acagtcacca gatattgctc 420
aaggtgttca tcttgacaga aatgaagaag acattggtgc tggagaccag ggcttaatgt 480
ttggctatgc cactgatgaa actgaggagt gtatgccttt aaccattgtc ttggcacaca 540
agctaaatgc caaactggca gaactacgcc gtaatggcac tttgccttgg ttacgccctg 600
attctaaaac tcaagttact gtgcagtata tgcaggatcg aggtgctgtg cttcccatca 660
gagtccacac aattgttata tctgttcagc atgatgaaga ggtttgtctt gatgaaatga 720
gggatgccct aaaggagaaa gtcatcaaag cagttgtgcc tgcgaaatac cttgatgagg 780
atacaatcta ccacctacag ccaagtggca gatttgttat tggtgggcct cagggtgatg 840
ctggtttgac tggacggaaa atcattgtgg acacttatgg cggttggggt gctcatggag 900
gaggtgcctt ttcaggaaag gattatacca aggtcgaccg ttcagctgct tatgctgctc 960
gttgggtggc aaaatccctt gttaaaggag gtctgtgccg gagggttctt gttcaggtct 1020
cttatgctat tggagtttct catccattat ctatctccat tttccattat ggtacctctc 1080
agaagagtga gagagagcta ttagagattg tgaagaagaa tttcgatctc cgccctgggg 1140
tcattgtcag ggatctggat ctgaagaagc caatttatca gaggactgca gcctatggcc 1200
actttggtag ggacagcttc ccatgggaag tgcccaaaaa gcttaaatat tgaaagtgtt 1260
agcctttttt ccccagactt gtt 1283

<210> SEQ ID NO 23
<211> LENGTH: 3259
<212> TYPE: DNA
<213> ORGANISM: Homo sapiens

<400> SEQUENCE: 23
caaggttggt ggaagtcgcg ttgtgcaggt tcgtgcccgg ctggcgcggc gtggtttcac 60
tgttacatgc cttgaagtga tgaggaggtt tctgttacta tatgctacac agcagggaca 120
ggcaaaggcc atcgcagaag aaatgtgtga gcaagctgtg gtacatggat tttctgcaga 180
tcttcactgt attagtgaat ccgataagta tgacctaaaa accgaaacag ctcctcttgt 240
tgttgtggtt tctaccacgg gcaccggaga cccacccgac acagcccgca agtttgttaa 300
ggaaatacag aaccaaacac tgccggttga tttctttgct cacctgcggt atgggttact 360
gggtctcggt gattcagaat acacctactt ttgcaatggg gggaagataa ttgataaacg 420
acttcaagag cttggagccc ggcatttcta tgacactgga catgcagatg actgtgtagg 480
tttagaactt gtggttgagc cgtggattgc tggactctgg ccagccctca gaaagcattt 540

-continued

```
taggtcaagc agaggacaag aggagataag tggcgcactc ccggtggcat cacctgcatc    600
cttgaggaca gaccttgtga agtcagagct gctacacatt gaatctcaag tcgagcttct    660
gagattcgat gattcaggaa gaaaggattc tgaggttttg aagcaaaatg cagtgaacag    720
caaccaatcc aatgttgtaa ttgaagactt tgagtcctca cttacccgtt cggtaccccc    780
actctcacaa gcctctctga atattcctgg tttacccccca gaatatttac aggtacatct    840
gcaggagtct cttggccagg aggaaagcca agtatctgtg acttcagcag atccagtttt    900
tcaagtgcca atttcaaagg cagttcaact tactacgaat gatgccataa aaaccactct    960
gctggtagaa ttggacattt caaatacaga cttttcctat cagcctggag atgccttcag   1020
cgtgatctgc cctaacagtg attctgaggt acaaagccta ctccaaagac tgcagcttga   1080
agataaaaga gagcactgcg tccttttgaa aataaaggca gacacaaaga agaaaggagc   1140
taccttaccc cagcatatac ctgcgggatg ttctctccag ttcattttta cctggtgtct   1200
tgaaatccga gcaattccta aaaaggcatt tttgcgagcc cttgtggact ataccagtga   1260
cagtgctgaa aagcgcaggc tacaggagct gtgcagtaaa caaggggcag ccgattatag   1320
ccgctttgta cgagatgcct gtgcctgctt gttggatctc ctcctcgctt tcccttcttg   1380
ccagccacca ctcagtctcc tgctcgaaca tcttcctaaa cttcaaccca gaccatattc   1440
gtgtgcaagc tcaagtttat ttcacccagg aaagctccat tttgtcttca acattgtgga   1500
atttctgtct actgccacaa cagaggttct gcggaaggga gtatgtacag gctggctggc   1560
cttgttggtt gcttcagttc ttcagccaaa catacatgca tcccatgaag acagcgggaa   1620
agccctggct cctaagatat ccatctctcc tcgaacaaca aattctttcc acttaccaga   1680
tgacccctca atccccatca taatggtggg tccaggaacc ggcatagccc cgtttattgg   1740
gttcctacaa catagagaga aactccaaga acaacaccca gatggaaatt ttggagcaat   1800
gtggttgttt tttggctgca ggcataagga tagggattat ctattcagaa aagagctcag   1860
acatttcctt aagcatggga tcttaactca tctaaaggtt tccttctcaa gagatgctcc   1920
tgttggggag gaggaagccc cagcaaagta tgtacaagac aacatccagc ttcatggcca   1980
gcaggtggcg agaatcctcc tccaggagaa cggccatatt tatgtgtgtg gagatgcaaa   2040
gaatatggcc aaggatgtac atgatgccct tgtgcaaata ataagcaaag aggttggagt   2100
tgaaaaacta gaagcaatga aaccctggc cactttaaaa gaagaaaaac gctaccttca   2160
ggatatttgg tcataaaacc agaaattaaa gaaagaggat taagcttttt tgactgaaag   2220
tactaaaagt cagctttact agtgccaaac ctttaaattt tcaaaagaaa attttctttc   2280
aacatttctt gaaggacatg gagtggagat tggatcattt aacaatataa caaaacttcc   2340
tgatttgatt ttacgtatct tctatctacg cccttcctgt gcctgtgact ctccccaaat   2400
tgccctgttg ccttgagctc ttctgagcta aaggcagcct tcagtcccta tcagcgcctc   2460
ctttacttcc cagagaactt cacagagact ctgtccttcc atgcaaaggc ttcctgaaat   2520
aggggagact gactgagtag ctcattcttg tgacttacag tgccaacatt taaaaaagta   2580
tgaaaatgat ttattttttat atgatgtata cccataaaga atgctcatat taatgtactt   2640
aaattacaca tgtagagcat atctgttata tgtttatgta actatcaaat ggttatttgt   2700
tactaaagct atatttctga taaaaaatat tttaggataa ttgcctacag agggatttat   2760
ttttatgatg ctgggaaata tgaaatgtat tttaaaattt cactctgggc atatggattt   2820
atctatcacc attacttttt tttaagtcac aatttcagaa ttttgggaca tttgcattca   2880
atttacaggt accagtacgt acatatttta atagaaagat acaacctttt tattttcact   2940
```

```
cctttattt ctgctgcttg gcacattttt gagttttccc acattatttg tctccatgat   3000
accactcaag cagtgtgctg gacctaaaat actgacttta gttagtatcc ttggattttt   3060
agattcccca gtgtctaatt ccctgttata atttgcacaa acaaaacaaa atgttatgat   3120
aatctttctc cactgttcta atatatattg tatttttatt tgatagcttg ggatttaaaa   3180
catctctgtt gaaggctttt gatccttttg agaaataaag atctgaaaga aatggcataa   3240
tcttaaaaaa aaaaaaaaa                                                3259

<210> SEQ ID NO 24
<211> LENGTH: 1805
<212> TYPE: DNA
<213> ORGANISM: Homo sapiens

<400> SEQUENCE: 24

aagagactga actgtatctg cctctatttc caaaagactc acgttcaact ttcgctcaca     60
caaagccggg aaaattttat tagtcctttt tttaaaaaaa gttaatataa aattatagca    120
aaaaaaaaaa ggaacctgaa ctttagtaac acagctggaa caatcgcagc ggcggcggca    180
gcggcgggag aagaggttta atttagttga ttttctgtgg ttgttggttg ttcgctagtc    240
tcacggtgat ggaagctgca catttttttcg aagggaccga gaagctgctg gaggtttggt    300
tctcccggca gcagcccgac gcaaaccaag gatctgggga tcttcgcact atcccaagat    360
ctgagtggga catacttttg aaggatgtgc aatgttcaat cataagtgtg acaaaaactg    420
acaagcagga agcttatgta ctcagtgaga gtagcatgtt tgtctccaag agacgtttca    480
ttttgaagac atgtggtacc accctcttgc tgaaagcact ggttcccctg ttgaagcttg    540
ctagggatta cagtgggttt gactcaattc aaagcttctt ttattctcgt aagaatttca    600
tgaagccttc tcaccaaggg tacccacacc ggaatttcca ggaagaaata gagtttctta    660
atgcaatttt cccaaatgga gcaggatatt gtatgggacg tatgaattct gactgttggt    720
acttatatac tctggatttc ccagagagtc gggtaatcag tcagccagat caaaccttgg    780
aaattctgat gagtgagctt gacccagcag ttatggacca gttctacatg aaagatggtg    840
ttactgcaaa ggatgtcact cgtgagagtg gaattcgtga cctgatacca ggttctgtca    900
ttgatgccac aatgttcaat ccttgtgggt attcgatgaa tggaatgaaa tcggatggaa    960
cttattggac tattcacatc actccagaac cagaattttc ttatgttagc tttgaaacaa   1020
acttaagtca gacctcctat gatgacctga tcaggaaagt tgtagaagtc ttcaagccag   1080
gaaaatttgt gaccaccttg tttgttaatc agagttctaa atgtcgcaca gtgcttgctt   1140
cgccccagaa gattgaaggt tttaagcgtc ttgattgcca gagtgctatg ttcaatgatt   1200
acaattttgt ttttaccagt tttgctaaga agcagcaaca acagcagagt tgattaagaa   1260
aaatgaagaa aaaacgcaaa aagagaacac atgtagaagg tggtggatgc tttctagatg   1320
tcgatgctgg gggcagtgct ttccataacc accactgtgt agttgcagaa agccctagat   1380
gtaatgatag tgtaatcatt ttgaattgta tgcattatta tatcaaggag ttagatatct   1440
tgcatgaatg ctctcttctg tgtttaggta ttctctgcca ctcttgctgt gaaattgaag   1500
tggatgtaga aaaaaccttt tactatatga aactttacaa cacttgtgaa agcaactcaa   1560
tttggtttat gcacagtgta atatttctcc aagtatcatc caaaattccc cacagacaag   1620
gctttcgtcc tcattaggtg ttggcctcag cctaaccctc taggactgtt ctattaaatt   1680
gctgccagaa ttttacatcc agttacctcc actttctaga acatattctt tactaatgtt   1740
```

-continued

```
attgaaacca atttctactt catactgatg tttttggaaa cagcaattaa agtttttctt   1800

ccatg                                                                1805


<210> SEQ ID NO 25
<211> LENGTH: 254
<212> TYPE: PRT
<213> ORGANISM: Homo sapiens

<400> SEQUENCE: 25

Gln Asp Ile Leu Val Phe Arg Ser Lys Thr Tyr Gly Asn Val Leu Val
  1               5                  10                  15

Leu Asp Gly Val Ile Gln Cys Thr Glu Arg Asp Glu Phe Ser Tyr Gln
             20                  25                  30

Glu Met Ile Ala Asn Leu Pro Leu Cys Ser His Pro Asn Pro Arg Lys
         35                  40                  45

Val Leu Ile Ile Gly Gly Gly Asp Gly Gly Val Leu Arg Glu Val Val
     50                  55                  60

Lys His Pro Ser Val Glu Ser Val Val Gln Cys Glu Ile Asp Glu Asp
 65                  70                  75                  80

Val Ile Gln Val Ser Lys Lys Phe Leu Pro Gly Met Ala Ile Gly Tyr
                 85                  90                  95

Ser Ser Ser Lys Leu Thr Leu His Val Gly Asp Gly Phe Glu Phe Met
            100                 105                 110

Lys Gln Asn Gln Asp Ala Phe Asp Val Ile Ile Thr Asp Ser Ser Asp
        115                 120                 125

Pro Met Gly Pro Ala Glu Ser Leu Phe Lys Glu Ser Tyr Tyr Gln Leu
    130                 135                 140

Met Lys Thr Ala Leu Lys Glu Asp Gly Val Leu Cys Cys Gln Gly Glu
145                 150                 155                 160

Cys Gln Trp Leu His Leu Asp Leu Ile Lys Glu Met Arg Gln Phe Cys
                165                 170                 175

Gln Ser Leu Phe Pro Val Val Ala Tyr Ala Tyr Cys Thr Ile Pro Thr
            180                 185                 190

Tyr Pro Ser Gly Gln Ile Gly Phe Met Leu Cys Ser Lys Asn Pro Ser
        195                 200                 205

Thr Asn Phe Gln Glu Pro Val Gln Pro Leu Thr Gln Gln Gln Val Ala
    210                 215                 220

Gln Met Gln Leu Lys Tyr Tyr Asn Ser Asp Val His Arg Ala Ala Phe
225                 230                 235                 240

Val Leu Pro Glu Phe Ala Arg Lys Ala Leu Asn Asp Val Ser
                245                 250


<210> SEQ ID NO 26
<211> LENGTH: 2211
<212> TYPE: DNA
<213> ORGANISM: Homo sapiens

<400> SEQUENCE: 26

ctgaggccca gccccccttcg cccgtttcca tcacgagtgc cgccagcatg tctgacaaac     60

tgccctacaa agtcgccgac atcggcctgg ctgcctgggg acgcaaggcc ctggacattg    120

ctgagaacga gatgccgggc ctgatgcgta tgcgggagcg gtactcggcc tccaagccac    180

tgaagggcgc ccgcatcgct ggctgcctgc acatgaccgt ggagacggcc gtcctcattg    240

agaccctcgt caccctgggt gctgaggtgc agtggtccag ctgcaacatc ttctccaccc    300

agaaccatgc ggcggctgcc attgccaagg ctggcattcc ggtgtatgcc tggaagggcg    360
```

```
aaacggacga ggagtacctg tggtgcattg agcagaccct gtacttcaag gacgggcccc    420

tcaacatgat tctggacgac gggggcgacc tcaccaacct catccacacc aagtacccgc    480

agcttctgcc aggcatccga ggcatctctg aggagaccac gactggggtc cacaacctct    540

acaagatgat ggccaatggg atcctcaagg tgcctgccat caatgtcaat gactccgtca    600

ccaagagcaa gtttgacaac ctctatggct gccgggagtc cctcatagat ggcatcaagc    660

gggccacaga tgtgatgatt gccggcaagg tagcggtggt agcaggctat ggtgatgtgg    720

gcaagggctg tgcccaggcc ctgcggggtt tcggagcccg cgtcatcatc accgagattg    780

accccatcaa cgcactgcag gctgccatgg agggctatga ggtgaccacc atggatgagg    840

cctgtcagga gggcaacatc tttgtcacca ccacaggctg tattgacatc atccttggcc    900

ggtaggtgcc agatgggggg tcccggggag tgagggagga gggcagagtt gggacagctt    960

tctgtccctg acaatctccc acggtcttgg gctgcctgac aggcactttg agcagatgaa   1020

ggatgatgcc attgtgtgta acattggaca ctttgacgtg gagatcgatg tcaagtggct   1080

caacgagaac gccgtggaga aggtgaacat caagccgcag gtggaccggt atcggttgaa   1140

gaatgggcgc cgcatcatcc tgctggccga gggtcggctg gtcaacctgg gttgtgccat   1200

gggccacccc agcttcgtga tgagtaactc cttcaccaac caggtgatgg cgcagatcga   1260

gctgtggacc catccagaca agtaccccgt tggggttcat ttcctgccca agaagctgga   1320

tgaggcagtg gctgaagccc acctgggcaa gctgaatgtg aagttgacca agctaactga   1380

gaagcaagcc cagtacctgg gcatgtcctg tgatggcccc ttcaagccgg atcactaccg   1440

ctactgagag ccaggtctgc gtttcaccct ccagctgctg tccttgccca ggccccacct   1500

ctcctcccta agagctaatg gcaccaactt tgtgattggt ttgtcagtgt cccccatcga   1560

ctctctgggg ctgatcactt agtttttggc ctctgctgca gccgtcatac tgttccaaat   1620

gtggcagcgg gaacagagta ccctcttcaa gccccggtca tgatggaggt cccagccaca   1680

gggaaccatg agctcagtgg tcttggaaca gctcactaag tcagtccttc cttagcctgg   1740

aagtcagtag tggagtcaca aagcccatgt gttttgccat ctaggccttc acctggtctg   1800

tggacttata cctgtgtgct tggtttacag gtccagtggt tcttcagccc atgacagatg   1860

agaaggggct atattgaagg gcaaagagga actgttgttt gaattttcct gagagcctgg   1920

cttagtgctg ggccttctct taaacctcat tacaatgagg ttagtacttt tagtccctgt   1980

tttacagggg ttagaataga ctgttaaggg gcaactgaga aagaacagag aagtgacagc   2040

taggggttga gaggggccag aaaaacatga atgcaggcag atttcgtgaa atctgccacc   2100

actttataac cagatggttc ctttcacaac cctgggtcaa aaagagaata atttggccta   2160

taatgttaaa agaaagcagg aaggtgggta aataaaaatc ttggtgcctg g            2211
```

<210> SEQ ID NO 27
<211> LENGTH: 2436
<212> TYPE: DNA
<213> ORGANISM: Homo sapiens

<400> SEQUENCE: 27

```
cgaccacctg tctggacacc acaaagatgc cacccgttgg gggcaaaaag gccaagaagg     60

gcatcctaga acgtttaaat gctggagaga ttgtgattgg agatggaggg tttgtctttg    120

cactggagaa gaggggctac gtaaaggcag gaccctggac tcctgaagct gctgtggagc    180

acccagaagc agttcgccag cttcatcgag agttcctcag agctggctca aacgtcatgc    240
```

-continued

```
agaccttcac cttctatgcg agtgaagaca agctggagaa caggggcaac tatgtcttag    300
agaagatatc tgggcaggaa gtcaatgaag ctgcttgcga catcgcccga caagtggctg    360
atgaaggaga tgctttggta gcaggaggag tgagtcagac accttcatac cttagctgca    420
agagtgaaac tgaagtcaaa aaagtatttc tgcaacagtt agaggtcttt atgaagaaga    480
acgtggactt cttgattgca gagtattttg aacacgttga agaagctgtg tgggcagttg    540
aaaccttgat agcatccggt aaacctgtgg cagcaaccat gtgcattggc ccagaaggag    600
atttgcatgg cgtgcccccc ggcgagtgtg cagtgcgcct ggtgaaagca ggagcatcca    660
tcattggtgt gaactgccac tttgacccca ccattagttt aaaaacagtg aagctcatga    720
aggagggctt ggaggctgcc caactgaaag ctcacctgat gagccagccc ttggcttacc    780
acactcctga ctgcaacaag cagggattca tcgatctccc agaattccca tttggactgg    840
aacccagagt tgccaccaga tgggatattc aaaaatacgc cagagaggcc tacaacctgg    900
gggtcaggta cattggcggg tgctgtggat ttgagcccta ccacatcagg gcaattgcag    960
aggagctggc cccagaaagg ggctttttgc caccagcttc agaaaaacat ggcagctggg   1020
gaagtggttt ggacatgcac accaaaccct gggttagagc aagggccagg aaggaatact   1080
gggagaatct tcggatagcc tcaggccggc catacaaccc ttcaatgtca aagccagatg   1140
gctggggagt gaccaaagga acagccgagc tgatgcagca gaaagaagcc acaactgagc   1200
agcagctgaa agagctcttt gaaaaacaaa aattcaaatc acagtagcct cgatagaagc   1260
tatttttgat gaatttctag gtgtttgggt cacagttcct acaaatacgg aaaagggggt   1320
taaaaagcag tgctttcatg aatgccatcc tacacatatt attgctatta cctgaacaaa   1380
atagaattac aaatagcact tgataatttt aaagtatgtt ttagaaattt tcttaggagc   1440
aaaataagta caaagtaaat cttgaacagg ttcactaagc acccaccctg tgaaaagtat   1500
tatggaaatc actgcagcac aggaaaagta attcagatgt taatgccact tgaagaagtt   1560
ggtaggctag caaagaggat gagacatgaa ctgtcataaa ggactcagca accagccagg   1620
gacagataaa gcgctatgga aaggggcttc caagttcttt tgaacatgac ccttagtaac   1680
aaacacaatt tatataatga cccagcaaaa cacatcacat cttactgtcg aaattaaatg   1740
tgtgatccat cctagtattt tctgttccat tccttttcat tctatttcat ttataaaaca   1800
tgctagttga gacttttcaa atggattttt atgacccact actgggtttg gatccacagt   1860
ttgaaaaata ttgctacaag acacttaagg agaccatcct gtttaagttt attcttataa   1920
gtaggtcagt catatgagac ctgatcaata aatatccaat acccagagtc ctgctctcag   1980
agttcttctg tttcgtgacc cacttttcta ccagtaaaag acatagacca atggggagga   2040
ggggaggaga gatggatatt tcagccctct ccatcctagt caacactgga tccacctagt   2100
gcctctgggc cataaggctg agcagagtga gcttgtatta gttggtagct tttaaaaaat   2160
ataataaaaa aaaagtagag attctccaaa ctctagcctg gtttcctaga ttgagaacta   2220
tgatattttt ctctgataat ttaatatcta ctctcctaca aaagctcaag cctgaagata   2280
caagactatt agaagaaaca tgactaccct cagtgtatta gaaaagaggt catgcagctt   2340
tctaaacatt attgaattgt ttgagctgtt ttgaaattgt aattcttttc agctattaaa   2400
aagaagagca atgagaaaaa aaaaaaaaaa aaaaaa                              2436
```

<210> SEQ ID NO 28
<211> LENGTH: 1326
<212> TYPE: DNA
<213> ORGANISM: Homo sapiens

<400> SEQUENCE: 28

```
ttcttttcct ctcttcttct ttcgcggttc agcatgcagg aaaaagacgc ctcctcacaa     60

ggtttcctgc cacacttcca acatttcgcc acgcaggcga tccatgtggg ccaggatccg    120

gagcaatgga cctccagggc tgtagtgccc cccatctcac tgtccaccac gttcaagcaa    180

ggggcgcctg gccagcactc gggttttgaa tatagccgtt ctggaaatcc cactaggaat    240

tgccttgaaa aagcagtggc agcactggat ggggctaagt actgtttggc ctttgcttca    300

ggtttagcag ccactgtaac tattacccat cttttaaaag caggagacca aattatttgt    360

atggatgatg tgtatggagg tacaaacagg tacttcaggc aagtggcatc tgaatttgga    420

ttaaagattt cttttgttga ttgttccaaa atcaaattac tagaggcagc aattacacca    480

gaaaccaagc ttgtttggat cgaaaccccc acaaacccca cccagaaggt gattgacatt    540

gaaggctgtg cacatattgt ccataagcat ggagacatta ttttggtcgt ggataacact    600

tttatgtcac catatttcca gcgccctttg gctctgggag ctgatatttc tatgtattct    660

gcaacaaaat acatgaatgg ccacagtgat gttgtaatgg gcctggtgtc tgttaattgt    720

gaaagccttc ataatagact tcgtttcttg caaaactctc ttggagcagt tccatctcct    780

attgattgtt acctctgcaa tcgaggtctg aagactctac atgtccgaat ggaaaagcat    840

ttcaaaaacg gaatggcagt tgcccagttc ctggaatcta atccttgggt agaaaaggtt    900

atttatcctg ggctgccctc tcatccacag catgagttgg tgaagcgtca gtgtacaggt    960

tgtacaggga tggtcacctt ttatattaag ggcactcttc agcatgctga gattttcctc   1020

aagaacctaa agctatttac tctggccgag agcttgggag gattcgaaag ccttgctgag   1080

cttccggcaa tcatgactca tgcatcagtt cttaagaatg acagagatgt ccttggaatt   1140

agtgacacac tgattcgact ttctgtgggc ttagaggatg aggaagacct actggaagat   1200

ctagatcaag ctttgaaggc agcacaccct ccaagtggaa ttcacagcta gtattccaga   1260

gctgctatta gaagctgctt cctgtgaaga tcaatcttcc tgagtaatta atggaccaac   1320

aatgag                                                              1326
```

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence:PCR product

<400> SEQUENCE: 29

```
cccacggtcg ggtacctgg gcgggacgcg ccaggccgac tcccggcga                 49
```

<210> SEQ ID NO 30
<211> LENGTH: 3464
<212> TYPE: DNA
<213> ORGANISM: Homo sapiens

<400> SEQUENCE: 30

```
tttaatggac acataattta attatatatt ttttcttaca gatacccagg tgttctctct     60

gatgtccagg aggagaaagg cattaagtac aaatttgaag tatatgagaa gaatgattaa    120

tatgaaggtg ttttctagtt taagttgttc cccctccctc tgaaaaaagt atgtattttt    180

acattagaaa aggtttttttg ttgactttag atctataatt atttctaagc aactagtttt    240

tattccccac tactcttgtc tctatcagat accatttatg agacattctt gctataacta    300
```

-continued

```
agtgcttctc caagacccca actgagtccc cagcacctgc tacagtgagc tgccattcca    360
cacccatcac atgtggcact cttgccagtc cttgacattg tcgggctttt cacatgttgg    420
taatatttat taaagatgaa gatccacata cccttcaact gagcagtttc actagtggaa    480
ataccaaaag cttcctacgt gtatatccag aggtttgtag ataaatgttg ccaccttgtt    540
tgtaacagtg aaaaattgaa aacaacctgg aagtccagtg atgggaaaat gagtatgttt    600
ctgtcttaga ttggggaacc caaagcagat tgcaagactg aaatttcagt gaaagcagtg    660
tatttgctag gtcataccag aaatcatcaa ttgaggtacg gagaaactga actgagaagg    720
taagaaaagc aatttaaagt cagcgagcag gttctcattg ataacaagct ccatactgct    780
gagatacagg gaaatggagg ggggaaagct ggagtattga tcccgccccc ctccttggtt    840
gtcagctccc tgtcctgtgt gtgggcggaa catagtccag ctgctctata gcaagtctca    900
ggtgtttgca gtaagaagct gctggcatgc acgggaacag tgaatgccaa acacttaaag    960
caattcgatg tttaagtatg taagttcttt ttttttaga cagcgtttcg ctcttgttgc    1020
ccaggctagc atgcaatggt gtgacctcgg cttactgcaa cctccgcctt cccagattca   1080
agcgattctc ctgcctcagg ctcccaagta gctaggacca ggtgcgcgcc accacgcccg   1140
gctaattttt gtattttgta tttttagtag agatggggtt tcaccatgtt ggtcaggcta   1200
gtctcgaact cgtgaccgca agcgattcac ccacctcagc ctcccaaagt gctgggatta   1260
ccggcttgag ccaccacacc cggcacatct tcattctttt tatgtagtaa aaagtataag   1320
gccacacatg gtttatttga agtattttat aatttaaaaa aatacagaag caggaaaacc   1380
aattataagt tcaagtgagg gatgatggtt gcttgaacca aagggttgca tgtagtaaga   1440
aattgtgatt taagatatat tttaaagtta taagtagcag gatattctga tggagtttga   1500
ctttggtttt gggcccaggg agtttcagat gcctttgaga aatgaatgaa gtagagagaa   1560
aataaaagaa aaaccagcca ggcacagtgg ctcacacctg taatcccagc gctttgggag   1620
gctaaggcag gcagatcact tgagaccagc ttgggcaaca tggcaaagcc ccatctctac   1680
aaaaaacaca aaaattagct gggcattgtg gcgcacacct gtattcccat ctagtcagga   1740
agctgagatg gaagaattaa ttgagcccac gagttcaagg ctgcagtgag tcgtgattgt   1800
gccactgcac tccagccggg gtgacagaag agaccttgtc tcgaaaacga atctgaaaac   1860
aatggaacca tgccttcata attctagaaa gttattttca actgataaat ctatattcac   1920
ccaaataatc aagggtgaag gtaaaataat acatttttag acaagcaaag actcaggggt   1980
tacctccatg tgcccttttt agggaagctg ttggagaaaa tactccagca aaatgaagga   2040
gtacacaaac cagagaatga catgaatcca gcaaatagga tccaacacag gcaatattcc   2100
agctatggag ctagctttaa aaaggaacag taaaaatatt aatcggttag ctgggtggaa   2160
tggcccatgc ctgtagtccc agctactcag gaggctcagc agcaggacga cttgagccca   2220
agagttccag accagcctgg ccaccttagt gagatccctt ctcttaaaaa taataactta   2280
ttgccagatt tggggcattt ggaaagaagt tcattgaaga taaagcaaaa gtaaaaaaaa   2340
aaaaaaaaaa aacaagggga aagggttggt taggcaatca ttctagggca gaaagaagta   2400
caggatagga agagcataat acactgtttt tctcaacaag gagcagtatg tacacagtca   2460
taatgatgtg actgcttagc cctaaatat ggtaactact ctgggacaat atgggaggaa    2520
aagtgaagat tgtgatggtg taagagctaa tcctcatctg tcatatccag aaatcactat   2580
ataatatata ataatgaaat gactaagtta tgtgaggaaa aaaacagaag acattgctaa   2640
aagagttaaa agtcattgct ctggagaatt aggagggatg gggcagggga ctgttaggat   2700
```

-continued

```
gcattataaa ctgaaaagcc tttttaaaat tttatgtatt aatatatgca ttcacttgaa   2760
aaactaaaaa aaaacaataa tttggaaaaa cccatgaagg taactaacgg aaggaaaaac   2820
taagagaatg aaaagtattt gcctctggaa agaacaactg gcaggactgt tgttttcatt   2880
gtaagacttt tggagccatt taattgtact taaccatttt catctatttc tttaataaga   2940
acaattccat cttaataaag agttacactt gttaataagt gctggcctcc tgttgttctt   3000
tgtacacccc acacaaaatt tcaaagaaac tttgatggca atatatctcc atggtcagct   3060
taaaaataga gaaaggaaaa catagaatta gccaagagtc acacaaaaca aagatcagtt   3120
gtttgttagg aaacaatcaa aatcaagtct cactttttcc agattggctt atggaacagc   3180
actgtaaggt gataacttgg ggcaaacatg taaataataa aacatatgtt ttaaatattc   3240
aggttagcac attttatgtt tctgtgagat taaaattgtg tgtgacatac ccgcttcctt   3300
aaaggcaatg tttctgaaaa tgttgtacct gctattcctg aatcagggat gggtcccaga   3360
atctgccttt taaacatctc agataatctg aagcctgctt aagtttgtaa ggcactgctt   3420
ttgcactcta aggaagaaaa aaacaagttt taattcccgt ctct                    3464
```

<210> SEQ ID NO 31
<211> LENGTH: 1584
<212> TYPE: DNA
<213> ORGANISM: Homo sapiens

<400> SEQUENCE: 31

```
cggggcagct ctgaggaaca aggtggaagc tcagagcgct ggtctccacc ctggtgcccc     60
tgggctggtg ctggcagtgg gagccgtggc tgtggatgag agacatagac gagagagtga    120
gatggcctgg tttgccctct acctcctgag ccttctctgg gctacagctg ggactagtac    180
ccagacccag agttcatgct ccgttccctc agcacaggag cccttggtca atggaataca    240
agtactcatg gagaactcgg tgacttcatc agcctaccca aaccccagca tcctgattgc    300
catgaatctg gccggagcct acaacttgaa ggcccagaag ctcctgactt accagctcat    360
gtccagcgac aacaacgatc taaccattgg gcacctcggc ctcaccatca tggccctcac    420
ctcctcctgc cgagaccctg gggataaagt atccattcta caaagacaaa tggagaactg    480
ggcaccttcc agccccaacg ctgaagcatc agccttctat gggcccagtc tagcgatctt    540
ggcactgtgc cagaagaact ctgaggcgac cttgccgata gccgtccgct ttgccaagac    600
cctgctggcc aactcctctc ccttcaatgt agacacagga gcaatggcaa ccttggctct    660
gacctgtatg tacaacaaga tccctgtagg ttcagaggaa ggttacagat ccctgtttgg    720
tcaggtacta aaggatattg tggagaaaat cagcatgaag atcaaagata atggcatcat    780
tggagacatc tacagtactg gcctcgccat gcaggctctc tctgtaacac ctgagccatc    840
taaaaaggaa tggaactgca agaagactac ggatatgata ctcaatgaga ttaagcaggg    900
gaaattccac aaccccatgt ccattgctca aatcctccct tccctgaaag gcaagacata    960
cctagatgtg ccccaggtca cttgtagtcc tgatcatgag gtacaaccaa ctctacccag   1020
caaccctggc cctggcccca cctctgcatc taacatcact gtcatataca ccataaataa   1080
ccagctgagg ggggttgagc tgctcttcaa cgagaccatc aatgttagtg tgaaaagtgg   1140
gtcagtgtta cttgttgtcc tagaggaagc acagcgcaaa aatcctatgt tcaaatttga   1200
aaccacaatg acatcttggg gccttgtcgt ctcttctatc aacaatatcg cggaaaatgt   1260
taatcacaag acatactggc agtttcttag tggtgtaaca cctttgaatg aaggggttgc   1320
```

-continued

```
tgactacata cccttcaacc acgagcacat cacagccaat ttcacacagt actaacgaag   1380
aggtgggttc agcttctatc aaacatctcc aaaggatggg tgaaattttt tccacttcat   1440
tttaaatcta tgcaaaaaag cgaatgcctg tgatgctacc atattcctgg taaaaacatg   1500
gagaaccact atgtagaata aaaatgcaaa gttcactgga gtctcaacat ctatgactca   1560
tgaaaataaa attttcatct tctc                                          1584
```

<210> SEQ ID NO 32
<211> LENGTH: 1537
<212> TYPE: DNA
<213> ORGANISM: Homo sapiens

<400> SEQUENCE: 32

```
gctctcatta ccttctgccc atcacttaat aaatagccag ccaattcatc aacattctgg     60
tacactgttg gagagatgag acagtcacac cagctgcccc tagtggggct cttactgttt    120
tcttttattc caagccaact atgcgagatt tgtgaggtaa gtgaagaaaa ctacatccgc    180
ctaaaacctc tgttgaatac aatgatccag tcaaactata acaggggaac cagcgctgtc    240
aatgttgtgt tgtccctcaa acttgttgga atccagatcc aaaccctgat gcaaaagatg    300
atccaacaaa tcaaatacaa tgtgaaaagc agattgtcag atgtaagctc gggagagctt    360
gccttgatta tactggcttt gggagtatgt cgtaacgctg aggaaaactt aatatatgat    420
taccacctga ctgacaagct agaaaataaa ttccaagcag aaattgaaaa tatggaagca    480
cacaatggca ctcccctgac taactactac cagctcagcc tggacgtttt ggccttgtgt    540
ctgttcaatg ggaactactc aaccgccgaa gttgtcaacc acttcactcc tgaaaataaa    600
aactattatt ttggtagcca gttctcagta gatactggtg caatggctgt cctggctctg    660
acctgtgtga agaagagtct aataaatggg cagatcaaag cagatgaagg cagtttaaag    720
aacatcagta tttatacaaa gtcactggta gaaaagattc tgtctgagaa aaaagaaaat    780
ggtctcattg gaaacacatt tagcacagga gaagccatgc aggccctctt tgtatcatca    840
gactattata atgaaaatga ctggaattgc caacaaactc tgaatacagt gctcacggaa    900
atttctcaag gagcattcag taatccaaac gctgcagccc aggtcttacc tgccctgatg    960
ggaaagacct tcttggatat taacaaagac tcttcttgcg tctctgcttc aggtaacttc   1020
aacatctccg ctgatgagcc tataactgtg acacctcctg actcacaatc atatatctcc   1080
gtcaattact ctgtgagaat caatgaaaca tatttcacca atgtcactgt gctaaatggt   1140
tctgtcttcc tcagtgtgat ggagaaagcc cagaaaatga atgatactat atttggtttc   1200
acaatggagg agcgctcatg gggccctat atcacctgta ttcagggcct atgtgccaac    1260
aataatgaca gaacctactg ggaacttctg agtggaggcg aaccactgag ccaaggagct   1320
ggtagttacg ttgtccgcaa tggagaaaac ttggaggttc gctggagcaa atactaataa   1380
gcccaaactt tcctcagctg cataaaatcc atttgcagtg gagttccatg tttattgtcc   1440
ttatgccttc ttcttcattt atcccagtac gagcaggaga gttaataacc tccccttctc   1500
tctctacatg ttcaataaaa gttgttgaaa gattaac                            1537
```

<210> SEQ ID NO 33
<211> LENGTH: 1866
<212> TYPE: DNA
<213> ORGANISM: Homo sapiens

<400> SEQUENCE: 33

```
ccgattcttg ctcactgctc acccacctgc tgctgccatg aggcaccttg ggccttcct     60
```

```
cttccttctg gggtcctgg gggccctcac tgagatgtgt gaaataccag agatggacag     120

ccatctggta gagaagttgg gccagcacct cttaccttgg atggaccggc tttccctgga     180

gcacttgaac cccagcatct atgtgggcct acgcctctcc agtctgcagg ctgggaccaa     240

ggaagacctc tacctgcaca gcctcaagct tggttaccag cagtgcctcc tagggtctgc     300

cttcagcgag gatgacggtg actgccaggg caagccttcc atgggccagc tggccctcta     360

cctgctcgct ctcagagcca actgtgagtt tgtcaggggc cacaaggggg acaggctggt     420

ctcacagctc aaatggttcc tggaggatga gaagagagcc attgggcatg atcacaaggg     480

ccaccccac actagctact accagtatgg cctgggcatt ctggccctgt gtctccacca     540

gaagcgggtc catgacagcg tggtggacaa acttctgtat gctgtggaac ctttccacca     600

gggccaccat tctgtggaca cagcagccat ggcaggcttg gcattcacct gtctgaagcg     660

ctcaaacttc aaccctggtc ggagacaacg gatcaccatg gccatcagaa cagtgcgaga     720

ggagatcttg aaggcccaga cccccgaggg ccactttggg aatgtctaca gcaccccatt     780

ggcattacag ttcctcatga cttcccccat gcctggggca gaactgggaa cagcatgtct     840

caaggcgagg gttgctttgc tggccagtct gcaggatgga gccttccaga atgctctcat     900

gatttcccag ctgctgcccg ttctgaacca caagacctac attgatctga tcttcccaga     960

ctgtctggca ccacgagtca tgttggaacc agctgctgag accattcctc agacccaaga    1020

gatcatcagt gtcacgctgc aggtgcttag tctcttgccg ccgtacagac agtccatctc    1080

tgttctggcc gggtccaccg tggaagatgt cctgaagaag gcccatgagt taggaggatt    1140

cacatatgaa acacaggcct cctcgtcagg cccctactta acctccgtga tggggaaagc    1200

ggccggagaa agggagttct ggcagcttct ccgagacccc aacaccccac tgttgcaagg    1260

tattgctgac tacagaccca aggatggaga aaccattgag ctgaggctgg ttagctggta    1320

gcccctgagc tccctcatcc cagcagcctc gcacactccc taggcttcta ccctccctcc    1380

tgatgtccct ggaacaggaa ctcgcctgac cctgctgcca cctcctgtgc actttgagca    1440

atgcccctg ggatcacccc agccacaagc ccttcgaggg ccctatacca tggcccacct    1500

tggagcagag agccaagcat cttccctggg aagtctttct ggccaagtct ggccagcctg    1560

gccctgcagg tctcccatga aggccacccc atggtctgat gggcatgaag catctcagac    1620

tccttggcaa aaaacggagt ccgcaggccg caggtgttgt gaagaccact cgttctgtgg    1680

ttggggtcct gcaagaaggc ctcctcagcc cgggggctat ggccctgacc ccagctctcc    1740

actctgctgt tagagtggca gctctgagct ggttgtggca cagtagctgg ggagacctca    1800

gcagggctgc tcagtgcctg cctctgacaa aattaaagca ttgatggcct gtggacctgc    1860

aaaaaa                                                               1866
```

<210> SEQ ID NO 34
<211> LENGTH: 2798
<212> TYPE: DNA
<213> ORGANISM: Homo sapiens

<400> SEQUENCE: 34

```
gccctctccc acagcggagt ccaaaacagg cctaccagtc agttcttatt tctattgggt      60

gtttccatgc tccaccatgt taagagctaa gaatcagctt tttttacttt cacctcatta     120

cctgaggcag gtaaaagaat catcaggctc caggctcata cagcaacgac ttctacacca     180

gcaacagccc cttcacccag aatgggctgc cctggctaaa aagcagctga aaggcaaaaa     240
```

-continued

```
cccagaagac ctaatatggc acaccccgga agggatctct ataaaaccct tgtattccaa    300
gagagatact atggacttac ctgaagaact tccaggagtg aagccattca cacgtggacc    360
atatcctacc atgtatacct ttaggccctg gaccatccgc cagtatgctg gttttagtac    420
tgtggaagaa agcaataagt tctataagga caacattaag gctggtcagc agggattatc    480
agttgccttt gatctggcga cacatcgtgg ctatgattca gacaaccctc gagttcgtgg    540
tgatgttgga atggctggag ttgctattga cactgtggaa gataccaaaa ttctttttga    600
tggaattcct ttagaaaaaa tgtcagtttc catgactatg aatggagcag ttattccagt    660
tcttgcaaat tttatagtaa ctggagaaga acaaggtgta cctaaagaga aacttactgg    720
taccatccaa aatgatatac taaaggaatt tatggttcga aatacataca tttttcctcc    780
agaaccatcc atgaaaatta ttgctgacat atttgaatat acagcaaagc acatgccaaa    840
atttaattca atttcaatta gtggatacca tatgcaggaa gcaggggctg atgccattct    900
ggagctggcc tatactttag cagatggatt ggagtactct agaactggac tccaggctgg    960
cctgacaatt gatgaatttg caccaaggtt gtctttcttc tggggaattg gaatgaattt   1020
ctatatggaa atagcaaaga tgagagctgg tagaagactc tgggctcact taatagagaa   1080
aatgtttcag cctaaaaact caaaatctct tcttctaaga gcacactgtc agacatctgg   1140
atggtcactt actgagcagg atccctacaa taatattgtc cgtactgcaa tagaagcaat   1200
ggcagcagta tttggaggga ctcagtcttt gcacacaaat tcttttgatg aagctttggg   1260
tttgccaact gtgaaaagtg ctcgaattgc caggaacaca caaatcatca ttcaagaaga   1320
atctgggatt cccaaagtgg ctgatccttg gggaggttct tacatgatgg aatgtctcac   1380
aaatgatgtt tatgatgctg ctttaaagct cattaatgaa attgaagaaa tgggtggaat   1440
ggccaaagct gtagctgagg gaatacctaa acttcgaatt gaagaatgtg ctgcccgaag   1500
acaagctaga atagattctg gttctgaagt aattgttgga gtaaataagt accagttgga   1560
aaaagaagac gctgtagaag ttctggcaat tgataatact tcagtgcgaa acaggcagat   1620
tgaaaaactt aagaagatca aatccagcag ggatcaagct ttggctgaac attgtcttgc   1680
tgcactaacc gaatgtgctg ctagcggaga tggaaatatc ctggctcttg cagtggatgc   1740
atctcgggca agatgtacag tgggagaaat cacagatgcc ctgaaaaagg tatttggtga   1800
acataaagcg aatgatcgaa tggtgagtgg agcatatcgc caggaatttg gagaaagtaa   1860
agagataaca tctgctatca agagggttca taaattcatg gaacgtgaag gtcgcagacc   1920
tcgtcttctt gtagcaaaaa tgggacaaga tggccatgac agaggagcaa aagttattgc   1980
tacaggattt gctgatcttg gttttgatgt ggacataggc cctcttttcc agactcctcg   2040
tgaagtggcc cagcaggctg tggatgcgga tgtgcatgct gtgggcgtaa gcaccctcgc   2100
tgctggtcat aaaaccctag ttcctgaact catcaaagaa cttaactccc ttggacggcc   2160
agatattctt gtcatgtgtg gaggggtgat accacctcag gattatgaat ttctgtttga   2220
agttggtgtt tccaatgtat ttggtcctgg gactcgaatt ccaaaggctg ccgttcaggt   2280
gcttgatgat attgagaagt gtttggaaaa gaagcagcaa tctgtataat atcctctttt   2340
tgttttagct tttgtctaaa atattatttt agttatgatc aaagaagaga gtaaagctat   2400
gtcttcaatt taatttcaat acctgatttg tactttcctt gaaagcttta ctttaaaata   2460
ccttacttat aggcctggtg tcatgctata agtatgtaca tacagtttca cttcaaaaat   2520
aaaaaaaaat ccctaaaaac tctctatact ctctataaca atactttatc aagaactctg   2580
gacaatggta ttatttttaa aaatcatggt gatgtattta ttagaatgtt tcttataaat   2640
```

-continued

```
ctctttcatt tttatattaa gaattaaact gtacctaaaa aaactctgac tattcccatt   2700
tctcagttta gcattacatt gtcttgagca ccagaaaata aaatccatat attaattaaa   2760
acctatcttg aaaaaaaaaa aaaaaaaaaa aaaaaaa                            2798
```

<210> SEQ ID NO 35
<211> LENGTH: 1637
<212> TYPE: DNA
<213> ORGANISM: Homo sapiens

<400> SEQUENCE: 35

```
aagaactggc ctgtacattt tcaaggaatt cttgagaggt tcttggagag attctgggag     60
ccaaacactc cattgggatc ctagctgttt tagagaacaa cttgtaatgg agccttcatc    120
tcttgagctg ccggctgaca cagtgcagcg cattgcggct gaactcaaat gccacccaac    180
ggatgagagg gtggctctcc acctagatga ggaagataag ctgaggcact tcagggagtg    240
cttttatatt cccaaaatac aggatctgcc tccagttgat ttatcattag tgaataaaga    300
tgaaaatgcc atctatttct tgggaaattc tcttggcctt caaccaaaaa tggttaaaac    360
atatcttgaa gaagaactag ataagtgggc caaaatagca gcctatggtc atgaagtggg    420
gaagcgtcct tggattacag gagatgagag tattgtaggc cttatgaagg acattgtagg    480
agccaatgag aaagaaatag ccctaatgaa tgctttgact gtaaatttac atcttctaat    540
gttatcattt tttaagccta cgccaaaacg atataaaatt cttctagaag ccaaagcctt    600
cccttctgat cattatgcta ttgagtcaca actacaactt cacggactta acattgaaga    660
aagtatgcgg atgataaagc caagagaggg ggaagaaacc ttaagaatag aggatatcct    720
tgaagtaatt gagaaggaag gagactcaat tgcagtgatc ctgttcagtg gggtgcattt    780
ttacactgga cagcacttta atattcctgc catcacaaaa gctggacaag cgaagggttg    840
ttatgttggc tttgatctag cacatgcagt tggaaatgtt gaactctact tacatgactg    900
gggagttgat tttgcctgct ggtgttccta caagtattta aatgcaggag caggaggaat    960
tgctggtgcc ttcattcatg aaaagcatgc ccatacgatt aaacctgcat tagtgggatg   1020
gtttggccat gaactcagca ccagatttaa gatggataac aaactgcagt taatccctgg   1080
ggtctgtgga ttccgaattt caaatcctcc cattttgttg gtctgttcct tgcatgctag   1140
tttagagatc tttaagcaag cgacaatgaa ggcattgcgg aaaaaatctg ttttgctaac   1200
tggctatctg gaatacctga tcaagcataa ctatggcaaa gataaagcag caaccaagaa   1260
accagttgtg aacataatta ctccgtctca tgtagaggag cgggggtgcc agctaacaat   1320
aacattttct gttccaaaca aagatgtttt ccaagaacta gaaaaaagag gagtggtttg   1380
tgacaagcgg aatccaaatg gcattcgagt ggctccagtt cctctctata attctttcca   1440
tgatgtttat aaatttacca atctgctcac ttctatactt gactctgcag aaacaaaaaa   1500
ttagcagtgt tttctagaac aacttaagca aattatactg aaagctgctg tggttatttc   1560
agtattattc gatttttaat tattgaaagt atgtcaccat tgaccacatg taactaacaa   1620
taaataatat accttac                                                  1637
```

<210> SEQ ID NO 36
<211> LENGTH: 1908
<212> TYPE: DNA
<213> ORGANISM: Homo sapiens

<400> SEQUENCE: 36

-continued

```
gaattcatga aaacgtagct cgtcctcaaa aaaaacagaa gaggagtaat cattttaagg     60
gagaaatata tacgaaagga acaagatttt gaagcaccca agctgccacc tacattaaaa    120
cacggtaggt ggctaaacac cagtcttcaa tgcccttcca cagcctcagt ctgaaaaata    180
ctgtgcaggt gacccaagtg aggggtcacc cttgggcttt tcctgtggca gtatctctgg    240
tttaaaaaca aacaaacgta cttattgcgt tgaaggacgg caacaggaag gactccatga    300
ttagtcacat ctataccatc ctaagaaact ttatccaccc aaactgtatt tcagacttta    360
taatctaaac tacaaaaagt gttcactggg gaactgcaca atatgactgc ttttaaccgt    420
agtgatttca aatattgagc catgctgttg cagtcttaaa aactggagac ctaagggcag    480
ctttcttcta gtcacccaat ccagcacttt tttaaaaaat cagtaaaact cttcgaccac    540
caaggaaaaa aaaaaaggat ggaggttaaa agacgcaccc cttgcccaca agccccctca    600
tcagaatggg agtcaggaga cctgagttcc tgtctcaggc ctgccattaa aaacctgcat    660
aacctttgcc tatctcctca aacggaagta ctaaaacctc agcgcttcac ccaatttgta    720
gccccggctg ggctcttccc accttcccct tcttcagccc gccccttcct cctccagccc    780
tatcatcggg cggagggtcc ccgcctccgc ccgccttacc cacaagcccc gcccccccag    840
ccccgatggc cctgcccagt cccagacaga acctactacg tgcggcggca gctggggcgg    900
gaaggcgggc gctgggggcg ctgcggccgc tgcagcgcag ggtccacctg gtcggctgca    960
cctgtggagg aggaggtgga tttcaggctt cccgtagact ggaagaatcg gctcaaaacc   1020
gcttgcctcg caggggctga gctggaggca gcgaggccgc ccgacgcagg cttccggcga   1080
gacatggcag ggcaaggatg gcagcccggc ggcagggccc ggcgaggagc gcgaacccgc   1140
ggccgcagtt cccaggcgtc tgcgggcgcg agcacgccgc gaccctgcgt gcgccggggc   1200
ggggggcgg ggcctcgcct gcacaaatag ggacgagggg gcggggcggc cacaatttcg   1260
cgccaaactt gaccgcgcgt tctgctgtaa cgagcgggct cggaggtcct cccgctgctg   1320
tcatggttgg ttcgctaaac tgcatcgtcg ctgtgtccca gaacatgggc atcggcaaga   1380
acggggacct gccctggcca ccgctcaggt atctgccggg ccggggcgat gggacccaaa   1440
cgggcgcagg ctgcccacgg tcggggtacc tgggcgggac gcgccggccg actcccggcg   1500
agaggatggg gccagacttg cggtctgcgc tggcaggaag ggtgggcccg actggattcc   1560
ccttttctgc tgcgcgggag gcccagttgc tgatttctgc ccggattctg ctgcccggtg   1620
aggtcttgcc ctgcggcgcc ctcgcccagg gcaaagtccc agccctggag aaaacacctc   1680
acccctaccc acagcgctcc gtttgtcagg tgccttagag ctcgagccca agggataatg   1740
tttcgagtaa cgctgtttct ctaacttgta ggaatgaatt cagatatttc cagagaatga   1800
ccacaacctc ttcagtagaa ggtaatgtgg gattaagtag ggtcttgctt gatgaagttt   1860
accagtgcaa atgttagtta aatggaaagt tttccgtgtt aatctggg                1908
```

<210> SEQ ID NO 37
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 37

```
cccacggtcg gggtggccga ctcccggcga                                      30
```

<210> SEQ ID NO 38
<211> LENGTH: 21

-continued

<212> TYPE: DNA
<213> ORGANISM: Artificial Sequence
<220> FEATURE:
<223> OTHER INFORMATION: Description of Artificial Sequence:primer

<400> SEQUENCE: 38
ctaaactgca tcgtcgctgt g 21

<210> SEQ ID NO 39
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 39
aaaaggggaa tccagtcgg 19

<210> SEQ ID NO 40
<211> LENGTH: 19
<212> TYPE: DNA
<213> ORGANISM: Artificial Sequence
<220> FEATURE:
<223> OTHER INFORMATION: Description of Artificial Sequence:PCR product

<400> SEQUENCE: 40
acctgggcgg gacgcgcca 19

<210> SEQ ID NO 41
<211> LENGTH: 1275
<212> TYPE: DNA
<213> ORGANISM: Homo sapiens

<400> SEQUENCE: 41
ctgcagcgcc agggtccacc tggtcggctg cacctgtgga ggaggaggtg gatttcaggc 60
ttcccgtaga ctggaagaat cggctcaaaa ccgcttgcct cgcaggggct gagctggagg 120
cagcgaggcc gcccgacgca ggcttccggc gagacatggc agggcaagga tggcagcccg 180
gcggcagggc ccggcgagga gcgcgaaccc gcggccgcag ttcccaggcg tctgcgggcg 240
cgagcacgcc gcgaccctgc gtgcgccggg gcgggggggc ggggcctcgc ctgcacaaat 300
agggacgagg gggcggggcg gccacaattt cgcgccaaac ttgaccgcgc gttctgctgt 360
aacgagcggg ctcggaggtc ctcccgctgc tgtcatggtt ggttcgctaa actgcatcgt 420
cgctgtgtcc cagaacatgg gcatcggcaa gaacggggac ctgccctggc caccgctcag 480
gtatctgccg ggccggggcg atgggaccca aacgggcgca ggctgcccac ggtcggggta 540
cctgggcggg acgcgccagg ccgactcccg gcgagaggat ggggccagac ttgcggtctg 600
cgctggcagg aagggtgggc ccgactggat tcccctttc tgctgcgcgg gaggcccagt 660
tgctgatttc tgcccggatt ctgctgcccg gtgaggtctt tgccctgcgg cgccctcgcc 720
cagggcaaag tcccagccct ggagaaaaca cctcacccct acccacagcg ctccgtttgt 780
caggtgcctt agagctcgag cccaagggat aatgtttcga gtaacgctgt ttctctaact 840
tgtaggaatg aattcagata tttccagaga atgaccacaa cctcttcagt agaaggtaat 900
gtgggattaa gtagggtctt gcttgatgaa gtttaccagt gcaaatgtta gttaaatgga 960
aagttttccg tgttaatctg ggaccttttc tcttattatg gatctgtatg atctgtatgc 1020
agttcccaag gttcatttac cattattaaa aaatttttgt cttagaaatt ttatgtatgt 1080
caacgcacga gcaaattatc aggcatgggg cagaattggc aactgggtgg aggcttcggt 1140

```
ggaggttagc actccgaaag gaaaacagag taggcctttg gaacagctgc tggaagagat   1200

aaggcctgaa caagggcagt ggagaagaga gggtaaaaat tttttaaggt tacatgaccc   1260

tggattttgg agatc                                                    1275
```

<210> SEQ ID NO 42
<211> LENGTH: 1256
<212> TYPE: DNA
<213> ORGANISM: Homo sapiens

<400> SEQUENCE: 42

```
ctgcagcgcc agggtccacc tggtcggctg cacctgtgga ggaggaggtg gatttcaggc     60

ttcccgtaga ctggaagaat cggctcaaaa ccgcttgcct cgcaggggct gagctggagg    120

cagcgaggcc gcccgacgca ggcttccggc gagacatggc agggcaagga tggcagcccg    180

gcggcagggc ccggcgagga gcgcgaaccc gcggccgcag ttcccaggcg tctgcgggcg    240

cgagcacgcc gcgaccctgc gtgcgccggg gcgggggggc ggggcctcgc ctgcacaaat    300

agggacgagg gggcggggcg gccacaattt cgcgccaaac ttgaccgcgc gttctgctgt    360

aacgagcggg ctcggaggtc ctcccgctgc tgtcatggtt ggttcgctaa actgcatcgt    420

cgctgtgtcc cagaacatgg gcatcggcaa gaacggggac ctgccctggc caccgctcag    480

gtatctgccg ggccggggcg atgggaccca aacgggcgca ggctgcccac ggtcggggtg    540

gccgactccc ggcgagagga tggggccaga cttgcggtct gcgctggcag gaagggtggg    600

cccgactgga ttccccttt ctgctgcgcg ggaggcccag ttgctgattt ctgcccggat    660

tctgctgccc ggtgaggtct ttgccctgcg gcgccctcgc ccagggcaaa gtcccagccc    720

tggagaaaac acctcacccc tacccacagc gctccgtttg tcaggtgcct tagagctcga    780

gcccaaggga taatgtttcg agtaacgctg tttctctaac ttgtaggaat gaattcagat    840

atttccagag aatgaccaca acctcttcag tagaaggtaa tgtgggatta agtagggtct    900

tgcttgatga agtttaccag tgcaaatgtt agttaaatgg aaagttttcc gtgttaatct    960

gggacctttt ctcttattat ggatctgtat gatctgtatg cagttcccaa ggttcattta   1020

ccattattaa aaaattttg tcttagaaat tttatgtatg tcaacgcacg agcaaattat   1080

caggcatggg gcagaattgg caactgggtg gaggcttcgg tggaggttag cactccgaaa   1140

ggaaaacaga gtaggccttt ggaacagctg ctggaagaga taaggcctga acaagggcag   1200

tggagaagag agggtaaaaa tttttaagg ttacatgacc ctggattttg gagatc        1256
```

<210> SEQ ID NO 43
<211> LENGTH: 55
<212> TYPE: DNA
<213> ORGANISM: Artificial Sequence
<220> FEATURE:
<223> OTHER INFORMATION: Description of Artificial Sequence:PCR product

<400> SEQUENCE: 43

```
gctgcccacg gtcggggtac ctgggcggga cgcgccaggc cgactcccgg cgaga          55
```

<210> SEQ ID NO 44
<211> LENGTH: 36
<212> TYPE: DNA
<213> ORGANISM: Artificial Sequence
<220> FEATURE:
<223> OTHER INFORMATION: Description of Artificial Sequence:PCR product

<400> SEQUENCE: 44

```
gctgcccacg gtcggggtgg ccgactcccg gcgaga                               36
```

```
<210> SEQ ID NO 45
<211> LENGTH: 1273
<212> TYPE: DNA
<213> ORGANISM: Homo sapiens

<400> SEQUENCE: 45

ctgcagcgca gggtccacct ggtcggctgc acctgtggag gaggaggtgg atttcaggct     60

tcccgtagac tggaagaatc ggctcaaaac cgcttgcctc gcaggggctg agctggaggc    120

agcgaggccg cccgacgcag gcttccggcg agacatggca gggcaaggat ggcagcccgg    180

cggcagggcc cggcgaggag cgcgaacccg cggccgcagt tcccaggcgt ctgcgggcgc    240

gagcacgccg cgaccctgcg tgcgccgggg cgggggggcg gggcctcgcc tgcacaaata    300

gggacgaggg ggcggggcgg ccacaatttc gcgccaaact tgaccgcgcg ttctgctgta    360

acgagcgggc tcggaggtcc tcccgctgct gtcatggttg gttcgctaaa ctgcatcgtc    420

gctgtgtccc agaacatggg catcggcaag aacggggacc tgccctggcc accgctcagg    480

tatctgccgg gccggggcga tgggacccaa acgggcgcag gctgcccacg gtcggggtac    540

ctgggcggga cgcgccggcc gactcccggc gagaggatgg ggccagactt gcggtctgcg    600

ctggcaggaa gggtgggccc gactggattc ccctttctg ctgcgcggga ggcccagttg    660

ctgatttctg cccggattct gctgcccggt gaggtctttg ccctgcggcg ccctcgccca    720

gggcaaagtc ccagccctgg agaaaacacc tcacccctac ccacagcgct ccgtttgtca    780

ggtgccttag agctcgagcc caagggataa tgtttcgagt aacgctgttt ctctaacttg    840

taggaatgaa ttcagatatt tccagagaat gaccacaacc tcttcagtag aaggtaatgt    900

gggattaagt agggtcttgc ttgatgaagt ttaccagtgc aaatgttagt taaatggaaa    960

gttttccgtg ttaatctggg accttttctc ttattatgga tctgtatgat ctgtatgcag   1020

ttcccaaggt tcatttacca ttattaaaaa atttttgtct tagaaatttt atgtatgtca   1080

acgcacgagc aaattatcag gcatggggca gaattggcaa ctgggtggag gcttcggtgg   1140

aggttagcac tccgaaagga aaacagagta ggcctttgga acagctgctg gaagagataa   1200

ggcctgaaca agggcagtgg agaagagagg gtaaaaattt tttaaggtta catgaccctg   1260

gattttggag atc                                                      1273


<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence:PCR product

<400> SEQUENCE: 46

acctgggcgg gacgcgcc                                                   18
```

METHODS FOR DIAGNOSING, PREVENTING, AND TREATING DEVELOPMENTAL DISORDERS DUE TO A COMBINATION OF GENETIC AND ENVIRONMENTAL FACTORS

FIELD OF THE INVENTION

The invention relates generally to novel methods of diagnosing, preventing, and treating specific diseases which are caused by a combination of genetic and environmental factors. One such disease exemplified is schizophrenia.

BACKGROUND OF THE INVENTION

The term "schizophrenia" was introduced by Bleuler in the beginning of this century to encompass a dissociation or disruption of thought processes, along with a dichotomy among thought, emotion, and behavior [Bleuler, *Translation J. Zinkin*, New York: International University Press (1950)]. The current definition of schizophrenia includes a break with reality that is usually manifested as hallucinations, delusions, or disruption in thought processes [Carpenter et al., *Medical Progress*, 330:681–690 (1994)]. At present the nationally accepted definition for the diagnosis of schizophrenia is contained in Diagnostic and Statistical Manual for Mental Disorders, Fourth Edition, Washington, D.C (1994): American Psychiatric Association, hereby incorporated by reference in its entirety.

Schizophrenia is a clinical syndrome that has a profound influence on public health. The symptoms for schizophrenia begin early in life, and continues for most patients throughout their lives. An estimate of the direct and indirect costs of schizophrenia was thirty-three billion dollars for 1990 in the United States alone [Carpenter et al., 1994, supra]. Indeed, one of every forty dollars spent for total heath care expenditures in the United States is spent on treating schizophrenia [Rupp et al., *Psychiatric Clin. North Am.*, 16:413–423 (1993)]. Furthermore, estimates have been made suggesting that up to 50% of the homeless American population is schizophrenic [Bachrach, In: *Treating the Homeless Mentally Ill*, Washington, D.C., American Psychiatric Press, 13–40, Lamb et al. ed. (1992)].

The genetic factors in schizophrenia, though clearly documented to be present, are not simple [Carpenter and Buchanan, *N. Engi. J. Med.*, 330:681–689 (1994); Gottesman, *Clin. Genet.*, 46:116–123 (1994)]. Schizophrenia is, at least in part, a neurodevelopmental disorder, a birth defect in which the brain has been subtly damaged during development [Carpenter and Buchanan, *N. Engl. J. Med.*, 330:681–689 (1994); Weinberger, *Arch. Gen. Psychiatry*, 44:660–669 (1987); Brixey et al., *J. Clin. Psychol.*, 49:447–456 (1993)]. Evidence of this damage is seen both at autopsy [Kovelman and Scheibel, *Biol. Psychiatry*, 19:1601–1621 (1984); Bogerts et al., *Arch. Gen. Psychiatry*, 42:784–791 (1985); Jakob and Beckman, *J. Neural Transm.*, 65:303–326 (1986); Brown et al., *Arch. Gen. Psychiatry*, 43:36–42 (1986); Benes and Bird, *Arch Gen Psychiatry*, 44:608–616 (1987); Colter et al., *Arch Gen Psychiatry*, 44:1023 (1987); Altshuler et al., *Arch. Gen. Psychiatry*, 47:1029–1034 (1990); Pakkenberg, *Schizophr. Res.*, 7:95–100 (1992); Bogerts, *Schizophr. Bull.*, 19:431–445 (1993); Shapiro, *Schizophr. Res.*, 10:187–239 (1993)] and by neuroimaging [Jeste et al., *Br. J. Psychiatry*, 153:444–459 (1988); Suddath et al., *Am. J. Psychiatry*, 146:464–472 (1989); Suddath et al., *N. Engl. J. Med.*, 322:789–794 (1990); DeLisi et al., *Biol. Psychiatry*, 29:159–175 (1991); Breier et al., *Arch. Gen. Psychiatry*, 49:921–926 (1992); O'Callaghan et al., *J. R. Soc. Med.*, 85:227–231 (1992); Bogerts et al., *Biol. Psychiatry*, 33:236–246 (1993); Andreasen et al., *Science*, 266:294–298 (1994)]. The pattern of this brain damage and the presence of minor congenital abnormalities point to an insult occurring during the second trimester of fetal development [Bracha et al., *Biol. Psychiatry*, 30:719–725 (1991); Bracha et al., *Am. J. Psychiatry*, 149:1355–1361 (1992); Green et al., *Psychiatry Res.*, 53:119–127 (1994)]. Epidemiological studies have documented a season-of-birth effect by which schizophrenics are more frequently born during winter and early spring than during other seasons [Boyd et al., *Schizophr. Bull.*, 12:173–186 (1986); Kendell and Adams, *Br. J. Psychiatry*, 158:758–763 (1991); O'Callaghan et al., *Br. J. Psychiatry*, 158:764–769 (1991)].

Also, individuals exposed to an influenza epidemic [Mednick et al., *Arch. Gen. Psychiatry*, 45:189–192 (1988); Barr et al., *Arch. Gen. Psychiatry*, 47:869–874 (1990); O'Callaghan et al., *Lancet.*, 337:1248–1250 (1991); Murray et al., *J. Psychiatr. Res.*, 26:225–235 (1992); Adams et al., *Br. J. Psychiatry*, 163:522–534 (1993)] or famine [Susser and Lin, *Arch. Gen. Psychiatry*, 49:983–988 (1992)] during their second trimester of fetal development have increased risk of later developing schizophrenia, according to some studies but not others [Kendell, *Arch. Gen. Psychiatry*, 46:878–882 (1989); Crow and Done, Br. *J. Psychiatry*, 161:390–393 (1992)]. This has suggested that an environmental effect such as dietary deficiency, virus infection [Kirch, *Schizophr. Bull.*, 19:355–370 (1993)], vitamin deficiency, or effect of cold weather may be acting during fetal development.

Linkage mapping studies in schizophrenia have been difficult. Recently, some studies [Straub et al., *Nature Genet.*, 11:287–293 (1995); Schwab et al., *Nature Genet.*, 11:325–327 (1995); Moises et al., *Nature Genet.*, 11:321–324 (1995)] have supported a gene locus on chromosome 6 (6p24–22, near the HLA region) as having an effect in schizophrenia; other studies gave little or no support to a marker in this region [Wang et al., *Nature Genet.*, 10:41–46 (1995); Mowry et al., *Nature Genet.*, 11:233–234 (1995); Gurling et al., *Nature Genet.*, 11:234–235 (1995); Antonarakis et al., *Nature Genet.*, 11:235–236 (1995)]. At best this locus appeared to be involved in only about 15–30% of families [Straub et al., 1995, supra]. Also, some evidence for loci on chromosomes 3 [Pulver et al., *Am. J. Med. Genet.*, 60:252–260 (1995), 8 [Pulver et al., *Am. J. Med. Genet.*, 60:252–260 (1995); Kendler et al., *Am. J. Psych*. 153:1534–1540 (1996), 9 [Coon et al., *Biol. Psychiatry*, 34:277–289 (1993); Moises et al., *Nature Genet.*, 11:321–324 (1995)] and 22 [Coon et al., *Am. J. Med. Genet.*, 54:72–79 (1994); Pulver et al., *Am. J. Med. Genet.*, 54:3–43 (1994)]have been reported. In addition, two polymorphic markers very close to the gene encoding dihydrofolate reductase (DHFR) on chromosome 5q, D5576 and D5S39, gave very high lod scores (as high as 6.49, i.e. odds of about 3 million to one in favor of genetic linkage versus chance occurrence) in 7 British and Icelandic schizophrenia families studied [Schwab et al., *Nat. Genet.* 11:325–327 (1997); Straub et al., Molec Psychiatr. 2:148–155 (1997)]. However, this result could not be confirmed in studies of numerous other families.

There could be several reasons for this difficulty. First, there may be more than one gene involved, (locus heterogeneity). Second, the genetic factor(s) may be common in the population (high disease allele frequency), thus diminishing the power of linkage studies [Terwilliger and Ott, *Handbook of Human Genetic Linkage*, Baltimore: Johns Hopkins Univ. Pr., 181 (1994)]. Third, the correct genetic model may be unknown [Owen, *Psychol. Med.*, 22:289–293 (1992)]. Any or all of these factors could diminish the power of a linkage study sufficiently to make success very difficult [Terwilliger and Ott, 1994, supra].

Thus the current (developmental) model for schizophrenia is that genetic and environmental factors cause brain damage in a fetus that later develops schizophrenia. However, the genetic and environmental factors have not been identified. Also, extensive linkage and association studies have failed to identify genes determining schizophrenia.

Indeed, schizophrenia appears to be just one of a family of developmental disorders whose cause has not been identified. Other such developmental disorders are defined by the Diagnostic and Statistical Manual for Mental Disorders, Fourth Edition, Washington, D.C (1994) and include: Tourette Syndrome which is identical to Tourette's Disorder and is a subcategory of Tic Disorders; Bipolar Disorder which is identical with Bipolar I Disorder or Bipolar II disorder; Autism which is identical with Autistic Disorder which is a subcategory of Pervasive Developmental Disorders; Conduct disorder which is a subcategory of Attention-Deficit and Disruptive Behavioral Disorders; Attention-Deficit Hyperactivity Disorder which is identical to Attention-Deficit/Hyperactivity Disorder and to Attention-Deficit/Hyperactivity Disorder NOS (not otherwise specified) which is also a subcategory of Attention-Deficit and Disruptive Behavioral Disorders; Obsessive-Compulsive Disorder which is a subtype of Anxiety Disorders; Chronic Multiple Tics Syndrome which is identical to Chronic Motor or Vocal Tic Disorder which is a subtype of Tic Disorders; and Learning Disorders.

In addition Spina bifida is a developmental disorder. Spina bifida is a form of neural tube defect in which neural elements (spinal nerves or spinal chord) or coverings of the brain and spinal chord (dura mater, arachnoid mater) herniate through a midline defect into a cystic cavity covered completely or partially by skin.

Therefore, there is a need for new methods of diagnosing individuals susceptible to developing a developmental disorder. In addition, there is a need for methods of identifying individuals susceptible to having offspring that develop a developmental disorder. Finally, there is a need for a method of treating such susceptible individuals in order to prevent and/or ameliorate the symptoms due to and/or associated with the developmental disorder.

The citations of any reference herein should not be construed as an admission that such reference is available as "Prior Art" to the instant application.

SUMMARY OF THE INVENTION

The present invention provides methods of diagnosing, preventing and/or treating specific developmental disorders. Towards this end the present invention provides methods of identifying an individual as being genetically or environmentally susceptible for developing or having a developmental disorder or for having offspring that develop the developmental disorder. Such a developmental disorder can be schizophrenia, spina bifida cystica, Tourette's syndrome, bipolar illness, autism, conduct disorders, attention deficit disorder, obsessive compulsive disorder, chronic multiple tic syndrome and learing disorders such as dyslexia. In addition, any of the methods provided herein for identifying an individual as being genetically and/or environmentally susceptible for having or developing a developmental disorder or for having offspring that develop the developmental disorder can also be used in diagnosing the individual, preferably in conjunction with a clinical diagnosis.

Therefore, the present invention provides methods of identifying an individual as being genetically susceptible for having or developing a developmental disorder. The present invention further provides methods of identifying an individual as being genetically susceptible for having offspring that are susceptible for developing a developmental disorder. Methods of identifying an individual as being susceptible due to environmental factors for having or developing a developmental disorder are also provided. In addition, the present invention provides methods of identifying an individual as being susceptible of having offspring that are susceptible for developing a developmental disorder. The present invention also provides methods of identifying an individual as being susceptible for having or developing a developmental disorder due to both environmental and genetic factors. The present invention further provides methods of identifying an individual as being susceptible for having offspring that are susceptible for developing a developmental disorder The present invention therefore provides methods for compiling genetic reference datasets, environmental reference datasets and/or genetic and environmental reference datasets for use in determining a predicted probability for an individual of having a susceptibility for having or developing a developmental disorder, or for having offspring that develop a developmental disorder.

In one aspect of the invention, the present invention provides methods that comprise generating a genetic reference dataset for use in determining the predicted probability of an individual for having a susceptibility for having or developing a developmental disorder due to genetic factors, or for having offspring that develop a developmental disorder due to genetic factors.

One such embodiment comprises collecting a biological sample from a human subject. The human subject can be a diagnostic proband, a blood relative of the diagnostic proband, an affected proband, a blood relative of the affected proband, a control proband, and/or a blood relative of the control proband. The biological sample contains nucleic acids and/or proteins from the human subject. The nucleic acids and/or proteins from the biological sample are then analyzed resulting in a partial or full genotype for the alleles of the genes involved in folate, pyridoxine, and/or cobalamin metabolisim The partial or full genotype then forms a dataset of genetic explanatory variables for the human subject. The dataset of genetic explanatory variables is then compiled from multiple human subjects into a genetic reference dataset. Such compilations are exemplified in the Detailed Description and Examples below.

In another aspect, the present invention provides a method that comprises generating a genetic and environmental reference dataset for use in determining the predicted probability of an individual for having a susceptibility for having or developing a developmental disorder due to genetic factors and environmental factors, or for having offspring that develop a developmental disorder due to genetic factors and environmental factors. One such embodiment comprises obtaining dietary and epidemiological information for environmental explanatory variables for the human subjects and combining the environmental explanatory variables with a genetic reference dataset for the human subjects as described above.

In another aspect, the present invention provides an environmental reference dataset for use in the determination of the predicted probability for an individual for having a susceptibility for having or developing a developmental disorder due to environmental factors, or for having offspring that develop a developmental disorder due to environmental factors One such embodiment comprises obtaining dietary and epidemiological infornation for environmental explanatory variables for a human subject. The human subject can be a diagnostic proband, a blood relative of the diagnostic proband, an affected proband, a blood relative of the affected proband, a control proband, or a blood relative of the control proband. The dataset of environmental explanatory variables is then compiled from multiple human subjects into an environmental reference dataset for the human subjects.

The developmental disorder forming the basis of the reference datasets of the present invention can be schizophrenia, or spina bifida cystica, or Tourette's syndrome, or dyslexia, or conduct disorder, or attention-deficit hyperactivity disorder, or bipolar illness, or autism, or chronic multiple tic syndrome or obsessive-compulsive disorder, or like disorders. A blood relative is preferably the mother of the individual, a sibling, the father or a grandparent of the individual. When the reference dataset is for use in the determination of the predicted probability for an individual of having a susceptibility for having offspring that develop a developmental disorder, the individual is preferably a pregnant woman. The reference datasets of the present invention are themselves part of the present invention.

The present invention further provides methods of estimating the genetic susceptibility of an individual to have or to develop a developmental disorder, or to have offspring that develop a developmental disorder. In one such embodiment the method comprises collecting a biological sample from a participant (or participants) who is either the individual or a blood relative of the individual. The biological sample contains nucleic acids and/or proteins of the participant. The analysis of the nucleic acids and/or proteins from the biological sample yield a partial or fall genotype for the alleles of the genes involved in folate, pyridoxine, and/or cobalamin metabolism. The partial or full genotype forms a dataset of genetic explanatory variables for the participants. The dataset of genetic explanatory variables obtained are added to a genetic reference dataset forming a combined genetic dataset. A model is then formulated comprising the genetic explanatory variables obtained from the participants and the combined genetic dataset is analyzed. A predicted probability for the individual for having and/or developing a developmental disorder and/or having offspring that develop a developmental disorder is then determined. The genetic susceptibility of an individual to have or to develop a developmental disorder and/or have offspring that develop a developmental disorder is estimated. In a preferred embodiment, analyzing the combined genetic dataset is performed by binary linear regression. In a more preferred embodiment, the binary linear regression is performed with the SAS system In another preferred embodiment, the model is modified by adding or subtracting one or more genetic explanatory variables and the combined genetic dataset is re-analyzed, preferably by binary logistic regression. In this case a model is chosen that best fits the data. This can be accomplished by testing the model for goodness of fit.

The present invention also provides methods of estimating the genetic and environmental susceptibility of an individual to have or to develop a developmental disorder and/or for having offspring that develop a developmental disorder. One such embodiment comprises collecting a biological sample from one or more participants. Again, the participant is either the individual or a blood relative of the individual. The biological sample contains nucleic acids and/or proteins of the participant. The nucleic acids and/or proteins from the biological sample are analyzed resulting in a partial or full genotype for the alleles of the genes involved in folate, pyridoxine, and/or cobalamin metabolism. The partial or full genotype forms a dataset of genetic explanatory variables for the participant. Dietary and epidemiological information for environmental explanatory variables for the participant (s) are also obtained which are used to form a dataset of environmental explanatory variables for the participant(s). The datasets of genetic explanatory variables and the dataset of environmental explanatory variables are added to a genetic and environmental reference dataset forming a combined genetic and environmental dataset. A model is formulated comprising the genetic and environmental explanatory variables obtained from the participant(s). The combined genetic and environmental dataset is then analyzed and a predicted probability for the individual for having and/or developing a developmental disorder and/or for having offspring that develop a developmental disorder is determined. The genetic and environmental susceptibility of an individual to have or to develop a developmental disorder and/or have offspring that develop a developmental disorder is estimated. In a preferred embodiment, analyzing the combined genetic and environmental dataset is performed by binary linear regression. In a more preferred embodiment the binary linear regression is performed with the SAS system. In another preferred embodiment the model is modified by adding or subtracting one or more genetic and/or environmental explanatory variables and the combined genetic and environmental dataset is re-analyzed preferably, by binary logistic regression. In this case a model is chosen that best fits the data. This can be accomplished by testing the model for goodness of fit.

For any of these methods, the developmental disorder can be schizophrenia, spina bifida cystica, Tourette's syndrome, bipolar illness, autism, conduct disorder, attention deficit hyperactivity disorder, obsessive compulsive disorder, chronic multiple tic syndrome and learning disorders such as dyslexia.

In a particular embodiment, the individual is suspected of being genetically susceptible of having or for developing the developmental disorder and/or of being genetically susceptible of having offspring that develop the developmental disorder. In a preferred embodiment of this type, the individual is suspected of being genetically susceptible for having or for developing the developmental disorder and/or of being genetically susceptible of having offspring that develop the developmental disorder because a blood relative has the developmental disorder. In one such embodiment the blood relative is a parent, a sibling, or a grandparent. In a preferred embodiment the blood relative is the mother of the individual. In a particular embodiment in which the individual is suspected of being genetically susceptible of having offspring that develop the developmental disorder, the individual is a pregnant woman. In another such embodiment the individual is the mate of the pregnant woman. In a particular embodiment exemplified below, the developmental disorder is schizophrenia.

Since the availability of the data regarding the genetic and environmental explanatory factors can vary in separate determinations, variations in the explanatory factors used is clearly envisioned by the present invention.

The present invention further provides methods of lowering the risk of a pregnant woman to have a child that will develop a developmental disorder. One such embodiment comprises administering methylfolate, cobalamin or pyridoxine to the pregnant woman and/or fetus, which lowers the risk of the pregnant woman to give birth to a child with a developmental disorder. In a particular embodiment of this type, the pregnant woman had been previously determined to be susceptible of having offspring that develop a developmental disorder by a method disclosed herein. The present invention further provides a method of determining if any treatment is advisable for a pregnant woman that is genetically susceptible to having offspring that develop a developmental disorder which comprises determining the concentration of a risk factor from a tissue sample or body fluid from the pregnant woman. When the concentration of the risk factor is statistically above or below an accepted normal range, treatment is advisable.

The present invention further provides methods of determining if any treatment is advisable for a pregnant woman who has been determined to be susceptible to having offspring that develop a developmental disorder. One such embodiment comprises determining the concentration of a risk factor from a tissue sample or body fluid from the pregnant woman. When the concentration of the risk factor is statistically above or below an accepted normal range, treatment is advisable. In a particular embodiment of this type, the pregnant woman had been previously determined to be susceptible of having offspring that develop a developmental disorder by a method disclosed herein.

Methods of monitoring the effect of the administration of methylfolate, cobalamin or pyridoxine to the pregnant woman who has been determined to be susceptible to having offspring that develop a developmental disorder are also included in the present invention. One such embodiment comprises determining the concentration of a risk factor from a tissue sample or body fluid from the pregnant woman. When the concentration of the risk factor is statistically within an accepted normal range, the treatment is deemed effective. In a particular embodiment of this type, the pregnant woman had been previously determined to be susceptible of having offspring that develop a developmental disorder by a method disclosed herein. The risk factor can be any substance and/or metabolite linked to folate and/or cobalamin and/or pyridoxine metabolism. In one embodiment, the risk factor is homocysteine. In yet another embodiment, the risk factor is folate. In still another embodiment, the risk factor is cobalamin.

The present invention also provides a method of treating an asymptomatic individual determined to be susceptible for developing a developmental disorder comprising administering methylfolate, cobalamin and/or pyridoxine. In a particular embodiment of this type, the asymptomatic individual had been previously determined to be susceptible of developing a developmental disorder by a method disclosed herein.

The DNA samples from the persons tested may be obtained from any source including blood, a tissue sample, amniotic fluid, a chorionic villus sampling, cerebrospinal fluid, and urine.

The present invention includes but is not limited to the examples of proteins encoded by genes involved in folate, cobalamin and pyridoxine metabolism compiled in Tables 2–7 in the Detailed Description of the Invention, below. For certain genes nucleic acid and/or amino acid sequence data is also provided. These genes and related sequence data are solely intended as examples of genes that are suitable to be used in the methods described herein. Such sequence data can be used for carrying out the genetic analysis of the present invention. However, the present invention is not intended to be limited in any way to such lists of proteins or the related sequence data.

It is further contemplated by the present invention to provide methods that include the testing for a genetic mutations in individual genes involved in folate and cobalamin metabolism and/or in individual combinations of such genes (e.g., methylenetetrahydrofolate reductase gene and methionine synthase). In addition, all possible combinatorials, and permutations of such genes including a constellation comprising all of the genes involved in folate, pyridoxine, and cobalamin metabolism is envisioned by the present invention. Alternatively, a constellation of genes in which any one or more genes can be excluded from those tested is also contemplated by the present invention (for example, a given constellation of genes can include genes encoding all of the proteins in Table 2 and 4 except the folate receptor 2-like protein). Thus all of such possible constellations are envisioned by, and are therefore part of the present invention.

The present invention also provides DNA polymorphisms that can be used as genetic explanatory factors in the present invention. One such embodiment is a nucleic acid encoding a genetic variant of human dihydrofolate reductase comprising a nucleotide sequence having a 19 base-pair deletion spanning nucleotides 540 to 558 of the nucleotide sequence of SEQ ID NO:41. In a preferred embodiment the nucleic acid has the nucleotide sequence of SEQ ID NO:42.

The present invention also includes primers. One such embodiment is a PCR primer that can be used to distinguish SEQ ID NO:42 from SEQ ID NO:41. Another embodiment is a PCR primer that can be used to distinguish SEQ ID NO:42 from SEQ ID NO:45. These primers are useful for identifying the 19 base-pair deletion spanning nucleotides 540 to 558 of the nucleotide sequence of SEQ ID NO:41 (see Example 2). In a particular embodiment, the PCR primer comprises 8 to 100 and preferably 10 to 50 consecutive nucleotides from the nucleotide sequence of SEQ ID NO:41. In another embodiment the PCR primer comprises 8 to 100 and preferably 10 to 50 consecutive nucleotides from the nucleotide sequence of the complementary strand of SEQ ID NO:41. In still another embodiment the PCR primer comprises 8 to 100 and preferably 10 to 50 consecutive nucleotides from the nucleotide sequence of SEQ ID NO:42. In yet another embodiment the PCR primer comprises 8 to 100 and preferably 10 to 50 consecutive nucleotides from the nucleotide sequence of the complementary strand of SEQ ID NO:42. In still another embodiment the PCR primer comprises 8 to 100 and preferably 10 to 50 consecutive nucleotides from the nucleotide sequence of SEQ ID NO:45. In yet another embodiment the PCR primer comprises 8 to 100 and preferably 10 to 50 consecutive nucleotides from the nucleotide sequence of the complementary strand of SEQ ID NO: 45.

In a particular embodiment the PCR primer comprises 8 to 100 and preferably 10 to 50 consecutive nucleotides from nucleotides 350 to 530 of SEQ ID NO:41. In a preferred embodiment of this type, the PCR primer has the nucleotide sequence of CTAAACTGCATCGTCGCTGTG (SEQ ID NO:38). In another particular embodiment the PCR primer comprises 8 to 100 and preferably 10 to 50 consecutive nucleotides from the complementary strand of nucleotides 550 to 850 of SEQ ID NO:41. In preferred embodiment of this type, the PCR primer comprises 8 to 100 and preferably 10 to 50 consecutive nucleotides from the complementary strand of nucleotides 570 to 690 of SEQ ID NO:41. In a particular embodiment, the PCR primer has the nucleotide sequence of AAAAGGGGAATCCAGTCGG (SEQ ID NO:39).

The present invention also provides a nucleic acid that hybridizes under standard hybridization conditions to the nucleotide sequence ACCTGGGCGGGACGCGCCA (SEQ ID NO: 40). In another embodiment the nucleic acid hybridizes under standard hybridization conditions to the nucleotide sequence complementary to SEQ ID NO:40. In yet another embodiment the nucleic acid hybridizes under standard hybridization conditions to the nucleotide sequence ACCTGGGCGGGACGCGCC (SEQ ID NO:46). In yet another embodiment the nucleic acid hybridizes under standard hybridization conditions to the nucleotide sequence complementary to SEQ ID NO: 46. In a particular embodiment the nucleic acid consists of 9 to 96 nucleotides. In another embodiment the nucleic acid consists of 12 to 48 nucleotides. In still another embodiment the nucleic acid consists of 15 to 36 nucleotides. In a preferred embodiment the nucleic acid consists of 17 to 20 nucleotides.

The present invention also provides a nucleic acid that hybridizes to the nucleotide sequence of SEQ ID NO:41, but not to the nucleotide sequence of SEQ ID NO:42 when the hybridization is performed under identical conditions. In a particular embodiment the nucleic acid comprises the nucleotide sequence of CCCACGGTCGGGGTACCTGGGCGGGACGCGCCAGGCCGACTCCCGGCGA (SEQ ID NO:29). The present invention further provides a nucleic acid that hybridizes to the nucleotide sequence of SEQ ID NO:42, but not to the nucteotide sequence of SEQ ID NO:41 when the hybridization is performed under identical conditions. In a particular embodiment the nucleic acid comprises the nucleotide sequence of CCCACGGTCGGGGTGGCCGACTCCCGGCGA (SEQ ID NO:37).

In a related embodiment the present invention provides an isolated nucleic acid that hybridizes to the complementary strand of the nucleotide sequence of SEQ ID NO:42, but not to the complementary strand of the nucleotide sequence of SEQ ID NO:41 when the hybridization is performed under identical conditions. In still another embodiment the nucleic acid hybridizes to the nucleotide sequence of SEQ ID NO:41, but not to the nucleotide sequence of SEQ ID NO:42 when the hybridization is performed under identical conditions. In still another embodiment the nucleic acid hybridizes to the complementary strand of the nucleotide sequence of SEQ ID NO:41, but not to the complementary strand of the nucleotide sequence of SEQ ID NO:42 when the hybridization is performed under identical conditions.

The present invention also provides a nucleic acid that hybridizes to the nucleotide sequence of SEQ ID NO:42, but not to the nucleotide sequence of SEQ ID NO:45 when the hybridization is performed under identical conditions. In a related embodiment the present invention provides an isolated nucleic acid that hybridizes to the complementary strand of the nucleotide sequence of SEQ ID NO:42, but not to the complementary strand of the nucleotide sequence of SEQ ID NO:45, when the hybridization is performed under identical conditions. In still another embodiment the nucleic acid hybridizes to the nucleotide sequence of SEQ ID NO:45, but not to the nucleotide sequence of SEQ ID NO:42 when the hybridization is performed under identical conditions. In still another embodiment the nucleic acid hybridizes to the complementary strand of the nucleotide sequence of SEQ ID NO:45, but not to the complementary strand of the nucleotide sequence of SEQ ID NO: 42 when the hybridization is performed under identical conditions.

The present invention also provides for the use of the nucleic acids of the present invention (as well as other nucleic acids which can be used to identify DNA polymorphisms in the alleles of the genes involved in folate, pyridoxine, and/or cobalamin metabolism) in the methods of the present invention for identifying, diagnosing, preventing and/or treating individuals.

In methods of estimating the susceptibility due to genetic or genetic and environmental factors for an individual to have or to develop a developmental disorder or to have offspring that develop a developmental disorder, and for the corresponding methods of generating genetic, or genetic and environmental reference datasets, the present invention provides a step of analyzing nucleic acids and/or proteins from biological samples. In one particular embodiment, the assaying for the presence of the genetic variant of human dihydrofolate reductase having a nucleotide sequence with a 19 base-pair deletion spanning nucleotides 540 to 558 of the nucleotide sequence of SEQ ID NO:41 is included as part of this analysis. This genetic variant of human dihydrofolate reductase becomes a genetic explanatory variable.

Determining if the biological sample contains the genetic variant of human dihydrofolate reductase having a nucleotide sequence with a 19 base-pair deletion spanning nucleotides 540 to 558 of the nucleotide sequence of SEQ ID NO:41 can be performed by any appropriate method including PCR, special PCR, RT PCR, RFLP analysis, SSCP, and FISH.

In addition, all of the nucleic acids of the present invention including cDNA or genomic DNA can be placed into expression vectors operably associated with an expression control sequence. Alternatively, when the nucleic acid is part of an expression control sequence, the nucleic acid and/or the expression control sequence can be placed into an expression vector to control the expression of a coding sequence, such as a reporter gene. Such expression vectors can then be placed into either eukaryotic or prokaryotic host cells and expressed. The host cells comprising the expression vectors are also part of the present invention. In addition, when the nucleic acid includes a coding sequence or a part of a coding sequence, the present invention includes methods of purifying the gene products from the coding sequence or part thereof, and the purified gene products themselves.

Accordingly, it is a principal object of the present invention to provide a method for identifying an individual that is genetically inclined to develop a developmental disorder or disease.

It is a further object of the present invention to provide a method for identifying an individual that is genetically inclined to develop schizophrenia.

It is a further object of the present invention to provide a method for identifying an individual that is genetically inclined to have offspring having a developmental disorder.

It is a further object of the present invention to provide a method of diagnosing schizophrenia.

It is a further object of the present invention to provide a method of treating developmental disorders such as schizophrenia.

It is a further object of the present invention to provide a method for monitoring the treatment of the developmental disorder.

It is a further object of the present invention to provide a method for ameliorating the effect of a defect in folate, pyridoxine or cobalamin metabolism on a fetus due to the genetic or environmental status of a pregnant woman.

It is a further object of the present invention to provide a method of treating a patient who is genetically inclined to develop a developmental disorder such as schizophrenia.

It is a further object of the present invention to provide a method of overcoming a nutritional lack of folate, cobalamin or pyridoxine of a pregnant woman to prevent the development of the corresponding fetus developing a developmental disorder.

Other objects and advantages will become apparent to those skilled in the art from a review of the ensuing description.

These and other aspects of the present invention will be better appreciated by reference to the following drawings and Detailed Description.

BRIEF DESCRIPTION OF THE DRAWINGS

FIG. 1 shows primers for PCR amplification of the dihydrofolate reductase (DHFR) deletion polymorphism region.

FIG. 3 shows the sequences of PCR amplification products in the Region of the DHFR polymorphism region. * is explained in Text, see Example 2.

FIG. 4A is a nucleotide sequence of the wild type human DHFR, (SEQ ID NO:41) from Yang et al., *J. Mol. Biol.* 176:169–187 (1984), GeneBank accession no: X00855. The start codon is in bold.

FIG. 4B is the same nucleotide sequence as that of FIG. 4A except the deletion of the 19 nucleotides due to the DHFR deletion polymorphism, (SEQ ID NO: 42).

DETAILED DESCRIPTION OF THE INVENTION

Figure 2:
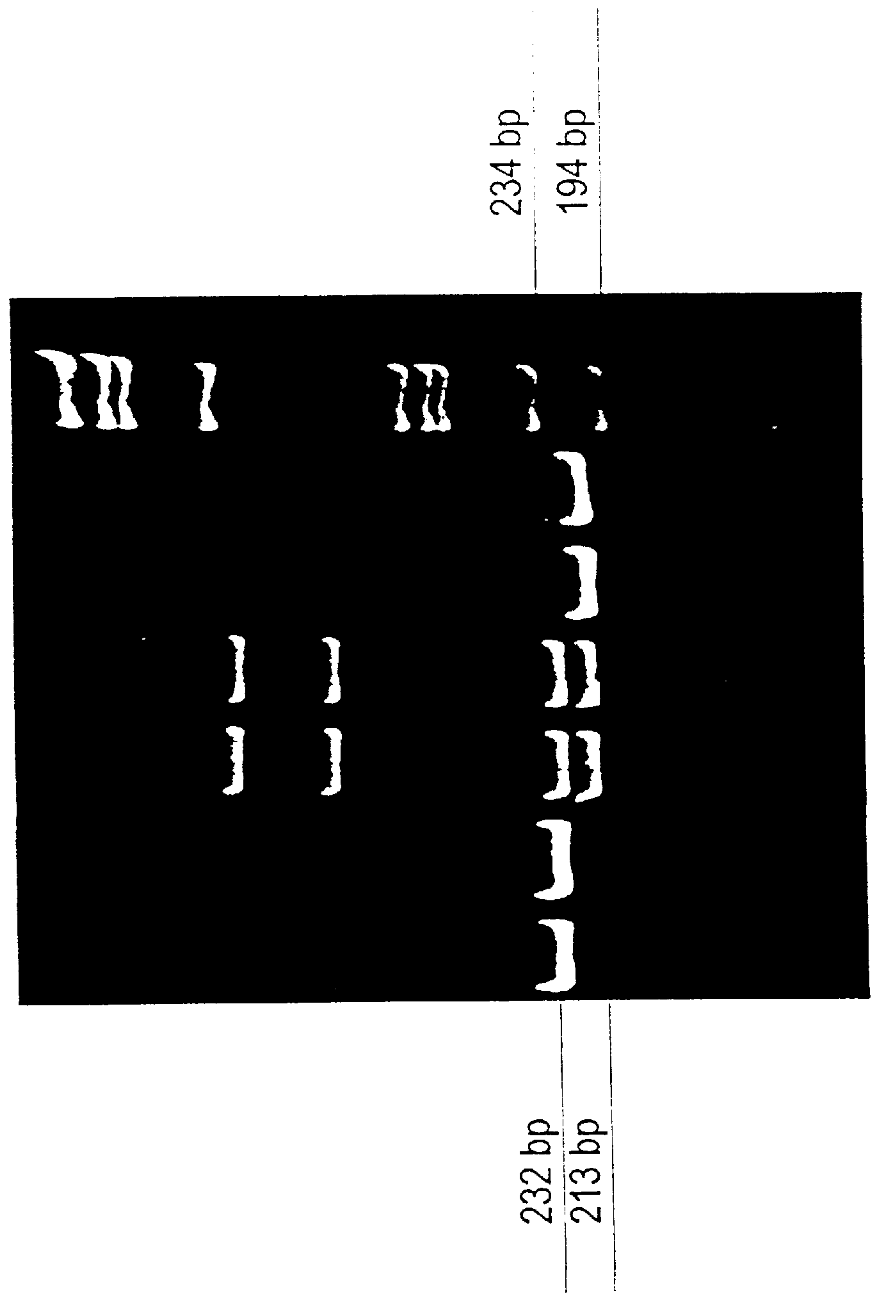
FIG. 2 shows the genotypes of the DHFR 19 basepair deletion by non-denaturing polyacrylamide gel electrophoresis. Lanes 1 and 2 show genotypes 1,1. Lanes 3 and 4 show genotypes 1, 2. Lanes 5 and 6 show genotypes 2,2. Lane 7 shows phiX174 RF DNA/HaeIII size markers from BRL Life Technologies.

The present invention in its broadest embodiment provides a method of diagnosing, preventing and/or treating specific physiologicalldevelopmental disorders. Such physiological/developmental disorders include schizophrenia, spina bifida cystica, Tourette's syndrome, bipolar illness, autism, conduct disorders, attention deficit disorder, obsessive compulsive disorder, chronic multiple tic syndrome and learning disorders such as dyslexia.

A particular aspect of the present invention provides methodology for diagnosing, preventing and/or treating a developmental disorder such as schizophrenia. Such methodology is premised on the correlation between abnormalities in folate, cobalamin, and/or pyridoxine metabolism in an individual and/or the mother of an individual and the occurrence of the developmental disorder, e.g., schizophrenia in the individual. Further, the present invention provides a framework (i.e., the gene-teratogen model, and the DNA Polymorphism-Diet-Cofactor-Development both of which are described in detail below) which fully explain the rationale for the correlation, though the ultimate usefulness of the methods of the present invention are independent of any particular model.

Within this context, the DNA Polymorphism-Diet-Cofactor-Development model maintains that a developmental disorder such as schizophrenia results in part from developmental brain damage sustained in utero due to maternal dietary deficiency of folate, pyridoxine or cobalamin potentiated by the aggregate effect of minor defects of folate, pyridoxine or cobalamnin genes. The maternal damage to the fetus can result in part from insufficiency of the folate, pyridoxine and cobalarnin themselves and/or from resulting effects such as immune deficiency and maternal teratogens, e.g. hyperhomocysteinemia. Genes from either parent acting in the fetus may modify these damaging effects as exemplified in the gene-teratogen model, below.

As described herein the present invention can be practiced on a case by case basis, or alternatively, it can be used in the screening of the general population, or within any particular subgroup, such as newborns (as is presently performed in the diagnosis and treatment of hyperphenylalaninemia).

Therefore, if appearing herein, the following terms shall have the definitions set out below.

As used herein a "gene involved in folate, pyridoxine, or cobalamin metabolism" is a gene that encodes a peptide or protein that plays a role in a pathway involved in either folate, pyridoxine, or cobalamin metabolism. An incomplete listing of examples of such proteins is given in Tables 2–7.

As used herein the term "individual" includes a fetus, infant, child, adolescent, and adult. Therefore, as used herein, an individual originates at conception.

As used herein an individual with a susceptibility for "having offspring that develop a developmental disorder" is meant to be indicative of the susceptibility of the offspring of that individual to develop the developmental disorder and is not in any way meant to be indicative of the susceptibility of the individual to have offspring.

The term "proband" as used herein is operationally defmed by Table 8 along with the accompanying explanatory information (see, Example 1). For most purposes, the proband can be considered the central figure in the familial analysis, the remaining individuals in the family being designated as "blood relatives". There are three types of probands: (1) an "affected proband" i.e., an individual that is believed to have a developmental disorder ; (2) a "control proband" an individual that is believed not to have a developmental disorder; and (3) a "diagnostic proband" i.e., an individual being diagnosed.

As used herein a "blood relative" of an individual is a relative that is related to the individual in a genetic sense. Blood relatives can include mothers, fathers, children, uncles, aunts, brothers, sisters, and grandparents. Preferably a blood relative is a parent, a sibling, or a grandparent. Adopted relatives, step-parents, relatives through marriage and the like are not blood relatives. Therefore, as used herein, the terms "mother", "father", "sibling", "grandparent", "grandfather" and "grandmother" are indicative of blood relationships.

As used herein a "mate of an individual" is a person whose genetic material is combined with that of the individual for the conception of the offspring in question.

As used herein the term "schizophrenia" describes a disorder that is at least partially due to one or more genetic mutations or polymorphisms in one or more genes involved in folate, cobalamin or pyridoxine metabolism in an individual that is schizophrenic and/or to one or more genetic mutations or polymorphisms in one or more genes involved in folate, cobalamin or pyridoxine metabolism in the mother of that individual.

As used herein an individual is "schizophrenic" when the individual displays symptoms that would be accepted by an experienced psychiatrist to merit a diagnosis of schizophrenia. Such a diagnosis is based, at least in part, on the currently evolving guidelines for the diagnosis of schizophrenia which are listed in the successive editions of Diagnostic and Statistical Manual for Mental Disorders, put out by the American Psychiatric Association. The current edition is the DSM, Fourth Edition (1994).

As used herein the terms "spina bifida cystica", "Tourette's syndrome", "bipolar illness", "autism", "conduct disorder", "attention deficit disorder", "obsessive compulsive disorder", "chronic multiple tic syndrome" and "learning disorders"such as "dyslexia"describe disorders which display symptoms that would be accepted by an experienced psychiatrist to merit a diagnosis of that disorder. Such a diagnosis is based, at least in part, on the currently evolving guidelines which are listed in the successive editions of Diagnostic and Statistical Manual for Mental Disorders, put out by the American Psychiatric Association. The current edition is the DSM, Fourth Edition (1994).

As used herein the term "teratogenic locus" indicates one or more alleles that act in a pregnant woman to cause an intrauterine teratogenic effect on the fetus.

As used herein the terms "specificity locus" or "modifying locus" are used interchangeably and are indicative of one or more alleles that can act during pregnancy and/or after birth to prevent, modify, and/or ameliorate the teratogenic effect of the teratogenic locus.

As used herein a "constellation of genetic mutations" is the set of genetic risk factor mutations that is present in a proband and relatives of the proband. One example of a constellation of genetic mutations is shown in a line of Table 8, below.

As used herein a "risk factor" is a teratogen or substance (including a defective gene) that can lead to a teratogenic effect that is present or suspected of being present in a tissue sample or body fluid of an individual's mother during the individual's gestation and/or present or suspected of being present in a tissue sample or body fluid of the individual.

As used herein a "genetic risk factor" is used interchangeably with the term "genetic explanatory variable" and is a genetic mutation and/or polymorphism that causes or potentially can cause the formation of and/or lead to the development of a risk factor in an individual or the individual's mother during gestation.

As used herein an "environmental risk factor" is used interchangeably with the term "environmental explanatory variable" and is an environmental factor that causes or potentially can cause the formation of and/or lead to the development of a risk factor in an individual or the individual's mother during gestation.

As used herein an "explanatory variable" is either an "environmental explanatory variable" or a "genetic explanatory variable" or the variable defined by their interaction or any combination of the above.

Enzymes whose deficiency may raise plasma homocysteine include methylenetetrahydrofolate reductase (MTHFR), methionine synthase, and folate receptors/transport proteins/binding proteins (as well as all of the proteins listed in Tables 2–7 below).

The current (developmental) model for schizophrenia is that genetic and environmental factors cause brain damage in a fetus that later develops schizophrenia. However, the genetic and environmental factors have not been identified. Also, extensive linkage and association studies have failed to identify genes determining schizophrenia. The reasons usually given for this difficulty include: (i) locus heterogeneity, i.e., more than one gene locus is involved, perhaps many gene loci each with a small effect; (ii) the mode of inheritance of schizophrenia is unknown; and (iii) an additional possible factor is that the frequency of the disease alleles may be high, thus greatly reducing the power of linkage studies.

The DNA Polymorphism-Diet-Cofactor-Development model explains all of these difficulties and at the same time proposes a unified metabolic abnormality. The unified metabolic abnormality is: (a) ENVIRONMENTAL, i.e., due to a folate/cobalamin/pyridoxine deficiency caused by either decreased ingestion or increased requirement during pregnancy; (b) GENETIC, i.e., due to a folate/cobalarnin/pyridoxine genetic defect caused by the aggregate effect of multiple mutations of folate/cobalamin/pyridoxine genes each individually having a small effect; and (c) the interaction of the folate/cobalamin/pyridoxine environmental and genetic factors (indicated above) to cause other harmful effects such as maternal teratogens and immune deficiency during gestational development. Different gene loci and different combinations of gene loci will be involved in different patients and different families. The problem of locus heterogeneity is addressed by the hypothesis that the folate/cobalamin/pyridoxine genetic defect is the aggregate effect of multiple mutations of folate/cobalamin/pyridoxine genes each of which have a relatively small effect.

The problem of mode of inheritance is addressed by the gene-teratogen model. The gene-teratogen model describes the special features of genes acting in utero; both teratogenic and modifying of specificity loci may be involved. If these effects are not taken into account, the assignment of affection status in schizophrenia pedigrees is inaccurate. Assignment of affection status is a key element in defining the mode of inheritance for all kinds of linkage mapping. Failure to assign the correct mode of inheritance is another factor that has made the linkage studies very difficult.

Finally, the DNA Polymorphism-Diet-Cofactor-Development model proposes that some of the genetic factors for schizophrenia are common in the population. In fact, subclinical deficiency of folate, pyridoxine, and cobalamin is common in the population and common among pregnant women as well. Pregnancy further increases the requirement for folate, pyridoxine, and cobalamin. Common genetic polymorphisms of folate and cobalamin genes are also known, some of them functional. Common genetic risk factors tend to be functional polymorphisms and/or mutant alleles that individually have small effects. Otherwise, they would be largely eliminated from the population by natural selection and would not be common. High disease allele frequency is yet another factor that greatly diminishes the power of a linkage study.

Besides explaining the difficulties with current linkage studies, the DNA Polymorphism-Diet-Cofactor-Development model explains all of the unusual biological and epidemiological features of schizophrenia: e.g. the decreased amount of gray matter in brain areas, the unusual birth-month effect, the geographical differences in incidence, the socioeconomic predilection, the association with obstetrical abnormalities (low birth weight and prematurity), and the association with famine and viral epidemics. Consistently, genetic linkage and cytogenetic studies in schizophrenia have implicated various chromosome regions, some of them containing folate, pyridoxine, and cobalamin genes including dihydrofolate reductase, thymidylate synthase, and transcobalarnin II. The DNA Polymorphism-Diet-Cofactor-Development model predicts that folate, pyridoxine, or cobalamin gene mutations have a high frequency in schizophrenia patients or family members.

Furthermore, mothers of schizophrenics are predicted to be particularly susceptible to producing one or more teratogens during pregnancy.

The present invention therefore provides methods for: (a) Diagnostic testing of schizophrenia by identifying a folate, pyridoxine, or cobalamin gene mutation or constellation of mutations in the patient, mother, and father. (b) Prevention of schizophrenia by diagnostic testing in families already affected by schizophrenia or by diagnostic population screening for folate mutations and identifying couples at risk for producing schizophrenic offspring. These pregnancies can be further monitored for risk factors, e.g. dietary folate/pyridoxine/cobalamin, plasma folate/pyridoxine/cobalamin, or red blood cell folate; plasma homocysteine or other teratogens. (c) Therapy for schizophrenia, e.g., treating the pregnant mother with folate, pyridoxine, cobalamin or other agents. The treatment can be monitored at regular intervals to determine the effect of therapy. (d) Presymptomatic treatment of schizophrenia on young children found to be susceptible to schizophrenia by diagnostic testing for folate gene mutations and other risk factors can also be treated with methylfolate or related therapeutic modalities to forestall the appearance of schizophrenia symptoms in adolescence or adulthood.

Empirical studies with methylfolate treatment of schizophrenia have shown modest clinical improvement. The DNA Polymorphism-Diet-Cofactor-Development model gives a rationale for such therapy as well as for intensive testing of related therapeutic modalities. Genetic testing will need to be carried out in such patients to gauge their likelihood of responding to therapy. In addition, the DNA Polymorphism-Diet-Cofactor-Development model gives direction and impetus toward uncovering the mechanism of fetal brain damage leading to schizophrenia.

Diagnostic testing for schizophrenia can involve testing not just the patient, but mother and father as well, for not just one factor but multiple genetic factors. For example, data for two gene loci (both folate-related genes) were used in Example 2. In this case, there were only four explanatory variables for each comparison.

In addition, risk factors appearing only during pregnancy may play a role, e.g. dietary folate which can be further monitored during the pregnancy. In certain instances, genotype data can be used as the sole explanatory variables, particularly in the case when no environmental explanatory variables are known. In such a case, the predicted probabilities will be only for the genetic component of the proband's risk of schizophrenia. In addition, schizophrenia mothers, fathers, and sibs do not necessarily have to come from the same families as the schizophrenia probands, as described in Example 2.

Of course certain genetic factors will turn out to be more common than others. This may simplify testing somewhat. Also some genetic factors may operate chiefly in the mother, while others will operate chiefly in the schizophrenic patient. This may also simplify testing. There are some approaches to assessing risk factors during a past pregnancy, e.g. current dietary history as an indicator of past diet, methionine loading as in indicator of how susceptible a mother is to raising her plasma homocysteine, assessment of other risk factors besides folate metabolism that may affect pregnancy outcome. Procedures including all of these variables are both envisioned and included in the present invention.

Thus the present invention provides a method of diagnosis of schizophrenia. In one aspect of the invention, diagnostic testing for genetic susceptibility to schizophrenia determines the probability that the proband is affected with schizophrenia due to genetic factors. This is carried out by genetic testing of a patient suspected of having schizophrenia and/or whatever informative relatives are available, e.g. mother, father, sibs, or children. The genotypes of certain folate and/or cobalamin and/or pyridoxine gene mutations or constellation of mutations (folate and/or cobalamin and/or pyridoxine gene mutations) are determined for each individual.

Since the abnormal phenotype of schizophrenia can be determined by both genetic and environmental factors and since other genetic factors besides folate/cobalamin/pyridoxine gene mutations may be involved, the presence of folate/cobalamin/pyridoxine gene mutations may be neither necessary nor sufficient to cause schizophrenia. Thus, an unaffected individual may have the same genetic risk factors as an affected individual but may lack sufficient environmental factors to cause the abnormal clinical disease. Also, an affected individual may lack folate/cobalamin/pyridoxine gene mutations but may have other related or non-related genetic risk factors that caused the schizophrenia.

Therefore folate/cobalamin/pyridoxine gene mutations are used as explanatory variables (genetic risk factors) to calculate the predicted probability that an individual has genetic susceptibility to schizophrenia due to these mutations. Genetic variation can be expected to account for approximately about half of the risk of developing schizophrenia since the concordance rate in identical twins has been estimated to be about 50%. The other half of the risk results from environmental factors due to their different positions in the uterus and to differences in the blood supply. The use of environmental factors as additional explanatory variables enhances this probability calculation, although this environmental data is more difficult to gather. Together, using both genetic and environmental explanatory variables, the predicted probability that an individual is schizophrenic may approach 1.0.

One likely situation for the use of the present methodology is in the diagnosis of a patient that has developed a psychosis. In such a case, the clinician is likely to be interested in determining the probability that this individual has schizophrenia. The number of blood relatives (preferably first degree relatives) of the patient-to-be diagnosed, both unaffected and affected, could then be determined. The number of these who would contribute a blood sample for analysis, for example, could then be ascertained. It is preferable that the patient-to-be-diagnosed also contributes a blood sample, however in certain situations, this may not be an option. The availability of dietary and epidemiological information for environmental explanatory variables, especially from the patient and the mother, can also ascertained. Of course all relevant legal and ethical rules should be followed regarding informed consent for the genetic testing.

Biological samples such as tissue or fluid samples (e.g., 7 ml of blood in an EDTA-containing vacutainer, see Example 2, below), and obtainable environmental data from the patient and family members are then collected. DNA is extracted from the sample and genotypes for alleles of folate and/or cobalamin and/or pyridoxine genes are determined. The methods for genotyping depend upon the specific genetic markers used as explanatory variables. The methods for allele determination for two genetic markers are discussed in the Examples below.

Data of the genetic and environmental explanatory variables for the patient-to-be-diagnosed (proband) and participating family members are added to a reference data set preferably consisting of well-defined schizophrenia probands and family members, and control probands, and family members for whom data is available for many explanatory variables. As an approximation the control probands themselves also can be used as the controls for each proband family member class as shown in Example 2, below. Thus, as an approximation the control probands can be used as controls for the affected probands; and/or separately for the mothers of affected probands; and/or separately for the fathers of affected probands, etc. Another example of a use of the control probands is in the evaluation and/or analysis of a particular diagnostic proband. In this case, the approximation is obtained by adding the diagnostic proband to the group of affected probands and control probands.

A model is then created consisting of the explanatory variables actually available from specific patient-to-be diagnosed and family members participating in the testing. This new combined data set (reference data set and data from patient-to-be-diagnosed with participating family members) is analyzed by binary logistic regression (e.g., using a statistical software package such as the SAS System embodied in Example 1 below, though other programs may be used) for the model chosen giving the predicted probability that a proband is affected with schizophrenia for all of the probands including the patient-to-be-diagnosed.

In a particular embodiment the model is modified and the goodness of fit for the patient-to-be-diagnosed is checked. The predicted probability that the patient-to-be-diagnosed has schizophrenia is compared with a classification table generated from the model used to determine the likelihood of false positives and false negatives.

The predicted probability that the patient-to-be-diagnosed is affected with schizophrenia, with the likelihood of false positive or false negative result, can then be forwarded to the clinician.

The methods for determining an individual's risk for developing schizophrenia taught by the present invention can be used in a variety of settings. For example, the present invention also provides a therapy for schizophrenia. Empirical studies with methylfolate treatment of schizophrenia have shown modest clinical improvement. The DNA Polymorphism-Diet-Cofactor-Development model provides a rationale for such therapy as well as for intensive testing of related therapeutic modalities, e.g. other cofactors such as cobalamin or pyridoxine. In addition, the DNA Polymorphism-Diet-Cofactor-Development model gives direction and impetus toward uncovering the mechanism of fetal brain damage leading to schizophrenia. Of course such therapy also can be provided on a case by case basis in order to gauge the likelihood of the patient of responding to such therapy, with the methodology for diagnosis of the present invention enabling the skilled practitioner to assess that likelihood.

In addition, the present invention provides a method of identifying individuals that are likely to be aided by presymptomatic treatment for schizophrenia. For example, young children found to have a high risk for susceptibility to schizophrenia by diagnostic testing can be treated with methylfolate or related therapeutic modalities to forestall the appearance of schizophrenia symptoms in adolescence or adulthood. The present invention further provides methodology for diagnostic testing for specific families already affected by schizophrenia.

The present invention further provides methodology for population screening for folate/cobalamin/pyridoxine mutations to help identify couples at risk for producing schizophrenic offspring. Subsequent or concurrent pregnancies can then be monitored for environmental risk factors, and treated with folate, cobalamin, pyridoxine or other agents and monitored at intervals for the effect of therapy. Such monitoring can include measuring levels of folate, cobalamin, pyridoxine or homocysteine in a particular tissue and/or fluid sample, such as blood.

Since schizophrenia is a developmental disorder, it is likely that these same risk factors discussed here for schizophrenia could play a role in other developmental disorders including spina bifida cystica, Tourette's syndrome, learning disorders including dyslexia, conduct disorder, attention-deficit hyperactivity disorder, bipolar illness, autism, and obsessive-compulsive disorder. Interestingly, the mode of inheritance of these disorders, like that of schizophrenia, has been difficult to determine despite the fact that a genetic component to the etiology of each has been documented. Therefore, methodology analogous to that exemplified herein for schizophrenia can be readily adapted for diagnosing and/or treating other such developmental disorders.

Nucleic Acids

In accordance with the present invention there may be employed conventional molecular biology, microbiology, and recombinant DNA techniques within the skill of the art. Such techniques are explained fully in the literature. See, e.g., Sambrook, Fritsch & Maniatis, *Molecular Cloning: A Laboratory Manual*, Second Edition (1989) Cold Spring Harbor Laboratory Press, Cold Spring Harbor, New York (herein "Sambrook et al., 1989"); *DNA Cloning: A Practical Approach*, Volumes I and II (D. N. Glover ed. 1985); *Oligonucleotide Synthesis* (M. J. Gait ed. 1984); *Nucleic Acid Hybridization* [B. D. Hames & S. J. Higgins eds. (1985)]; *Transcription And Translation* [B. D. Hames & S. J. Higgins, eds. (1984)]; *Animal Cell Culture* [R. I. Freshney, ed. (1986)]; *Immobilized Cells And Enzymes* [IRL Press, (1986)]; B. Perbal, *A Practical Guide To Molecular Cloning* (1984); F. M. Ausubel et al. (eds.), *Current Protocols in Molecular Biology*, John Wiley & Sons, Inc. (1994)].

A "nucleic acid molecule" refers to the phosphate ester polymeric form of ribonucleosides (adenosine, guanosine, uridine or cytidine; "RNA molecules") or deoxyribonucleosides (deoxyadenosine, deoxyguanosine, deoxythymidine, or deoxycytidine; "DNA molecules"), or any phosphoester analogs thereof, such as phosphorothioates and thioesters, in either single stranded form, or a double-stranded helix. Double stranded DNA-DNA, DNA-RNA and RNA-RNA helices are possible. The term nucleic acid molecule, and in particular DNA or RNA molecule, refers only to the primary and secondary structure of the molecule, and does not limit it to any particular tertiary forms. Thus, this term includes double-stranded DNA found, inter alia, in linear or circular DNA molecules including restriction fragments, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). A "recombinant DNA molecule" is a DNA molecule that has undergone a molecular biological manipulation.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength (see Sambrook et al., supra). The conditions of temperature and ionic strength determine the "stringency" of the hybridization. High stringency hybridization conditions correspond to 50% formarnide, 5× or 6×SSC. Hybridization requires that the two nucleic acids contain complementary sequences, although depending on the stringency of the hybridization, mismatches between bases are possible. The appropriate stringency for hybridizing nucleic acids depends on the length of the nucleic acids, the GC percentage, and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived (see Sambrook et al., supra, 9.50–10.51). For hybridization with shorter nucleic acids, i.e., oligonucleotides, the position of mismatches becomes more important, and the length of the oligonucleotide determines its specificity (see Sambrook et al., supra, 11.7–11.8). Preferably a minimum length for a hybridizable nucleic acid (e.g., a nucleotide probe or primer such as a PCR or RT-PCR primer) is at least about 12 nucleotides; preferably at least about 18 nucleotides; and more preferably the length is at least about 27 nucleotides; and most preferably at least about 36 nucleotides. Specific probes and primers that can be used to distinguish specific variants of the nucleic acids encoding the proteins involved in folate, pyridoxine, and/or cobalamin metabolism are also part of the present invention.

Such nucleotide probes and primers can be labeled or used to label complementary DNA (where appropriate) by any number of ways well known in the art including using a radioactive label, such as $^3H$, $^{14}C$, $^{32}P$, or $^{35}S$, a fluorescent label, a boron label [U.S. Pat. No: 5,595,878, Issued Jan. 21, 1997 and U.S. Pat. No: 5,876,938, Issued Mar. 2, 1999 which are incorporated by reference in their entireties], and enzymatic tags such as urease, alkaline phosphatase or peroxidase. In the case of enzyme tags, colorimetric indicator substrates are known which can be employed to provide a means visible to the human eye or spectrophotometrically, to identify specific hybridization with complementary nucleic acid-containing samples.

In a specific embodiment, the term "standard hybridization conditions" refers to a $T_m$ of 55° C., and utilizes conditions as set forth above e.g., 5×SSC. In a preferred embodiment, the $T_m$ is 60° C.; in a more preferred embodiment, the $T_m$ is 65° C.

A DNA "coding sequence" is a double-stranded DNA sequence which is transcribed and translated into a polypeptide in a cell in vitro or in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, eDNA from eukaryotic mRNA, genomic DNA sequences from eukaryotic (e.g., mammalian) DNA, and even synthetic DNA sequences. If the coding sequence is intended for expression in a eukaryotic cell, a polyadenylation signal and transcription termination sequence will usually be located 3' to the coding sequence.

"Transcriptional and translational control sequences" are DNA regulatory sequences, such as promoters, enhancers, terminators, and the like, that provide for the expression of a coding sequence in a host cell. In eukaryotic cells, polyadenylation signals are control sequences.

A "promoter sequence" is a DNA regulatory region capable of binding RNA polymerase and initiating transcription of a downstream (3' direction) coding sequence. For purposes of defming the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined for example, by mapping with nuclease S1), as well as protein binding domains (consensus sequences) responsible for the binding of RNA polymerase.

A "signal sequence" is included at the beginning of the coding sequence of a protein to direct the protein to a particular site/compartment in the cell such as the surface of a cell. This sequence encodes a signal peptide, N-terminal to the mature polypeptide, that directs the host cell to translocate the polypeptide. The term "translocation signal sequence" is used herein to refer to this sort of signal sequence. Translocation signal sequences can be found associated with a variety of proteins native to eukaryotes and prokaryotes, and are often functional in both types of organisms.

Identification of Genetic Mutations

A biological sample can be obtained from an individual and/or a blood relative of the individual, and from appropriate controls, using a sample from any body component including tissue punches, body fluids, and hair, as long as the biological sample contains nucleic acids and/or proteins/peptides. Thus the DNA, mRNA, proteins or peptides of the biological sample can be used to identify mutations and/or variants in genes involved in folate, pyridoxine, or cobalamine metabolism. The present invention therefore includes methods of detecting and quantifying these nucleic acids and/or proteins/peptides that can be used to identify genetic risk factors.

In a particular embodiment the DNA is extractable. A particularly useful source of DNA is blood. For example, 2.5–40 mls of blood can be collected in a vacutainer containing EDTA. The blood sample is placed on ice and then centrifuged to separate plasma, red cells, and buffy coat. The separated fractions are then frozen at −80° C.

The DNA can be isolated from the buffy coat by a number of procedures well known in the art including using a QIAmp column DNA extraction procedure or the QIAGEN Genomic-tip method. The isolated DNA can be digested with a series of restriction enzymes, for example, and then the digested products can be hybridized with one or more particular nucleic acid probes designed from a particular gene to identify the gene and preferably to test for particular genetic mutations.

Preferably the genomic DNA can be amplified by PCR using appropriate primer pairs such as the primer pairs for the MTHFR or DHFR genes which were used in the Example below. The PCR amplified product can be sequenced directly, or alternatively be digested with one or more appropriate restriction enzymes. The resulting digested products can be separated e.g., by column chromatography, or preferably by polyacrylamide or agarose gel electrophoresis. The isolated digestion products can be compared e.g., by previously determined restriction maps, and/or alternatively, the digestion products can be sequenced directly. Alternatively, as in the case of DHFR, genetic polymorphisms can be detected through the use of restriction enzymes.

Although a restriction map of a gene is sufficient for the employment of the methods disclosed herein, in preferred embodiments the nucleotide sequences of the genes used in the testing steps are known. To this end a large sampling of such sequences are provided in Tables 2–7. (These sequences may also be used in the design of restriction maps.) Thus, initially each gene whether used separately or used in a constellation of genes is characterized by the sequencing of the wild type gene, preferably including the coding regions, introns, control sequences, and other non-coding regions. In addition, mutations of such genes found in the general population can also be characterized. With the recent advances in the sequencing of the human genome the present invention contemplates that additional sequence information will become publicly available, particularly with regard to mutations in relevant introns, and control sequences etc. which are not available in cDNA libraries. Such sequence information is fully envisioned to be incorporated into the on-going compilations of relevant DNA sequence databases of the present invention, as well as for its parallel use in the general methodology described herein. Thus DNA or mRNA or cDNA made from the mRNA can be used to identify mutations and/or variants in genes involved in folate, pyridoxine, or cobalamine metabolism.

There are many methods currently known in the art to identify variant/mutant DNA, all of which may be used in the present invention (see e.g., internet address http://www.ich.bpmf.ac.uk/cmgs/mutdet.htm). Such methods include but in no way are limited to direct sequencing, array sequencing, matrix-assisted laser desorption/ionization time-of-flight mass spectrometry (Malditof) [Fitzgerald et al., *Ann. Rev. Biophy. Biomol. Struct*. 24:117–140 (1995)], Polymerase Chain Reaction "PCR", reverse-transcriptase Polymerase Chain Reaction "RT-PCR", RNAase protection assays, Array quantitation e.g., as commercially provided by Affymetrix, Ligase Chain Reaction or Ligase Amplification Reaction (LCR or LAR), Self-Sustained Synthetic Reaction (3SR/NASBA), Restriction Fragment Length Polymorphism (RFLP),Cycling Probe Reaction (CPR), Single-Strand Conformation Polymorphism (SSCP), heteroduplex analysis, hybridization mismatch using nucleases (e.g., cleavase), Southern, Northerns, Westerns, South Westerns, ASOs, Molecular beacons, footprinting, and Fluorescent In Situ Hybridization (FISH). Some of these methods are briefly described below.

PCR is a method for increasing the concentration of a segment of target sequence in a mixture of genomic DNA without cloning or purification. PCR can be used to directly increase the concentration of the target to an easily detectable level. This process for amplifying the target sequence involves introducing a molar excess of two oligonucleotide primers which are complementary to their respective strands of the double-stranded target sequence to the DNA mixture containing the desired target sequence. The mixture is denatured and then allowed to hybridize. Following hybridization, the primers are extended with polymerase so as to form complementary strands. The steps of denaturation, hybridization, and polymerase extension can be repeated in order to obtain relatively high concentrations of a segment of the desired target sequence. The length of the segment of the desired target sequence is determined by the relative positions of the primers with respect to each other, and, therefore, this length is a controllable parameter. Because the desired segments of the target sequence become the dominant sequences (in terms of concentration) in the mixture, they are said to be "PCR-amplified." [Mullis (U.S. Pat. No. 4,683,195) and Mullis et al. (U.S. Pat. No. 4,683,202)]

In Ligase Chain Reaction or Ligase Amplification Reaction (LCR or LAR) four oligonucleotides, two adjacent oligonucleotides which uniquely hybridize to one strand of target DNA, and a complementary set of adjacent oligonucleotides, which hybridize to the opposite strand are mixed and DNA ligase is added to the mixture. Provided that there is complete complementarity at the junction, ligase will covalently link each set of hybridized molecules. Importantly, in LCR, two probes are ligated together only when they base-pair with sequences in the target sample, without gaps or mismatches. Repeated cycles of denaturation, hybridization and ligation amplify a short segment of DNA. [Barany, Proc. Natl. Acad. Sci., 88:189 (1991); Barany, PCR Methods and Applic., 1:5 (1991); and Wu and Wallace, Genomics 4:560 (1989)] LCR has also been used in combination with PCR to achieve enhanced detection of single-base changes. Segev, PCT Public. No. W09001069 A1 (1990).

Self-Sustained Synthetic Reaction (3SR/NASBA) is a transcription-based in vitro amplification system [Guatelli et aL, *Proc. Natl. Acad. Sci*., 87:1874–1878, 7797 (1990); Kwok et al., *Proc. Natl. Acad Sci*., 86:1173–1177) that can exponentially amplify RNA sequences at a uniform temperature. The amplified RNA can then be utilized for mutation detection (Fahy et aL, *PCR Meth. Appl*., 1:25–33 (1991). In this method, an oligonucleotide primer is used to add a phage RNA polymerase promoter to the 5' end of the sequence of interest. In a cocktail of enzymes and substrates that includes a second primer, reverse transcriptase, RNase H, RNA polymerase and ribo-and deoxyribonucleoside triphosphates, the target sequence undergoes repeated rounds of transcription, cDNA synthesis and second-strand synthesis to amplify the area of interest. RFLP can be used to detect DNA polymorphisms arising from DNA sequence variation. This method consists of digesting DNA with one or more restriction endonucleases (e.g., EcoRI) and analyzing the resulting fragments by means of Southern blots [Southern, E., *Methods in Enzymology*, 69:152 (1980)], as further described by Botstein, et al., *Am. J Hum. Genet*., 32:314–331 (1980) and White, et al., *Sci. Am*., 258:40–48 (1988). Since a DNA polymorphism may create or delete a restriction site, the length of the corresponding restriction fragment with any given restriction enzyme could change. Once a difference in a restriction fragment length is identified it can be used to readily distinguish a particular polymorphism from the wild type DNA. Mutations that affect the recognition sequence of the endonuclease will preclude enzymatic cleavage at that site, thereby altering the cleavage pattern of that DNA. DNAs are compared by looking for differences in restriction fragment lengths. A technique for detecting specific mutations in any segment of DNA is described in Wallace, et al.,[*Nucl. Acids Res*., 9:879–894 (1981)]. It involves hybridizing the DNA to be analyzed (target DNA) with a complementary, labeled oligonucleotide probe. Due to the thermal instability of DNA duplexes containing even a single base pair mismatch, differential melting temperature can be used to distinguish target DNAs that are perfectly complementary to the probe from target DNAs that differ by as little as a single nucleotide. In a related technique, described in Landegren, et al., *Science,* 41:1077–1080 (1988), oligonucleotide probes are constructed in pairs such that their junction corresponds to the site on the DNA being analyzed for mutation. These oligonucleotides are then hybridized to the DNA being analyzed. Base pair mismatch between either oligonucleotide and the target DNA at the junction location prevents the efficient joining of the two oligonucleotide probes by DNA ligase.

When a sufficient amount of a nucleic acid to be detected is available, there are advantages to detecting that sequence directly, instead of making more copies of that target, (e.g., as in PCR and LCR). Most notably, a method that does not amplify the signal exponentially is more amenable to quantitative analysis. Even if the signal is enhanced by attaching multiple dyes to a single oligonucleotide, the correlation between the final signal intensity and amount of target is direct. Such a system has an additional advantage that the products of the reaction will not themselves promote further reaction, so contamination of lab surfaces by the products is not as much of a concern. Traditional methods of direct detection including Northern and Southern blotting and RNase protection assays usually require the use of radioactivity and are not amenable to automation. Recently devised techniques have sought to eliminate the use of radioactivity and/or improve the sensitivity in automatable formats.

One such example is the Cycling Probe Reaction (CPR) [Duck et al., BioTech., 9:142 (1990)]. CPR , uses a long chimeric oligonucleotide in which a central portion is made of RNA while the two termini are made of DNA. Hybridization of the probe to a target DNA and exposure to a thermostable RNase H causes the RNA portion to be digested. This destabilizes the remning DNA portions of the duplex, releasing the remainder of the probe from the target DNA and allowing another probe molecule to repeat the process. The signal, in the form of cleaved probe molecules, accumulates at a linear rate. While the repeating process increases the signal, the RNA portion of the oligonucleotide is vulnerable to RNases that may carried through sample preparation.

Single-Strand Conformation Polymorphism (SSCP) is based on the observation that single strands of nucleic acid can take on characteristic conformations in non-denaturing conditions, and these conformations influence electrophoretic mobility. [Hayashi, *PCR Meth. Appl.*, 1:34–38, (1991). The complementary strands assume sufficiently different structures that one strand may be resolved from the other. Changes in sequences within the fragment will also change the conformation, consequently altering the mobility and allowing this to be used as an assay for sequence variations (Orita, et al., *Genomics* 5:874–879, (1989). The SSCP process involves denaturing a DNA segment (e.g., a PCR product) that is labeled on both strands, followed by slow electrophoretic separation on a non-denaturing polyacrylaride gel, so that intra-molecular interactions can form and not be disturbed during the run. This technique is extremely sensitive to variations in gel composition and temnperature.

In Fluorescent In Situ Hybridization (FISH), specific probes are designed which can readily distinguish the wild-type gene from the variant/mutant gene. Such methodology allows the identification of a variant/mutant gene through in situ hybridization (U.S. Pat. No. 5,028,525, Issued Jul. 2, 1991; U.S. Pat. No. 5,225,326, Issued Jul. 6, 1993; and U.S. Pat. No. 5,501,952, Issued Mar. 26, 1996. FISH does not require the extraction of DNA. In addition, procedures for separating fetal blood cells from maternal blood cells are well known in the art allowing the fetus and the mother to be analyzed from the same body fluid sample (see U.S. Pat. No: 5,629,147, Issued May 13, 1997).

Similarly, antibodies raised against specific mutations and/or variants in the gene products of the genes involved in folate, pyridoxine, or cobalamine metabolism can be used to identify specific polymorphisms. Alternatively, antibodies raised against the wild type proteins can be used to detect and/or quantify the amount of wild type protein present in a given biological sample. In the case in which cross-reacting protein isn't synthesized by the cells of an individual, or is synthesized in significantly lower amounts than those of control subjects, such determinations can be used to identify a genetic risk factor. In addition, these antibodies can be used in methods well known in the art relating to the localization and activity of the gene products, e.g., for Western blotting, imaging the proteins in situ, measuring levels thereof in appropriate physiological samples, etc. using any of the detection techniques known in the art. Furthermore, such antibodies can be used in flow cytometry studies, in immunohistochemical staining, and in immunoprecipitation which serves to aid the determination of the level of expression of a protein in the cell or tissue.

In the particular instance when the gene product is an enzyme, e.g., dihydrofolate reductase, the enzymatic activity of a biological sample can be indicative of the presence of a genetic risk factor. In a particular embodiment, a decrease in an enzyme activity that is associated with folate, pyridoxine, or cobalamine metabolism can be indicative of the presence of the genetic risk factor. Such assays can be performed on multiple samples such as on a microplate reader [Widemann et al., Clin Chem. 45:223–228 (1999)].

MODEL 1

The Gene-Teratogen Model for the Inheritance Pattern of Certain Developmental Disorders Introduction:

It has long been known, e.g. from extensive studies of exogenous teratogens in inbred mice [Finnell and Chernoff, Gene-teratagen interactions: an approach to understanding the metabolic basis of birth defects, In Pharmacokinetics in Teratogenesis,Vol. II:97–109 *Experimental Aspects In Vivo and In Vitro*, CRC Press, Inc, Boca Ratan, Fla. (1987)], that teratogens may be influenced by genetic factors. It is less well known that the same gene defect may cause different clinical disorders depending upon whether the metabolic effect of the gene defect is exerted during gestation in utero or during postnatal life. However, the consequences of gene-teratogen interactions in human pedigrees have not been extensively explored, especially the consequences for the use of linkage mapping to identify an unknown gene acting in utero to cause a developmental disorder. A number of common human developmental disorders have been shown to have a genetic component to their etiology. However, for certain developmental disorders, the mode of inheritance has been difficult to determine and linkage studies have met with unexpected difficulties or have achieved limited success. These developmental disorders include spina bifida cystica [Chatkupt, *Am J Med Genet*, 44:508–512 (1992)], Tourette's syndrome & related disorders, e.g. obsessive-compulsive disorder and chronic multiple tics syndrome [Pauls, *Adv Neurol*, 58:151–157 (1992); McMahon et al., *Adv Neurol*58:159–165 (1992); Heutink et al., *Am J Hum Genet*, 57:465–473 (1995); Grice et al., *Am J Hum Genet*, 59:644–652 (1996)], learning disorders, including dyslexia [Lewis, et al., *Behav Genet*, 23:291–297 (1993); Pennington, *J Child Neurol* 10 *Suppl*, 1:S69–S77 (1995)], conduct disorder [Lombroso et al., *J Am Acad Child Adolesc Psychiatry*, 33:921–938 (1994)], attention-deficit hyperactivity disorder [Lombroso et al., *J Am Acad Child Adolesc Psychiatry*, 33:921–938 (1994)], bipolar illness [Baron, *Acta Psychiatr Scand*, 92:81–86 (1995); Benjamin and Gershon, *Biol Psychiatry*, 40:313–316 (1996); Risch and Botstein, *Nature Genet*, 12:351–353 (1996); Jamison and McInnis, *Nature Med*, 2:521–522 (1996); Morell, *Science*, 272:31–32 (1996)], schizophrenia [Owen, *Psychol Med*, 22:289–293 (1992); Cloninger, *Am J Med Genet*, 54:83–92 (1994); Lander and Kruglyak, *Nature Genet*, 11:241–247 (1995); Baron, *Acta Psychiatr Scand*, 92:81–86 (1995); Benjamin and Gershon, *Biol Psychiatry*, 40:313–316 (1996); Baron, *Am J Med Genet*, 67:121–123 (1996)], autism [Lombroso et al., *J Am Acad Child Adolesc Psychiatry*, 33:921–938 (1994)], and obsessive-compulsive disorder in adults [Lombroso et al., *J Am Acad Child Adolesc Psychiatry*, 33:921–938 (1994)]. A recent article [Moldin, *Nature Genet.* 17:127–129 (1997)] has reviewed "The maddening hunt for madness genes."

The present model addresses the question of the mode of inheritance of certain developmental disorders and proposes the "gene-teratogen model." The model suggests that the mode of inheritance of genes acting prenatally may in some cases be fundamentally different from that of genes acting postnatally. Even the same gene acting prenatally may produce a different disorder from that gene acting postnatally. The inheritance pattern in the gene-teratogen model is simple, but from the perspective of the patient with the developmental disorder is neither dominant nor recessive. Some disorders regarded as multifactorial, polygenic, or oligogenic may have this mode of inheritance. In the gene-teratogen model, genetically determined teratogen production by the mother during pregnancy damages the fetus producing the abnormal phenotype of a developmental disorder. The model is illustrated with two types of loci, 1. a teratogenic locus acting in the mother, and 2. a modifying or specificity locus acting in the fetus. Damage by the teratogen is influenced also by environmental factors. The model is interesting because it is simple and because teratogenic loci will be difficult to locate by parametric or non-parametric linkage mapping techniques due to misspecification of the affection status of both mother and affected children. A study design is suggested for identifying teratogenic loci. An example of the gene-teratogen model is the major intrauterine effect seen in offspring of phenylketonuric mothers. Certain developmental disorders whose mode of inheritance has been difficult to determine or whose genetic factors have been difficult to locate are candidates for the gene-teratogen model, including spina bifida cystica, Tourette's syndrome, learning disorders including dyslexia, conduct disorder, attention-deficit hyperactivity disorder, bipolar illness, schizophrenia, autism, and obsessive-compulsive disorder.

The Gene Teratogen Model

The model is described in Table 1 using two kinds of loci: a "teratogenic" locus and a "modifying" or "specificity" locus. The gene-teratogen model requires a teratogenic locus. One or more modifying or specificity loci may or may not be present. Also, two types of phenotypes are defined: 1. the teratogen-induced phenotype; and 2. the teratogenic phenotype, i.e., the phenotype of a mother that produces a teratogenic effect during pregnancy. The two phenotypes are different for the teratogenic locus but are identical for the modifying or specificity loci.

TABLE 1

DIAGRAM OF THE GENE-TERATOGEN MODEL

| | Maternal Grandmother | Maternal Grandfather | Paternal Grandmother | Paternal Grandfather |
|---|---|---|---|---|
| Grandparents: | AabbCCdd | AaBbCcdd | AAbbCcDd | AAbbCCdd |
| Parents: | Mother aaBbCcdd | | Father AAbbCcDd | |
| Child: | Child (fetus) with developmental disorder AabbccDd | | | |
| locus A: | teratogenic locus, recessive, acting in the mother to cause intrauterine teratogenic damage to the fetus. | | | |
| locus B: | teratogenic locus, dominant, acting in the mother to cause intrauterine teratogenic damage to the fetus. | | | |
| locus C: | modifying or specificity locus, recessive, acting in the fetus. | | | |
| locus D: | modifying or specificity locus, dominant, acting in the fetus. | | | |

The teratogenic locus may be dominant (locus A) or recessive (locus B). This locus acts in the mother during pregnancy to cause an intrauterine teratogenic effect in the fetus. The teratogenic effect may result from the production of an endogenous teratogen, from potentiation of an exogenous teratogen, from a metabolic deprivation or imbalance or from some other mechanism. Only one teratogenic locus is required; both locus A and locus B are shown on the same diagram for simplicity. A specificity or modifying locus may be dominant (locus C) or recessive (locus D). Such a locus acts during pregnancy or after to modify the extent of the developmental damage done by the teratogenic locus or even to prevent or repair the damage. For example, for a teratogen acting at a certain time in development, locus C or D may determine whether brain or kidney is damaged, which structures of the brain are damaged, or whether damage occurs at all.

1. Locus A, recessive teratogenic locus, acting in the mother: The child is the patient with the abnormal phenotype of a specific developmental disorder, while mother, father, and grandparents do not have the abnormal phenotype of that disorder (Table 1). Locus A acts in the mother during pregnancy causing her to produce the teratogenic effect that damages the developing fetus leading to the developmental disorder either in the fetus or postnatally in the child or adult. Since this locus is recessive in action, the mother, a homozygote (aa) for the disease allele, is the genetic "patient." Her abnormal phenotype, the "teratogenic phenotype", is the trait of producing the teratogenic effect during pregnancy. Her fetus, damaged by the teratogenic effect in utero, does develop the teratogen-induced phenotype. However, the fetus is only a heterozygote (Aa) at locus A and thus lacks both the abnormal homozygous genotype at locus A and the abnormal teratogenic phenotype; e.g., if the fetus is a daughter, she will not produce the teratogenic effect later during pregnancy. Thus, the fetus is affected with the developmental disorder but is not the genetic "patient." Locus A, acting through a teratogenic effect, cannot be the only etiological factor for the developmental disorder. If it were, then all pregnancies of an aa mother would have the teratogen-induced phenotype which is not the case. Environmental and/or other genetic factors, are required. An aa father will have the abnormal genotype, but not the abnormal teratogenic phenotype because he could never become pregnant.

2. Locus B, dominant teratogenic locus acting in the mother: The situation is the same as for locus A except that locus B is dominant in action (Table 1). The mother has the abnormal genotype, Bb, and the abnormal teratogenic phenotype. The fetus has the teratogen-induced phenotype but in the instance shown (Table 1) has neither the abnormal genotype, the teratogenic phenotype, nor even a copy of the disease allele. The maternal grandfather shown (Table 1) has the abnormal genotype, Bb, but does not have the teratogenic phenotype because he could never become pregnant.

3. Environmental effects: The teratogenic effect is modified by environmental factors, e.g. maternal dietary factors, infection, or ingestion of teratogen. These environmental factors may interact with locus A or B or may act independently. From the perspective of the fetus later to develop the developmental disorder (teratogen-induced phenotype), intrauterine teratogenic is an environmental not a genetic effect.

4. Modifying or Specificity Loci Acting in the Fetus, Loci C & D: These loci may interact with the teratogenic locus or the environmental factors to increase or decrease their effect, or alternatively could act independently. Such genetic factors may be recessive (locus C) or dominant (locus D). Genotypes and phenotypes of locus C and D behave conventionally with respect to the developmental disorder. For locus C and D, the fetus is with the developmental disorder is now the genetic "patient". Maternal teratogenic in utero is an environmental effect. It is thus possible that the same gene locus could act in part as a teratogenic locus and in part as a modifying or specificity locus.

DISCUSSION

The Example of Phenylketonuria: An example of the gene-teratogen model is the major intrauterine effect in maternal phenylketonuria (PKU). Phenylketonuria itself is a recessive postnatal disorder. Untreated homozygous PKU mothers and fathers both have elevated blood phenylalanine (hyperphenylalaninemia). However, heterozygous offspring of untreated PKU mothers (but not fathers) have an abnormal phenotype. [Koch et al., *Acta Paediatr Suppl*, 407:111–119 (1994); Allen et al., *Acta Paediatr Suppl*, 407:83–85 (1994); Abadie et al., *Archives Pediatr*, 3:489–486 (1996)]. Thus the elevated blood phenylalanine or other metabolite(s) in the mother acts as a teratogen for the fetus. Note that the fetus of an untreated phenylketonuric mother does not have the phenotype of PKU (the "teratogenic phenotype"), but has a different phenotype (the "teratogen-induced phenotype"). Phenylketonurics [Menkes, *Textbook of Child Neurology*, Lea & Febiger, Philadelphia (1990)] are normal at birth and develop a progressive disorder postnatally characterized by vomiting, eczema, seizures (infantile spasms with hypsarrythmia on electroencephalography), and mental retardation. The fetus of an untreated phenylketonuric mother [Menkes, *Textbook of Child Neurology*, Lea & Febiger, Philadelphia (1990)] has a congenital non-progressive disorder of fetal origin characterized by microcephaly, abnormal facies, mental retardation, congenital heart disease, and prenatal and postnatal growth retardation. The PKU phenotype is a postnatal degenerative disorder; the phenotype of the PKU intrauterine effect is a developmental disorder. The teratogenic effect is not dependent upon the fetal genotype, although the fetus is an obligate heterozygote since the mother is a homozygote for phenylketonuria and the father (usually) has the normal genotype. Thus, in phenylketonuria, a mutation at the same gene locus causes two distinct disorders depending upon whether the period of abnormal gene action is prenatal or postnatal. A fetus with the abnormal homozygous genotype who is carried by a heterozygous mother is protected in utero, but develops PKU postnatally. A heterozygous fetus carried by a mother with the abnormal homozygous genotype is damaged in utero when the mother's genotype predominates, but is protected from PKU postnatally by its own genotype.

An Example from Studies in Inbred Mice: Finnell and Chemoff [Gene-teratagen interactions: an approach to understanding the metabolic basis of birth defects, In Pharmacokinetics in Teratogenesis, Vol. II: 97–109 *Experimental Aspects In Vivo and In Vitro*, CRC Press, Inc, Boca Ratan, Fla. (1987)] have reviewed a group of elegant experiments in inbred mice documenting that differences in susceptibility to exogenous teratogens can be regarded as a genetic trait that is determined by susceptibility or liability genes of either the maternal or fetal genotype [Finnell and Chemoff, Gene-teratagen interactions: an approach to understanding the metabolic basis of birth defects, In Pharmacokinetics in Teratogenesis,Vol. II:97–109 *Experimental Aspects In Vivo and In Vitro*, CRC Press, Inc, Boca Ratan, Fla. (1987)]; Finnell et al., *Am J. Med. Genet*. 70:303–311 (1997); Bennett et al.,*Epilepsia* 38:415–423 (1997)]. For example, sensitivity to acetazolamine-induced ectrodactyly is determined by the presence of three genes, and the fetus must be homozygous for the recessive allele at all three loci in order to express the malformation. However, the inbred mouse models used do not mirror the human situation in at least three respects. First, the human population is an outbred population compared to these inbred mouse models. Consequently, the relevant genotypes may be highly variable among members of different families. Second, the inbred mouse experiments address the question of exogenous rather than endogenous teratogens. Third, the inbred mouse studies rely upon known or candidate susceptibility loci, whereas in humans, the problem has been to locate and identify disease unknown loci largely by using linkage mapping techniques.

Implications for Linkage Mapping:

Teratogenic Locus (LocusA or B): The gene-teratogen model has major implications for linkage mapping done with either parametric or non-parametric methods. The problem for both methods is incorrect assignment of affection status. In the lod score method, a genetic model of the disease is constructed and an affection status is assigned to each member of the pedigree. If the genetic model specified is wrong, the linkage results may be falsely positive or falsely negative [Terwilliger and Ott, *Handbook of Human Genetic Linkage*, Johns Hopkins Univ. Pr., Baltimore (1994)].

In developmental disorders resulting from the gene-teratogen model, the phenotype assignment for lod score analysis will be incorrect. The patient with the developmental disorder will be assigned the affected phenotype, whereas the patient is actually affected only for the teratogen-induced phenotype, but is unaffected for the teratogenic phenotype. Likewise, the mother will be assigned the unaffected phenotype for linkage analysis. Actually, she is unaffected only for the teratogen-induced phenotype, but is affected for the teratogenic phenotype. Lod scores should increase when phenotype assignments have been corrected. However, apparently dominant inheritance may in fact turn out to be pseudodominant if the mutant allele is common in the population. For non-parametric analysis, a similar misassignment occurs. In the case of affected sib-pairs, the affected sibs will be assigned the affected phenotype. Actually, the sibs are affected only for the teratogen-induced phenotype, but are unaffected for the teratogenic phenotype. The mother will be assigned the unaffected or unknown phenotype. Actually, she is unaffected only for the teratogen-induced phenotype but is affected for the teratogenic phenotype. Thus, the "affected sib-pair" families are likely to turn out to contain only a single sporadic case, since the only individual in the kindred affected with the teratogenic phenotype will be the mother.

For the transmission/disequilibrium test (TDT) [Spielman et al., *Am J Hum Genet*, 52:506–516 (1993); Ewens and Spielman, *Am JHum Genet*, 57:455–464 (1995)] the patient with the developmental disorder will be assigned the affected phenotype. Actually, the patient will be affected only for the teratogen-induced phenotype but will be unaffected for the teratogenic phenotype. The mother will be assigned the unaffected or unknown phenotype. Actually, she is unaffected only for the teratogen-induced phenotype but is affected for the teratogenic phenotype. The expectation of TDT is that alleles of a linked locus will show distortion from random transmission from mother (or father) to the patient. Since the patient is unaffected for the teratogenic phenotype, no transmission distortion from mother (or father) to child will be observed. Transmission distortion for alleles of a teratogenic locus will in fact occur from the mother's parents to the mother, the actual patient for the teratogenic phenotype. But this will not be looked for because the phenotypes have been wrongly assigned. In addition, grandparents of the patients with the developmental disorder have probably not had DNA collected. Therefore, for the TDT, negative results may occur for disease alleles of a teratogenic locus because incorrect phenotype assignments will have been made. When correct phenotype assignments have been made, transmission distortion to the mother from her parents should be expected for disease alleles of a teratogenic locus. Analogous misassignments are made in allelic association and haplotype relative-risk analyses [Falk and Rubinstein, *Ann Hu, Genet*, 51:227–233 (1987); Terwilliger and Ott, *Hum Hered*, 42:337–346 (1992); Thomson, *Am J Hum Genet*, 57:487–498 (1995)].

Modifying or Specificity Loci (Locus C and/or D): Since these loci behave in a conventional fashion, the phenotype assignments will be correct. Consequently, genes identified by conventional parametric or non-parametric linkage studies are likely to be modifying or specificity loci. An important question for linkage mapping is the relative contribution to the abnormal phenotype of the developmental disorder made by the teratogenic locus versus that of a modifying or specificity locus. If the effect of a teratogenic locus is small, then loci identified by conventional linkage studies will be specificity or modifying loci and the mode of inheritance will be Mendelian or multifactorial. If a teratogenic locus makes a major contribution to phenotype, then linkage mapping studies will not give a consistent answer and the mode of inheritance will be difficult to determine.

The presence of a teratogenic locus may be suspected if the maternal contribution to phenotype is different from or greater than the paternal contribution. For example, the mother's relatives of spina bifida infants more frequently have affected children than the father's relatives. Suggested explanations for this observation have been mitochondrial inheritance, maternal effect, or genomic imprinting [Chatkupt, *Am J Med Genet*, 44:508–512 (1992)]. The operation of a teratogenic locus is another explanation and is itself a form of maternal effect. For a recessive teratogenic locus, the mother's sisters would be at greatest risk of having offspring with the teratogen-induced phenotype.

Implications for Definition of Phenotype: All the pregnancies of a mother with the teratogenic phenotype are at risk for the developmental disorder, the teratogen-induced phenotype. Yet only a few of the fetuses will be affected by the developmental disorder because of the action of environmental factors and/or the modifying or specificity loci. The action of the environmental factors is fully quantitative: depending upon the amplitude of the environmental effect, a mild, moderate, or severe teratogen-induced phenotype may result. In addition, the environmental factor may act at different times in fetal development producing qualitatively different phenotypes. Thus, quantitatively or qualitatively different teratogen-induced phenotypes may result from pregnancies of the same mother with the teratogenic phenotype. In addition, the action of the modifying or specificity loci may produce quantitatively or qualitatively different phenotypes in offspring of the same couple. Such different phenotypes may be diagnostically classified as different disorders. This may complicate attempts at associating specific loci with a specific teratogen-induced phenotype. All of the teratogen-induced phenotypes resulting from pregnancies of a mother with the teratogenic phenotype modified only by environmental factors are genetically indistinguishable. However, such teratogen-induced phenotypes affected also by the various modifying or specificity loci segregating among the offspring of a single couple are only partially genetically related.

Methods to Identify Teratogenic Loci: One effective approach to finding a putative teratogenic locus is to carry out non-parametric linkage studies of families consisting of a patient affected with the developmental disorder, the patient's two (unaffected) parents, and the patient's four (unaffected) grandparents (Table 1). In such a family, the mother is the genetic patient but the other family members are not. Now, the mother's nuclear family (the mother and her parents) is compared with the father's nuclear family (the father and his parents). In a haplotype relative risk study, the disease allele(s) of the teratogenic locus will occur more frequently in the mother compared with other alleles of her parents; the disease allele(s) of the teratogenic locus will not occur more frequently in the father compared with other alleles of his parents. In a transmission/disequilibrium test, transmission distortion will be seen for the disease allele(s) of a teratogenic locus in the mother's nuclear family but not in the father's nuclear family. In an allelic association study, the disease allele will occur more frequently in mothers, patients (with the developmental disorder), and patient's sibs (both affected and unaffected) than in unrelated control individuals. Disease allele frequency in fathers will not be distinguishable from that in control individuals.

Certain developmental disorders with a genetic component to etiology, whose mode of inheritance has been difficult to determine or whose genetic factors have been difficult to locate, including those mentioned earlier, are candidates for the gene-teratogen model.

MODEL 2

The DNA Polymorphism-Diet-Cofactor-Development Hypothesis for Schizophrenia and Other Developmental Disorders Folate metabolism is complex. At least 30 gene loci are involved in absorption, transport, and metabolism of folate, and these are regulated by additional gene loci. Any of these is potentially a genetic risk factor for schizophrenia, although MTHFR and DHFR are particularly good candidates. Likewise, genes encoding proteins involved in the pathways of other vitamin-cofactors may be genetic risk factors.

Two cofactors that may be of particular potential importance are cobalamin and pyridoxine. Cobalamin is relevant because its metabolism is closely intertwined with that of folate. For example, cobalamin is required for the activity of methionine synthase (MTR), a folate-related enzyme. Decreased cobalamin can affect folate metabolism through the folate trap. Pyridoxine is relevant because the pyridoxine-dependent enzyme cystathionine beta-synthase (CBS), along with the cobalamin-dependent enzyme MTR and folate pathways including MTHFR and DHFR all participate in catabolism of homocysteine, an amino acid that is suspected of being a teratogen during pregnancy. Also, kynureninase, an important enzyme affecting niacin metabolism and serotonin synthesis is pyridoxine-dependent. Therefore, mutations of the genes encoding such proteins, especially common polymorphisms, could play a role in the cause of schizophrenia.

Since folate, cobalamin, and pyridoxine are all dietary constituents, the dietary content of these cofactors could be lead to an "environmental" generation of a risk factor for schizophrenia. In addition genes encoding proteins involved in folate, cobalamin, and pyridoxine metabolism and catabolism could be genetic risk factors for schizophrenia. Thus, the cofactors and the proteins involved in pathways relevant to these cofactors can potentially have either or both environmental and genetic effects on the susceptibility of an individual on schizophrenia.

Since the genetic aspect of schizophrenia differs so profoundly from other disorders which have been identified by linkage mapping techniques, it is clear that a new model for the genetic connection to schizophrenia is required. Therefore, the DNA Polymorphism-Diet-Cofactor-Development (DDCD) hypothesis, is disclosed herein.

The DDCD hypothesis is that interacting genetic and environmental factors affecting the metabolism of folate, cobalamin, or pyridoxine or all of these, play a role in the etiology of schizophrenia. The genetic effect results from the aggregate effect of multiple mutations that individually, for the most part, have small effects on folate-, cobalamin- or pyridoxine-related genes, some of which will be common in the population, and can act in utero. Environmental factors include dietary folate and cobalamin and pyridoxine. If schizophrenia results from mild deficiency during fetal development of dietary folate, cobalamin, or pyridoxine potentiated by mild genetic susceptibility mutations of genes related to these cofactors and by pregnancy, then this would be difficult to document by linkage mapping techniques. An example of interaction of genetic and environmental factors is that genetic factors are important for incorporating dietary folate; the enzyme dihydrofolate reductase is required for conversion of dietary folate to folinic acid thus allowing dietary folate to enter the body's metabolic pathways. Another example is that folate and cobalamin requirements increase during pregnancy; thus pregnancy could potentiate the effects of mild genetic defects of mother, fetus, or both. Deficiencies of a vitamin are often part of a broader dietary deficiency affecting multiple nutrients in addition to the vitamin being measured.

Locus Heterogeneity: The metabolic pathways of folate, cobalamin, and pyridoxine are complex and related to each other. Multiple gene loci code for the enzymes and transport proteins are required (Tables 2–7). Thus, a defect of folate, cobalamin, or pyridoxine metabolism could result from the aggregate effect of multiple mutations each of relatively small effect interacting with environmental factors. Different individuals might have different combinations of mutations. Such a metabolic defect would be difficult to detect by linkage mapping techniques because of locus heterogeneity.

Alternatively, even if one genetic defect were sufficient to make an individual more susceptible to having schizophrenic offspring, for example, because of the large number of potential genetic factors, and the corresponding importance of environmental factors, elucidation of such an individual genetic defect would still be difficult unless, of course, the genetic defect caused a major effect. The difficulty in elucidating an individual genetic defect is magnified when the genetic factor acts in the mother, and not in the schizophrenic patient.

High Disease Allele Frequency: Numerous mutational variants of folate and cobalamin genes are known. Some of these have functional significance and in addition are sufficiently common in a given population to be regarded as genetic polymorphisms. However, these common alleles are unlikely to have a major harmful effect by themselves, for if they did they would become uncommon in the population in the absence of selection effects, and would likely appear as Mendelian disorders. Thus, the folate, cobalamin, or pyridoxine disease alleles related to schizophrenia would appear to be more likely those of minor deleterious effect or those with harmful effect only in the presence of environmental deficiencies or pregnancy. Such disease genes of high population frequency will be difficult to detect by linkage mapping methods because high disease allele frequency decreases the power of linkage studies [Terwilliger and Ott, *Handbook of Human Genetic Linkage*, John Hopkins Univ. Press, Baltimore, (1994)].

Developmental Genes: Folate, cobalamin, and pyridoxine defects act prenatally as well as postnatally. Folate, cobalamin, and pyridoxine metabolism are crucial for DNA synthesis and cell division, which are of disproportionate importance during brain development. Some defects of folate, cobalamin, or pyridoxine metabolism elevate blood homocysteine, a toxic and potentially teratogenic substance. Genes acting in the mother to damage the developing fetus, e.g. via the gene-teratogen model (Model 1, above), have a mode of inheritance that is neither dominant nor recessive with respect to the fetus. Attempts to assign a mode of inheritance in this situation will be unsatisfactory because affection status would be incorrectly assigned. The mode of inheritance of a developmental disorder resulting from a teratogenic locus would be regarded as either multifactorial or unknown. This is the situation with schizophrenia whose mode of inheritance is unknown. Use of an incorrect genetic model decreases the power of a linkage studies [Terwilliger and Ott, *Handbook of Human Genetic Linkage*, John Hopkins Univ. Press, Baltimore, (1994)].

Genes of Folate Metabolism: Folate metabolism is extremely complex [Rosenblatt, In: *The Metabolic and Molecular Bases of Inherited Disease*, Scriver et al. (eds), New York: McGraw-Hill, pp. 3111–3128 (1995); Mudd et al., In: *The Metabolic and Molecular Bases of Inherited Disease*, Scriver et al. (eds), New York: McGraw-Hill pp. 1279–1327 (1995)]. At least 30 gene loci (Table 2) have been identified as folate-related. These contribute to folate mediated 1-carbon transfer reactions, binding, transport and metabolism of folate, and other functions. A number of these have been cloned and localized to a chromosomal region (Table 3).

TABLE 2

FOLATE-RELATED GENES/ENZYMES/TRANSPORTERS[a]

| Folate-Related Genes/Enzymes/Tranporters[a] | SEQ ID NO: |
|---|---|
| methylenetetrahydrofolate reductase, MTHFR, MIM 236250 | 1 |
| methionine synthase (methyltetrahydrofolate:L-homocysteine S-methyltransferase), MTR, MIM 156570 | 2 |
| dihydrofolate reductase, DHFR, MIM 126060 | 3 |
| folylpolyglutamate synthase, FPGS, MIM 136510 | 4 |

TABLE 2-continued

FOLATE-RELATED GENES/ENZYMES/TRANSPORTERS[a]

| Folate-Related Genes/Enzymes/Tranporters[a] | SEQ ID NO: |
|---|---|
| folate receptor 1, folate receptor alpha (FOLR1, adult; FR-alpha), MJM 136430 | 5 |
| folate receptor 2, folate receptor beta (FOLR2, fetal; FR-beta), MIM 136425 (a.a.) | 6 |
| folate receptor 2-like (FOLR2L, fetal-like), MIM-none | |
| folate receptor gamma (FR-gamma), MIM 602469 | 7 |
| serine hydroxymethyltransferase 1, SHMT1, MIM 182144 | 8 |
| methylenetetrahydrofolate dehydrogenase, methenyltetra-hydrofolate cyclohydrolase, 10-formyltetrahydrofolate synthetase (trifunctional enzyme, MTHFD), MIM 172460 | 9 |
| serine hydroxymethyltransferase 2, SHMT2, MIM 138450 | 10 |
| thymidylate synthase, TYMS, MIM 188350 | 11 |
| GAR (5-phosphoribosylglycineamide) transformylase, GART, MIM 138440 | 12 |
| reduced folate carrier-1, RFC1. Probably identical to micromolar membrane transport protein, intestinal folate carrier-1 (IFC1), and neutral folate transport protein. MIM 600424 | 13 |
| cystathionine beta-synthase, CBS, MIM 236200 | 14 |
| AICAR (5-phosphoribosyl-5-aminoimidazole-4-carboxamide) transformylase | 15 |
| glutamate formiminotransferase, MIM 229100 | |
| forminotetrahydrofolate cyclodeaminase | |
| 5,10-methenyltetrahydrofolate synthetase | 16 |
| 10-formyltetrahydrofolate dehydrogenase, Mim 600249 | |
| glycine cleavage pathway (SHMT plus three enzymes): | |
| MIM 238331 | |
| Gly-decarboxylase MIM 238300 | 17 |
| H-Protein MIM 238330 | 18 |
| T-Protein MIM 238310 | 19 |
| cblG (affects function of MTR), MIM 250940 | |
| methionine adenosyltransferase 1, MAT1A, (ATP:L-methionine S-adenosyltransferase), MIM 250850 | 20 |
| pteroyl polyglutamate liydrolase (“conjugase”), form 1 | |
| pteroyl polyglutamate liydrolase (“conjugase”), form 2 | |
| NAD-dependent enzyme methylene tetrahydrofolate dehydrogenase cyclohydrolase (a.a.) | 21 |
| methionine adenosyltransferase 2, MAT2A, MIM 601468 | 22 |
| 5-methyltetrahydrofolate-homocysteine methyltransferase reductase (MTRR) MIM 602568; #Variant in MTRR linked to cblE MIM 236270 | 23 |
| methyltranferases | |
| S-adenosylmethionine decarboxylase, MIM 180980 | 24 |
| decarboxylated S-adenosylmethionine:putrescine propylaminotransferase or spermidine synthetase (a.a.) | 25 |
| S-adenosylhomocysteine hydrolase, , MIM 180960 | 26 |
| betaine-homocysteine methyltransferase dimethylthetin-homocysteine methyltransferase | 27 |
| gamma-cystathionase (L-cystationine cysteine-lyase (deaminating)), MIM 602888 | 28 |
| folic acid transport protein, MIM 229050 | |
| DHFR (exon 6 and 3' flanking region) | 30 |
| kynureninase | 35 |
| human DHFR, exons 1 and 2 [Chen et al., J. Biol. Chem. 259: 3933–3943 (1984)] | 36 |

[a]listed with alternate names, abbreviations, and MIM numbers; #cblE is a phenotype for a particular group of disorders of folate/cobalamin metabolism. (a.a.) indicates the amino acid sequence

TABLE 3

LOCALIZED GENE LOCI RELATED TO FOLATE METABOLISM

| Gene/enzyme/ transport protein | Location | References |
|---|---|---|
| MTHFR | 1p36.3 | Goyette et al.,(1994); *, ** |
| MTR | 1q43 | Cook and Hamerton, (1979); Mellman et al., (1979) ** |
| DHFR | 5q11.2–13.2 | Weiffenbach et al., (1991) Gilliam et al. (1989b) *, ** |
| FPGS | 9cen-q34 | Jones and Kao (1984): Walter et al. (1992) *, ** |
| MAT | 10q22 | ** |
| FR | 11q13.3–q14.1 | Lacey et al. (1989), Ragoussis et al, (1992); Ratnum el al. (1989); Walter et al. (1992);* |
| | 11q13.3–113.5 | Ragoussis et al, (1992),** |
| SHMT2 | 12q12–q14 | Garrow et al., (1993); Law and Kao, (1979)* |
| | 12q13 | ** |
| MTHFD | 14q24 | Rozen et al., (1989), Jones et al. (1981),*, ** |
| LCCL | 16pter-qter | *, ** |
| SHMT1 | 17p11.2 | Garrow et al., (1993)*, ** |
| TYMS | 18p11.31.–p11.22 | * |
| | 18p11.32 | Hori et al., (1990); Silverman et al., (1993) |
| SAHH | 20cen-q13.1 | * |
| GART | 21q22.1 | McInnis et al. (1993) Schild et al. (1990) Avrarmopoulos et al. (1993) Goto et al. (1993) *, ** |
| RFC1 | 21q22.2–22.3 | Moscow et al., (1995) |
| CBS | 21q22.3 | Munke et al.,(1988) |

notes: MTHFR = methylenetetrahydrofolate reductase. MTS = methionine synthase. DHFR = dihydrofolate reductase. FPGS = folylpolyglutamate synthase. MAT = methionine adenosyltransferase, (ATP: L-methionine S-adenosyltransferase). FR = folate receptor complex: FR-alpha = FOLR1 = folate receptor 1, adult; FR-beta = FOLR2 = folate receptor 2, fetal; FR-gamma; FOLR2L = folate receptor 2-like. SHMT2 = serine hydroxymethyltransferase 2, mitochondrial. MTHFD = 5, 10-methylenetetrahydrofolate dehydrogenase, 5, 10-methylenetetrahydrofolate cyclohydrolase, 10-formytetrahydrofolate synthase (trifunctional enzyme). LCCL = gamma-cystathionase (L-cystathionine cysteine-lyase (deaminating). SHMT1 = serine hydroxymethyltransferase 1, soluble. TYMS = thymidylate synthetase. SAHH, S-adenosylhomocysteine hydrolase. GART = phosphoribosylglycineamide formyltransferase. RFC1 = reduced folate carrier-1 possibly identical to IFC1, intestinal folate carrier-1). CBS = cystathionine beta-synthase. Location information from GOD (*), from MIM (**).

Goyette et al., Nat. Gen. 7:195–200 (1994)
Cook and Hamerton, Cytogenet Cell Genet. 25:9–20 (1979)
Mellman el al., Proc. Natl. Acad. Sci. 76:405–409 (1979)
Weiffenbach et al., Genomics 10:173–185 (1991)
Gilliam et al. Genomics 5:940–944 (1989b)
Jones and Kao Cytogenet Cell Genet. 37:499 (1984)
Walter et al. Ann. Hum. Genet. 56:212 (1992)
Lacey et al. Am.J. Med. Genet. 60:172–173 (1989)
Ragoussis et al, Genomics 14:423–430 (1992)
Ratnum et al. Biochem. 28:8249–8254 (1989)
Garrow et al. J. Biol. Chem. 268:11910–11916 (1993).
Law and Kao, Cytogenet Cell Genet, 24:102–114 (1979)
Rozen et al., Ann. Hum. Genet, 44:781–786 (1989)
Jones et al. Somat. Cell Genet. 7:399–409 (1981)
Hori et al., Hum. Genet 85:576–580 (1990)
Silverman et al., Genomics 15:442–445 (1993)
McInnis et al. Genomics 16:562–571 (1993)
Schild et al. Proc. Natl. Acad. Sci 87:2916–2920 (1990)
Avrarmopoulos et al. Genomics 15:98–102 (1993)
Goto et al. Neuromusc Disord. 3:157–160 (1993)
Moscow et al., Cancer Res. 55:3790–3794 (1995)
Munke et al. Am J. Hum. Gen. 42:550–559 (1988)

Genes of Cobalamin Metabolism: Cobalamin metabolism is also complex [Benton and Rosenberg, In:

The Metabolic and Molecular Bases of Inherited Disease, Disease, Scriver et al. (eds), New York: McGraw-Hill, 3129–3149 (1995)]. At least 15 gene loci (Table 4) have been identified as cobalamin-related. These contribute to the binding, transport, and metabolism of cobalamin, and its functions. A number of these have been cloned and localized to a chromosomal region (5). Cobalamin metabolism is closely intertwined with that of folate. For example, cobalamin is required for the activity of MTR, a folate-related enzyme. Decreased cobalamin can affect folate metabolism through the folate trap [Rosenblatt, In: *The Metabolic and Molecular Bases of Inherited Disease*, Scriver et al. (eds), New York: McGraw-Hill, pp. 3111–3128 (1995); Quadros et al., *Biochem. Biophys. Res. Commun.*, 222:149–154 (1996)].

TABLE 4

COBALAMIN-RELATED GENES/ENZYMES/TRANSPORTERS[a]

| Cobalamin-Related Genes/Enzymes/Tranporters[a] | SEQ ID NO: |
|---|---|
| (gastric) intrinsic factor, GIF, MIM-261000 (combined deficiency of GIF & R-binder, MIM 243320 | 31 |
| intrinsic factor receptor, IFCR, MIM-261100 | |
| transcobalamin I, TCI (an R-protein, plasma), MIM 189905 | 32 |
| transcobalamin III, TCIII (an R-protein, plasma), MIM-none | |
| other R-proteins (R-binders, cobalophylins, haptocorrins), MIM 193090 | |
| transcobalamin II, TCII MIM 275350 | 33 |
| transcobalamin II receptor, TCII receptor, MIM-none | |
| methylmalonyl Co-A mutase, MCM (MUT locus), MIM 251000 | 34 |
| cblF, lysosomal cbl efflux, MIM 277380 | |
| cblC, cytosolic cbl metabolism, MIM 277400 | |
| cblD, cytosolic cbl metabolism, MIM 277410 | |
| cblA, mitochondrial cbl reduction, (AdoCbl synthesis only), MIM 251100 | |
| cblB, cob(I)alamin adenosyltransferase, (AdoCbl synthesis only), MIM 251110 | |
| cblE, methyltransferase-associated cbl utilization, MIM 236270 | |
| cblG, methyltransferase-associated cbl utilization, MIM 250940 | |

[a]listed with alternate names, abbreviations, and MIM numbers

TABLE 5

LOCALIZBD GENE LOCI RELATED TO COBALAMIN METABOLISM

| Gene/enzyme/transport protein | Location | References |
|---|---|---|
| MCM (MUT locus) | 6p21.2–p21.1 | Qureshi et al. (1994)* |
| IF/GIF | 11q12–q13 | Hewit et al. (1991)* |
| TCI (an R-protein, plasma) | 11q11–q12.3 | Johnston et al., (1992) Sigal et al., (1987),* |
| TCII | 22q11.2–q13 22q12/13border | Li et al., (1995) |

notes: MCM = methymalonyl Co-A mutase; IF/GIF = (gastric) intrinsic factor; TCI = transcobalmin I; TCII = transcobalamin II. Location information from GDB (*), from MIM (**).

Qureshi et al., Crit. Rev. Oncol. Hematol. 17: 133–151 (1994)

Hewit et al., Genomics 10: 432–440 (1991)

Johnston et al., Genomics 12: 459–464 (1992)

Sigal et al.,N. Engl. J. Med. 317: 1330–1332 (1987)

Li et al., Biochem. Biophys. Res. Comm. 208: 756–764 (1995)

Genes of Pynidoxine Metabolism: Pyridoxine metabolism is also complex with three dietary forms convertible to pyridoxal phosphate [Whyte et al., Hypophosphatasia, In: The Metabolic and Molecular Bases of Inherited Disease, Scriver et al. (eds), New York: McGraw-Hill pp. 4095–4111 (1995)] and many pyridoxine-related and pyridoxine-dependent enzymes including decarboxylases and all aminotranferases (Table 6). A number of pyridoxine-related enzymes have been cloned and localized to a chromosomal region (Table 7). Pyridoxine metabolism is related to folate metabolism, especially 1-carbon transfer reactions: both serine hydroxymethyltransferases and the P-protein (glycine decarboxylase) of the glycine breakdown system are pyridoxine-dependent.

TABLE 6

SOME PYRIDOXINE-RELATED GENES/ENZYMES/[a]

| | |
|---|---|
| 1. cystathionine beta-synthase, CBS, | MIM 236200 |
| 2. gamma-cystathionase, (L-cystathionine cysteine-lyase, deaminating), LCCL | MIM 219500 |
| 3. glycine cleavage system (GCS): glycine decarboxylase (P-protein) | |
| 4. serine hydroxymethyltransferase 1, SHMT1, | MIM 182144 |
| 5. serine hydroxymethyltransferase 2, SHMT2, | MIM 138450 |
| 6. kynureninase | MIM 278600 |
| 7. all aminotransferases, (e.g. ornithine-gamma-aminotranferases, OAT,) | MIM 258870 |
| 8. decarboxylases, e.g. glutamic acid decarboxylases, GAD1, GAD2, | MIM 266100 |
| 9. pyridoxamine(pyridoxine)-5'-phosphate oxidase | MIM 603287 |

[a]listed with alternate names, abbreviations, and MIM numbers.

TABLE 7

SOME LOCALIZED GENE LOCI RELATED TO PYRIDOXINE METABOLISM

| Gene/enzyme | Location | References |
|---|---|---|
| 1. GAD2 | 2q31, | Bu et al., 1992) |
| 2. GCS P-protein | 9p13 | Hamosh et al. 1995) |
| 3. GAD1 | 10p11.23 | Bu et al. 1992) |
| 4. OAT | 1Oq26 | ** |
| 5. SHMT2 | 12q12-14 | Garrow et al., 1993; Law and Kao, 1979 |
| 6. LCCL | l6pter-qter | *, ** |
| 7. SHMT1 | 17p11.2 | Garrow et al. 1993 * ** |
| 8. CBS | 21q22.3 | Munke et al. 1988 |
| 9. PNPO (PPO) | | Ngo et al. 1998 |

[a]listed with alternate names, abbreviations, and MIM numbers.

Location information from GDB (*), from MIM (**).

notes: GAD2 = glutamic acid decarboxylase 2, 67 kDa. GCS = glycine cleaving system, P-protein = glycine decarboxylase subunit. GAD1 = glutamic acid decarboxylase 1, 65 kDa. OAT = ornithine-gamma-aminotranferases. SHMT2 = serine hydroxymethyltransferase 2, mitochondrial. LCCL = gamma-cystathionase (L-cystathionine cysteine-lyase (deaminating). SHMT1 = serine hydroxymethyltransferase 1, soluble. CBS = cystathionine beta-synthase. PNPO = pyridoxamine(pyridoxine)-5'-phosphate oxidase References:

Bu et al., Proc. Nat. Acad. Sci., 89:2115 (1992).

Hamosh et al., In: "The Metabolic and Molecular Bases of Inherited Disease", Scriver et al. (eds), New York: McGraw-Hill pp. 1337–1348 (1995).

Garrow et al. J. Biol. Chem. 268:11910–11916 (1993).

Law and Kao, Cytogenet Cell Genet, 24: 102–114 (1979).

Munke et al. Am J. Hum. Gen. 42:550–559 (1988).

Ngo et al. Biochemistry 37:7741–7748 (1998).

Relevance of Folate, Cobalamine, And Pyridoxine to Schizophrenia: There is considerable evidence that schizophrenia results, at least in part, from damage to brain development in utero that becomes symptomatic in late adolescence or early adulthood. The etiology of schizophrenia has both genetic and environmental components. Because folate, cobalamin, and pyridoxine are all ingested and metabolized, they could potentially be both environmental and genetic factors for schizophrenia. Folate, cobalamin, and pyridoxine are relevant to schizophrenia in important ways. First, all of them are required for cell division because of their role in nucleic acid synthesis [Rosenblatt, In: *The Metabolic and Molecular Bases of*

*Inherited Disease*, Scriver et al. (eds) New York: McGraw-Hill, pp. 3111–3128 (1995); Benton and Rosenberg, In: *The Metabolic and Molecular Bases of Inherited Disease*, Scriver et al. (eds)., New York: McGraw-Hill, 3129–3149 (1995)]. The developmental brain insult implicated in schizophrenia [Akbarian et al., *Arch. Gen. Psychiatry*, 50:169–177 (1993); Akbarian et al., *Arch. Gen. Psychiatry*, 50:178–187 (1993)] is an abnormality of neurogenesis and neuronal migration, which are midtrimester events requiring cell division. Thus folate, cobalamin, and pyridoxine deficiencies could result in the widespread decreased grey matter volume observed in schizophrenia.

Individuals that become schizophrenic later in life are more likely to be born during the winter and early spring [Boyd et al., *Schizophr. Bull.*, 12:173–186 (1986); Kendell and Adams, *Br. J. Psychiatry*, 158:758–763 (1991); O'Callaghan et al., *Br. J. Psychiatry*, 158:764–769 (1991)]; this corresponds to midtrimester in late fall & winter. Many folate- and pyridoxine-containing foods, e.g. dark green leafy vegetables, are less readily available in late fall & winter in northern climates. Seasonality was found to be a major determinant of micronutrient status including folate status in a population of pregnant and lactating women in The Gambia where folate deficiency was widespread [Bates et al. Eur. J. Clin. Nutr. 48:660–668 (1994)]. Dietary cobalamin comes from animal foods, e.g. meat, dairy products, and fish, and prolonged dietary insufficiency is required to produce cobalamin deficiency unless a person is a strict vegetarian or already has subclinical deficiency [Sanders and Reddy, *Am. J. Clin. Nutr.*, 59:1176S–1181S (1994)]. In fact, a significant fraction of the population already has subclinical deficiency for folate [Lewis et al., *Ann. NY Acad. Sci.*, 678:360–362 (1993)] and for [Carmel et al., *Arch. Intem. Med.*, 147:1995–1996 (1987); Pennypacker et al., *J. Am. Geriatr.* Soc., 40:1197–1204 (1992); Naurath et al., *Lancet.*, 346:85–89 (1995); Allen et al., *Am. J. Clin. Nutr.*, 62:1013–1019 (1995); Black et al., *J. Nutr.*, 124:1179–1188 (1994)]. Also, the dietary folate requirement increases during pregnancy [Scholl et al., *Am. J. clin. Nutr.*, 63:520–525 (1996); McPartlin et al., *Lancet.*, 341:148–149 (1993)] and most women become folate deficient during late pregnancy [Giles, *J. Clin. Pathol.*, 19:1–11 (1966)]. Cobalamin deficiency is also common during pregnancy [Gadowsky et al., *J. Adolesc. Health*, 16:465–474 (1995)] although subnormal levels of vitamin B12 during pregnancy must be interpreted with caution [Metz et al., *Am. J. Hemetol.*, 48:251–255 (1995)]. An increase in schizophrenia births has also been noticed after winter famine [Susser and Lin, *Arch. Gen. Psychiatry*, 49:983–988 (1992)]; Susser et al., *Arch. Gen. Psychiatry*, 53:25–31 (1996)], a time when severe dietary deficiency of both folate and cobalamin is more likely. A temporary increase in the incidence of neural tube defects was reported in Jamaica 11–18 months following Hurricane Gilbert and was found to be associated with decreased dietary folate [Duff and Cooper, *Am J. Pub.Health* 84:473–476 (1994)].

Schizophrenia is also associated with obstetrical complications, e.g. low birth weight and prematurity [Lewis and Murray, *J. Psychiatr. Res.*, 21:413–421 (1987)]. Low birthweight and prematurity have also been associated with dietary folate deficiency during pregnancy Scholl et al., *Am. J. clin. Nutr.*, 63:520–525 (1996). Hyperhomocysteinemia is a risk factor for unexplained recurrent early pregnancy loss [Wouters et al., *Fertil. Steril.*, 60:820–825 (1993)] and for abruptio placentae [Goddijn-Wesel et al., *Eur. J. Obstet. Gynecol. Reprod. Biol.*, 66:23–29 (1996)]. Hyperhomocysteinemia may be related to defects in folate-, cobalamin-, or pyridoxine-dependent reactions [Naurath et al., *Lancet.*, 346:85–89 (1995)]. Interestingly, stillbirths and schizophrenia share a similar seasonality of birth excess [Torrey et al., *Schizophr. Bull.*, 19:557–562 (1993)]. Also $N_2$ O, an anaesthetic gas that inhibits MTR, a cobalamin-requiring enzyme of folate metabolism, is a reproductive toxin for both men and women [Louis-Ferdinand, *Adverse Drug React. Toxicol Rev.*, 13:193–206 (1994)]. Methotrexate, an inhibitor of dihydrofolate reductase (DHFR), induces abortion.

Dietary folate deficiency and low plasma folate are common in inner city urban populations [Scholl et al., *Am. J. clin. Nutr.*, 63:520–525 (1996)]. Likewise, schizophrenia has been reported to be more common in inner city urban populations [Fuller and Bowler, *Schizophr. Bull.*, 16:591–604 (1990)]. Also, both low folate intake [Schorah and Wild, *Lancet.*, 341:1417 (1993)] and schizophrenia [Dohrenwned et al., *Science*, 255:946–952 (1992)] are correlated with lower socioeconomic status.

Immune function is impaired in folate deficiency [LeLeiko and Chao, In: *Rudolph's Pediatrics*, 20th ed., Stamford, Conn.: Appleton & Lange, pp. 1001–1010 (1996)], in cobalamin deficiency [Hitzig et al., *Ciba. Found. Symp.*, 68:77–91 (1978)] and in pyridoxine deficiency [Trakatellis et al. *Postgrad Med. J.* 73:617–622 (1997)] and deficient individuals are more susceptible to infection. Methotrexate, an inhibitor of dihydrofolate reductase, inhibits immune function [Hughes, In: *Rudolph's Pediatrics*, 20th ed., Stamford, Conn.: Appletone and Lange, pp. 517–519 (1997)]. And, as mentioned, dietary folate and cobalamin requirements increase during pregnancy [Scholl et al., *Am. J. clin. Nutr.*, 63:520–525 (1996); McPartlin et al., *Lancet.*, 341:148–149 (1993)]. This is relevant because the season-of-birth effect just mentioned in connection with dietary folate, or cobalamin deficiency has also been explained by in utero infectious illness, the "viral theory" of schizophrenia. Individuals born following winters with severe influenza epidemics are more likely to develop schizophrenia [Adams et al., *Br. J. Psychiatry*, 163:522–534 (1993)] though not all studies find this effect. Although it has not been demonstrated that either the schizophrenia fetus or the pregnant mother actually developed influenza, the histologic pattern in schizophrenia of a neuronal migration abnormality during brain development has been seen as compatible with a fetal viral infection [Kovelman and Scheibel, *Biol. Psychiatry*, 19:1601–1621 (1984); Bogerts et al., *Arch. Gen. Psychiatry*, 42:784–791 (1985); Akbarian et al., *Arch. Gen. Psychiatry*, 50:169–177 (1993); Akbarian et al., *Arch. Gen. Psychiatry*, 50:178–187 (1993)]. Thus folate or cobalamin, deficiency during pregnancy could result in greater susceptibility to viral infection affecting mother, fetus, or both. The infectious agent could be influenza itself. Alternatively, a severe influenza epidemic could be a "marker" of a severe winter, and infection by another agent could cause the brain damage. In this way, folate or cobalamin deficiency could cause the season-of-birth effect either through the mechanism of dietary deficiency alone, through maternal immune deficiency and infection, or both.

Methotrexate, a DHFR inhibitor, is also an important therapeutic agent for rheumatoid arthritis. Rheumatoid arthritis has repeatedly been found to have a decreased frequency in schizophrenics, a puzzling finding that remains unexplained [Eaton et al., *Schizophr. Res.*, 6:181–192 (1992)].

The developmental model of schizophrenia postulates that brain damage sustained in the second trimester of fetal life results in schizophrenia later in development [Brixey et al., *J. Clin. Psychol.*, 49:447–456 (1993)]. Both folate and cobalamin are already known to contribute to a first trimester fetal nervous system malformation, spina bifida cystica [Kirke et al., *Q. J. Med.*, 86:703–708 (1993); Gordon, *Brain Dev.*, 17:307–311 (1995)], and possibly other birth defects [Shaw et al., *Lancet.*, 346:393–396 (1995); Czeizel, *Lancet.*, 345:932 (1995)]. Some studies [Whitehead et al., *Q. J. Med.*, 88:763–766 (1995); van der Put et al., *Lancet.*, 346:1070–1071 (1995); Ou et al., *Am. J. Med. Genet.*, 63:610–614 (1996); Chatkupt et al., *Am. Acad. Neurol. Works in Progres*, WIP4: (1996)] suggest that a genetic susceptibility factor for spina bifida is a common allele of the folate gene, MTHFR, the nucleotide 677C->T transition converting an alanine residue to valine resulting in a heat-labile enzyme protein. Homozygotes for this allele, about 10% of the normal population, have lower erythrocyte folate and plasma folate during pregnancy [Molloy et al., *Lancet.*, 349:1591–1593 (1997)]. Homozygotes for this allele also develop moderately elevated blood homocysteine [van der Put et al., *Lancet.*, 346:1070–1071 (1995); Frosst et al., *Nature Genet.*, 10:111–113 (1995)] in the presence of dietary folate deficiency. Moderate hyperhomocysteinemia is toxic to adults [Fermo et al., *Ann. Intern. Med.*, 123:747–753 (1995)], and toxic to the fetus in early gestation [Wouters et al., *Fertil. Steril.*, 60:820–825 (1993)], and possibly teratogenic in the first trimester causing neural tube defects [Whitehead et al., *Q. J. Med.*, 88:763–766 (1995); van der Put et al., *Lancet.*, 346:1070–1071 (1995); Ou et al., *Am. J. Med. Genet.*, 63:610–614 (1996). Thus, the MTHFR heat-labile mutation, in the presence of decreased dietary folate in midtrimester, could be teratogenic both through hyperhomocysteinemia and also through folate deficiency causing the developmental brain damage hypothesized in the developmental model of schizophrenia [Brixey et al., *J. Clin. Psychol.*, 49:447–456 (1993)]. A second common polymorphism of MTHFR, the nt1298 A->C mutation could also be a genetic risk factor for spina bifida [van der Put et al., *Lancet.*, 346:1070–1071 (1995].

Schizophrenia is a common disorder, affecting 1% or more of the population [Karno et al., In: *Comprehensive Textbook of Psychiatry/VI*, 6th ed., Baltimore: Williams & Wilkins, pp. 902–910 (1995)]. Thus, if a significant proportion of schizophrenia shares a common etiology, both the genetic susceptibility factors and the environmental factors must be common in the population. As mentioned earlier, a significant fraction of the population is already subclinically deficient for folate and for cobalamin; also, pregnancy may increase this fraction since dietary folate and cobalamin requirements increase during that time. Several functional polymorphic alleles of folate and cobalamin genes are also common in the population including the MTHFR mutations just mentioned and polymorphisms of thymidylate synthase [Horie et al., *Cell Struct. Funct.*, 20:191–197 (1995)], transcobalamin II [Li et al., *Biochim. Biophys. Acta.*, 1219:515–520 (1994)], and folate-binding proteins [Li et al., 1994, supra; Shen et al., *Biochem.*, 33:1209–1215 (1994)]. Metabolic indicators of folate or cobalamin deficiency, e.g. hyperhomocysteinemia and hypermethylmalonicacidemia, are also common in the population [Naurath et al., *Lancet.*, 346:85–89 (1995)]. Thus there exists a statistical basis for the hypothesis that schizophrenia is a birth defect resulting from the action during gestation of genetic risk factors and environmental factors related to folate and/or cobalamin that lead to the generation of risk factors. Such factors are sufficiently common that at least in principle all cases of schizophrenia could result from this mechanism.

Finally, folate, cobalamin, and pyridoxine are relevant for schizophrenia because of findings in patients. Severe genetic deficiency of MTHFR may cause a "schizophrenia" phenotype [Freeman et al., *N. Engl. J. Med.*, 292:491–496 (1975); Regland et al., *J. Neural Transm. Gen. Sect.*, 98:143–152 (1994)]. Genetic deficiency of other folate and cobalamnin enzymes has been reported to cause nervous system disease, psychiatric disease, or schizophrenia-like illness [Mudd et al., In: *The Metabolic and Molecular Bases of Inherited Disease*, Scriver et al. (eds), New York: McGraw-Hill pp. 1279–1327 (1995); Hitzig et al., *Ciba. Found. Symp.*, 68:77–91 (1978); Cooper and Rosenblatt, *Annu. Rev. Nutr.*, 7:291–320 (1987); Shevall and Rosenblatt, *Can. J. Neurol. Sci.*, 19:472–486 (1992); Hall, *Br. J. Haematol.*, 80:117–120 (1992)]. Likewise, dietary deficiencies of folate or cobalamin may have similar effects [Cooper and Rosenblatt, *Annu. Rev. Nutr.*, 7:291*14 320* (1987); Shevall and Rosenblatt, *Can. J. Neurol. Sci.*, 19:472–486 (1992)]. Methylfolate therapy reportedly improved the clinical status of schizophrenics with borderline or definite folate deficiency [Godfrey et al., *Lancet.*, 2:392–395 (1990); Procter, *Br. J. Psychiatry*, 159:271–272 (1991)] although the improvement claimed was small and the finding controversial. Folate deficiency has been associated with disturbances in mood [Shulman, In: *Folic Acid in Neurology, Psychiatry, and Internal Medicine*, New York: Raven Pr., 463*14 474* (1979)], and it has been suggested that the most common neuropsychiatric system abnormality in severe folate deficiency is depression [Reynolds et al., *Lancet., ii:* 196–198 (1984)]. Methyltetrahydrofolate reportedly improved symptoms of depression in an open trial in elderly depressed patients [Guaraldi et al. *Ann. Clin.Psychiatry* 5:101–105 (1993)]. Schizophrenics are reported to have an 80% excess mortality from cardiovascular disease [Gottesman, *Schizophrenia Genesis*, Schizophrenia Genesis-The Origins of Madness, W. H. Freeman & Co. N.Y.(1991)]; hyperhomocysteinemia, dietary folate deficiency and the MTHFR 677C->T mutation have been implicated in cardiovascular disease in some studies [Morita et al., *Circulation*, 95:2032–2036 (1997)] but not others (Anderson et al., *J. Am. Coll. Cardiol.* 30:1206–1211 (1997)]. Also, kynureninase, an important enzyme of tryptophan metabolism, affecting niacin metabolism and serotonin synthesis, is pyridoxine-dependent. Niacin deficiency (pellagra) can cause mental changes including psychosis and hallucinations [Wilson, *Vitamin deficiency and excess*, pp.472–480. In: *Harrison's Principles of Internal Medicine*, (Scriber et al. e's.) McGraw-Hill, Inc., N.Y. (1994)]. Also, clozapine, resperidone, and olanzapine are thought to exert their antipsychotic effect in schizophrenia in part through serotonin receptor antagonism.

Gene Localization Studies in Schizophrenia and Folate/Cobalamine/Pyridoxine Genes: If folate, cobalamin, or pyridoxine genes are susceptibility factors for schizophrenia, it is possible that gene localization studies have already identified candidate chromosome regions that contain such a gene (Tables 3, 5, and 7). For three folate or cobalamin genes, DHFR, TCNII and TYMS, there is excellent concordance with schizophrenia gene localization studies.

On chromosome 5, DHFR has been located at 5q11.22–13.2. A schizophrenia translocation [t(1;5)(1q32.3;5q11.2–13.3)] was reported [McGillivray et al., *Am. J. Med. Genet.*, 35:10–13 (1990); Bassett, *Br. J. Psychiatry*, 161:323–334 (1992)] affecting 5q11.2–5q13.3. A proband and uncle, both with schizophrenia and eye-tracking abnormalities, had partial trisomy for 5q11.2–5q13.3; the third copy was inserted at lq32.3 giving a derivative chromosome, der(1)inv ins(1;5)(q32.2; q13.3q11.2). The proband's mother had a balanced translocation but was phenotypically normal without schizophrenia or eye-tracking abnormalities. She had the derivative chromosome 1 with extra material from chromosome 5 inserted but a corresponding deletion in one of her chromosomes 5. She thus had only two copies of 5q11.2–5q13.3. Further studies [Gilliam et al., *Genomics*, 5:940–944 (1989)] showed that the DHFR gene is located within this deleted region, 5q11.2–13.3. Another schizophrenia chromosome abnormality, inv5(p13;q13), has been reported [Bassett, *Br. J. Psychiatry*, 161:323–334 (1992)] affecting 5q13.

On chromosome 5, two-point lod scores of 4.64 and 2.29 were found [Sherrington et al., *Nature*, 336:164–167 (1988)] for the polymorphic markers D5S76 and D5S39 respectively in the region of the chromosome abnormality just discussed [McGillivray et al., *Am. J. Med. Genet*., 35:10–13 (1990); Bassett, *Br. J. Psychiatry*, 161:323–334 (1992)] affecting 5q11.2–13.3. Two other linkage studies found small positive lod scores in this region [Coon et al., *Biol. Psychiatry*, 34:277–289 (1993); Kendler and Diehl, *Schizophr. Bull*., 19:261–285 (1993)], but numerous other studies excluded this region under the assumptions and models used [Kendler and Diehl, *Schizophr. Bull*., 19:261–285 (1993)].

On chromosome 18, TYMS has been located at 18p11.32–p11.22. A ring chromosome with deletion of 18pter-p11, 18q23-qter [Bassett, *Br. J. Psychiatry*, 161:323–334 (1992)] was reported in a kindred with schizophrenia and bipolar illness [Bassett, *Br. J. Psychiatry*, 161:323–334 (1992)]. Deletion of a segment of 18p was reported in a schizophrenia chromosome [Bassett, *Br. J. Psychiatry*, 161:323–334 (1992)].

On chromosome 22, TCNII has been located at 22q11.2–q13, possibly at the 22q12/13 border. High lod scores have consistently been obtained in the region of TCNII: IL2RB, in 22q12–q13.1 gave a lod score [Pulver et al., *Am. J. Med. Genet*., 54:3–43 (1994)] of 2.82. Other markers over a broad region of 22q have given suggestive lod scores. D22S278, in 22q12, gave a lod score [Vallada et al., *Am. J. Med. Genet*., 60:139–146 (1995)] of 1.51. CRYB2, in 22q11.2–q12.1, gave a lod score [Lasseter et al., *Am. J. Med. Genet*., 60:172–173 (1995)] of 1.71. D22S10, in 22q11.1–q11.2, gave a lod score [Coon et al., *Biol. Psychiatry*, 34:277–289 (1993)] of 0.79. Highly significant p-values for non-parametric analyses have also been obtained: D22S278, in 22q12, for example gave p=0.001 [Gill et al., *Am. J. Med. Genet*., 67:40–45 (1996)].

The deletions of velocardiofacial (VCF) syndrome and related disorders (DiGeorge syndrome (DGS) and CATCH22) are located [Lindsay et al., *Genomics*, 32:104–112 (1996)] at 22q11.2. A psychotic disorder develops in about 10% of patients with VCF syndrome [Chow et al., *Am. J. Med. Genet*., 54:107–112 (1994)]. TCNII is not known to be located at or within these deletions. VCF and related disorders are relatively uncommon compared to schizophrenia; only 2 of 100 randomly selected patients (92 schizophrenics, 5 with schizoaffective disorder, and 3 with schizophreniform disorder) in the Maryland Epidemiological Sample were found [Lindsay et al., *Am. J. Hum. Genet*., 56:1502–1503 (1995)] to have VCF-related deletions (and later VCF syndrome) on 22q11.2. Consequently, it is not clear whether schizophrenia linkage studies are detecting a haplotype related to a VCS locus or some other locus in this region, such as TCNII.

For some other folate, cobalamin, or pyridoxine relevant genes, physical or genetic studies of schizophrenia have identified chromosomal regions near the gene.

DISCUSSION

The folate-cobalamin hypothesis for schizophrenia is attractive because it suggests that a single mechanism of genetic and environmental factors may play a major role in the etiology and pathogenesis of schizophrenia. The combined result of this mechanism is to damage fetal development, especially brain development by inhibiting nucleic acid synthesis, by affecting gene methylations, by increasing susceptibility to infection, and/or by producing teratogens.

This mechanism addresses several puzzling features of schizophrenia such as the season of birth effect, the association with famine and influenza epidemics, the negative association with rheumatoid arthritis, the associations with obstetrical abnormalities, social class, and urban environment. The mechanism also suggests approaches to diagnostic testing, to prevention, and to improved therapy.

It is not excluded that such a mechanism could also apply to a number of common human developmental disorders that have been shown to have a genetic component to their etiology but whose mode of inheritance has been difficult to determine and for which linkage studies have met with unexpected difficulties or have achieved limited success. These developmental disorders include Tourette's syndrome & related disorders (e.g. obsessive-compulsive disorder and chronic multiple tics syndrome) [Pauls, *Adv Neurol*, 58:151–157 (1992); McMahon et al., *Adv Neurol*, 58:159–165 (1992); Heutink et al., *Am J Hum Genet*, 57:465–473 (1995); Grice et al., *Am J Hum Genet*, 59:644–652 (1996)], learning disorders, including dyslexia [Lewis, et al., *Behav Genet*, 23:291–297 (1993); Pennington, *J Child Aeurol* 10 *Suppl*, 1:S69–S77 (1995)], conduct disorder [Lombroso et al., *J. Am. Acad. Child Adolesc. Psychiatry*, 33:921–938 (1994)], attention-deficit hyperactivity disorder [Lombroso et al., 1994, *J. Am. Acad. Child Adolesc. Psychiatry*, 33:921–938 (1994)], bipolar illness [Baron, *Acta. Psychiatr. Scand*., 92:81–86 (1995); Benjamin and Gershon, *Biol. Psychiatry*, 40:313–316 (1996); Risch and Botstein, *Nature Genet*., 12:351–353 (1996); Jamison and McInnis, *Nature Med*., 2:521–522 (1996); Morell, *Science*, 272:31–32 (1996)], autism [Lombroso et al., 1994, *J. Am. Acad. Child Adolesc. Psychiatry*, 33:921–938 (1994)], and obsessive-compulsive disorder in adults [Lombroso et al., 1994, *J. Am. Acad. Child Adolesc. Psychiatry*, 33:921–938 (1994)]. Some of these disorders have been shown to be associated with schizophrenia.

The present invention may be better understood by reference to the following non-limiting limiting Examples, which is provided as exemplary of the invention. The following Examples are presented in order to more fully illustrate one embodiment of the invention. It should in no way be construed, however, as limiting the broad scope of the invention.

EXAMPLE 1

DIAGNOSING SCHIZOPHRENIA

Structure of Datafiles

Data are arranged in a file suitable for input into a binary logistic regression program (Table 8). A model is created consisting of those explanatory variables actually available from the specific patient-to-be-diagnosed and family members participating in the testing. This new combined data set (reference data set+data from patient-to-be-diagnosed with participating family members) is analyzed by binary logistic regression for the model chosen giving the predicted probability that a proband is affected with schizophrenia for all of the probands including the patient-to-be-diagnosed.

The model can be modified if required. The goodness of fit for the patient-to-be-diagnosed is checked. The predicted probability that the patient-to-be-diagnosed has schizophrenia is compared with a classification table generated from the model used to determine likelihood of false positives and false negatives. The predicted probability that the patient-to-be-diagnosed is affected with schizophrenia, with likelihood of false positive or false negative result, is returned to the clinician.

TABLE 8

A HYPOTHETICAL PARTIAL REFERENCE DATA SET OF GENETIC EXPLANATORY VARIABLES TO ILLUSTRATE DATA STRUCTURE

| ID | resp | P111 | P112 | P211 | P212 | M111 | M112 | M311 | F511 | S2-411 | CA1-111 |
|---|---|---|---|---|---|---|---|---|---|---|---|
| 1 | 1 | 1 | 0 | 1 | 1 | 1 | 1 | 0 | 0 | 1 | 1 |
| 2 | 1 | 1 | 0 | 0 | 0 | 0 | 0 | 0 | 1 | 0 | 0 |
| 3 | 1 | 1 | 1 | 1 | 0 | 1 | 0 | 0 | 1 | 1 | 1 |
| 4 | 1 | 0 | 0 | 0 | 0 | 0 | 0 | 1 | 0 | 0 | 0 |
| 5 | 1 | 0 | 0 | 1 | 1 | 1 | 1 | 0 | 0 | 0 | 1 |
| 6 | 0 | 1 | 0 | 0 | 0 | 0 | 0 | 0 | 0 | 0 | 0 |
| 7 | 0 | 0 | 0 | 0 | 0 | 0 | 0 | 1 | 0 | 0 | 0 |
| 8 | 0 | 0 | 0 | 1 | 0 | 0 | 0 | 0 | 1 | 1 | 0 |
| 9 | 0 | 1 | 0 | 0 | 0 | 1 | 0 | 0 | 0 | 1 | 1 |
| 10 | 0 | 0 | 0 | 0 | 0 | 1 | 0 | 0 | 0 | 1 | 0 |
| 11 | . . . | | | | | | | | | | |
| n | | | | | | | | | | | |

For each proband (Table 8), the record contains several variables:
identificationnumber (ID) of the proband.
a binary response variable (resp) for affection status of the proband: response = 1, if the proband is affected with schizophrenia; response = 0 if proband is unaffected (i.e. a control individual). The proband is not necessarily one of the individuals for whom genotype data (explanatory variables) are available. The patient-to-be-diagnosed is assigned response = 0 when added to the reference data set.
a set of explanatory variables: i.e. sets of genotypes of mutations found in the schizophrenia patients and family members and controls and family members. The schizophrenia patients and the control individuals are probands (P) as is the patient-to-be-diagnosed. Unaffected family members are the proband's mother (M), father (F), sib(s) (S1, S2, etc.), child(ren) (C1, C2, etc.) or other relatives. Data for affected family members, e.g. the proband's mother (MA), father (FA), sibs (SA1,#
SA2, etc.), explanatory variables.

Genetic explanatory variables: Each individual has 0, 1, or 2 copies of any given mutation allele at a given locus. Thus a genotype at each locus contributes two independent explanatory variables. Most of the affected family members will be relatives of schizophrenia probands, but occasionally a relative of an unaffected proband will turn out to be affected with schizophrenia.

Mutations are tabulated as explanatory variables: (see Table 8):

(i) by the proband or relative in whom they occur, (e.g. P, M, F, S2, C1, MA, FA, SA1, CA1, other);
(ii) by the specific folate, cobalamin, or pyridoxine gene locus in which they occur (e.g. 1 =DHFR locus, 2=MTHFR locus, 3=TCN2 locus, 4=MTR locus, 5=CBS locus, etc.);
(iii) by the specific mutation within a locus (e.g., 1 =the first-designated mutation within a locus, 2=the second-designated mutation within a locus, etc.); and
(iv) by whether the individual has a single or double dose of the mutation. Thus an explanatory variable P321 records whether the proband has a single dose of the second-designated mutation of the third-designated locus, i.e. TCN2. A variable M312 records whether the proband's mother has a double dose of the first-designated TCN2 mutation studied.

In the present hypothetical reference dataset illustrated of genetic explanatory variables (Table 8), partial genotype data for probands, mothers, fathers, sibs and children are given for five gene loci. Not all of the possible explanatory variables are shown. Probands 1–5 are unrelated individuals with the definite clinical diagnosis of schizophrenia; probands 6–10 are unrelated unaffected (control) individuals. Probands 1, 2, 3, 6 and 9 all have a single copy of the first-designated DHFR mutation; proband 3 also has a second copy of that mutation. Probands 1, 3, 5 and 8 all have a single copy of the first-designated mutation at the MTHFR locus; probands 1 and 5 also have a second copy of that mutation. Mothers of probands 1, , 5, 9 and 10 all have a single copy of the first-designated DHFR mutation; mothers of probands 1 and 5 also have a second copy of this mutation. Mothers of probands 4 and 7 each have a single copy of the first-designated mutation of TCN2; data for a double dose are not shown. The fathers of probands 2, 3, and 8 each have a single copy of the first designated mutation of CBS; data for a double dose are not shown. The second (unaffected) sibs of probands 1, 3, 8, 9, and 10 each have a single copy of the first-designated mutation of MTR; data for a double dose are not shown. The first affected children of probands 1, 3, 5, and 9 each have a single copy of the first-designated mutation of DHFR. Other susceptibility loci and mutations can be incorporated in Table 8 in the same fashion e.g., cytokine gene mutations or polymorphisms, or major histocompatibility complex (MHC) mutations or polymorphisms.

Environmental explanatory variables: If only genetic explanatory variables (genotype data) are used, the maximum predicted probability that the proband is affected with schizophrenia is expected to be approximately about 0.5 in most populations. When environmental risk factors are included as explanatory variables, the maximum predicted probability that the proband is affected with schizophrenia may approach 1.0. Examples of environmental risk factors for a schizophrenia patient include:

(1) the proband's dietary folate/cobalamin/pyridoxine intake.
(2) the proband's circulating levels of folate/cobalamin/pyridoxine.

(3) the proband's circulating levels of homocysteine, methylmalonic acid, or cystathionine. Elevated levels are indicators of subtle folate/cobalamin deficiency.

(4) the proband's mother's dietary folate/cobalamin/pyridoxine intake at the time of patient diagnosis, during a pregnancy, or during the pregnancy that produced the proband.

(5) the proband's mother's circulating levels of homocysteine, methylmalonic acid, or cystathionine at the time of patient diagnosis, during a pregnancy, or during the pregnancy that produced the proband.

(6) dietary or circulating folate/cobalamin/pyridoxine or circulating levels of homocysteine, methylmalonic acid, or cystathionine for other family members.

(7) epidemiological factors related to the proband's gestation and birth, e.g. low birth weight or preterm birth, maternal infection, maternal smoking (associated with low plasma folate), season of birth (late winter or spring births are more common in schizophrenia), etc.

Method of Data Analysis

The method exemplified herein is based upon the published guide for the SAS system, but other software can be used. The dataset is analyzed using binary logistic regression to model the response probability, $p_i$, that the ith proband's affection status is 1, i.e. the probability that the ith proband has schizophrenia, given the vector of explanatory variables, $x_i$. That is:

$$p_i = \text{Prob}\ (y_i = 1 | x_i).$$

To do this the logit transformation of $p^i$ is modeled as a linear function of the explanatory variables in the vector, $x_i$:

$$\text{logit}\ (p_i) = \log\ (p_i/[1-p_i]) = \text{alpha} + \text{beta}' x_i$$

where: alpha is the intercept parameter and beta is the vector of slope parameters.

In SAS, the "descending" option is used to model the probability that the response=1, as in the present analysis, rather than response=0.

Outputs of binary logistic regression analysis

After analysis of a dataset, the outputs obtained from SAS include:

(a) Estimates and standard errors of the parameters (alpha and beta). Using estimates of the intercept parameter (alpha) and the slope parameter (beta) for each environmental or genetic risk factor, the logistic regression equation for the dataset can be written.

(b) Significance tests of the parameters (e.g. Wald chi-square). From the corresponding p-values, the level of significance of each of the environmental or genetic risk factors is determined. A global significance test of the data with corresponding p-value is also determined.

(c) Odds ratios are given for the slope parameters of each environmental or genetic risk factor. Thus the amount contributed by each environmental or genetic risk factor to the risk of schizophrenia is determined.

(d) The confidence limits for regression parameters and odds ratios are determined.

(e) The predicted probabilities of the observations can be computed, i.e. the probability that each individual in the dataset has schizophrenia:
alpha~=estimate of the intercept parameter;
beta~=vector of the estimates of the slope parameters;
x=vector of the explanatory variables;
p~=predicted probabilities $$p\sim = \frac{1}{1 + \exp(\text{alpha}\sim - \text{beta}\sim' x)}$$

(f) model is modified by adding or removing variables until a model is found that best fits the data;

(g) The model is tested for goodness-of-fit. Also, the degree of influence of each specific observation is tested to detect extreme or ill-fitting observations. These may be examples of data entry errors or alternatively, observations that do not fit the present model for schizophrenia.

(h) The probability that a new individual (the patient-to-be-diagnosed) is schizophrenic is then calculated from the final, modified, best fitting regression equation based upon parameters derived from a corrected/modified data set. A simple method of doing this is to add the data for the patient-to-be-diagnosed to the reference data set, a large group of well-studied schizophrenia probands, schizophrenia family members, control probands and control family members for whom data are available for many explanatory variables. A model is created consisting of those informative explanatory variables actually available from the specific patient-to-be-diagnosed and family members participating in the testing. This new combined data set (reference data set+data from patient-to-be-diagnosed with participating family members) is analyzed by binary logistic regression for the model chosen giving the predicted probability that a proband is affected with schizophrenia for all of the probands including the patient-to-be-diagnosed.

(i) A classification table is produced from the data set by the "jack knifing" procedure or an approximation to it. This procedure classifies each observation as an event or nonevent based on the model that omits the observation being classified. A classification table sorts observations into percent correct, percent false positives, and percent false negatives at various probability levels and computes sensitivity and specificity.

(i) The data set used for diagnostic testing is constantly being updated and the regression equation corrected. For example, stratification by geographic residence or geographic origin of ancestors must be considered for some environmental or genetic risk factor.

For example, in Table 9, entries 34–43 are shown for the data file containing genotypes of 38 schizophrenic probands plus 211 control probands; the first 38 are the affected probands. For individual 302088, the proband is affected ("1"); there is a single dose ("1") of the DHFR mutation but not a double dose ("0") and a single dose ("1") of the MTHFR mutation but not a double dose ("0"). The number 302088 identifies the individual whose genotypes are listed; the proband, in this case, is the same individual.

TABLE 9

SAS DATAFILE FOR SCHIZOPHRENIA PATIENTS AND CONTROLS

| | | | | | | |
|---|---|---|---|---|---|---|
| ... | | | | | | |
| ... | | | | | | |
| 34 | 302086 | 1 | 1 | 0 | 1 | 1 |
| 35 | 302088 | 1 | 1 | 0 | 1 | 0 |
| 36 | 302110 | 1 | 1 | 0 | 1 | 0 |

TABLE 9-continued

| SAS DATAFILE FOR SCHIZOPHRENIA PATIENTS AND CONTROLS | | | | | | |
|---|---|---|---|---|---|---|
| 37 | 302111 | 1 | 1 | 0 | 0 | 0 |
| 38 | 302136 | 1 | 1 | 1 | 1 | 0 |
| 39 | 100001 | 0 | 1 | 0 | 0 | 0 |
| 40 | 100061 | 0 | 0 | 0 | 0 | 0 |
| 41 | 100064 | 0 | 1 | 0 | 1 | 0 |
| 42 | 100067 | 0 | 0 | 0 | 1 | 0 |
| 43 | 100073 | 0 | 1 | 0 | 0 | 0 |
| ... | | | | | | |
| ... | | | | | | |
| ... | | | | | | |
| ... | | | | | | |

In Table 10, entries 31–40 are shown for thie data file containing genotypes of 35 mothers of schizophrenic probands plus (the same) 211 control probands. For individual 302083, the proband is affected ("1"); there is a single dose of the DHFR mutation ("1") but not a double dose ("0"); there is neither a single ("0") nor a double ("0") dose of the MTHFR mutation. The number 302083 identifies the individual whose genotypes are listed, a mother; the proband, in this case, is a different individual, her affected child.

TABLE 10

| SAS DATAFILE FOR SCHIZOPHRENIA MOTHERS AND CONTROLS | | | | | | |
|---|---|---|---|---|---|---|
| ... | | | | | | |
| ... | | | | | | |
| 31 | 302083 | 1 | 1 | 0 | 0 | 0 |
| 32 | 302103 | 1 | 0 | 0 | 1 | 0 |
| 33 | 302104 | 1 | 0 | 0 | 1 | 0 |
| 34 | 302105 | 1 | 1 | 0 | 1 | 0 |
| 35 | 302120 | 1 | 0 | 0 | 0 | 0 |
| 36 | 100001 | 0 | 1 | 0 | 0 | 0 |
| 37 | 100061 | 0 | 0 | 0 | 0 | 0 |
| 38 | 100064 | 0 | 1 | 0 | 1 | 0 |
| 39 | 100067 | 0 | 0 | 0 | 1 | 0 |
| 40 | 100073 | 0 | 1 | 0 | 0 | 0 |
| ... | | | | | | |
| ... | | | | | | |

In Table 11, entries 11–20 are shown for the data file containing genotypes of 15 fathers of schizophrenic probands plus (the same) 211 control probands. For individual 302084, the proband is affected ("1"); there is a single dose ("1") but not a double dose ("0") of the DHFR mutation; there is both a single ("1") and a double dose ("1") of the MTHFR mutation. The number 302084 identifies the individual whose genotypes are listed, a father; the proband, in this case, is a different individual, his affected child.

TABLE 11

| SAS DATAFILE FOR SCHIZOPHRENIA FATHERS AND CONTROLS | | | | | | |
|---|---|---|---|---|---|---|
| ... | | | | | | |
| ... | | | | | | |
| 11 | 302102 | 1 | 0 | 0 | 0 | 0 |
| 12 | 302106 | 1 | 1 | 0 | 0 | 0 |
| 13 | 302115 | 1 | 1 | 0 | 0 | 0 |
| 14 | 302117 | 1 | 1 | 0 | 0 | 0 |
| 15 | 302084 | 1 | 1 | 0 | 1 | 1 |
| 16 | 100001 | 0 | 1 | 0 | 0 | 0 |
| 17 | 100061 | 0 | 0 | 0 | 0 | 0 |
| 18 | 100064 | 0 | 1 | 0 | 1 | 0 |
| 19 | 100067 | 0 | 0 | 0 | 1 | 0 |
| 20 | 100073 | 0 | 1 | 0 | 0 | 0 |
| ... | | | | | | |
| ... | | | | | | |

In Table 12, entries 9–18 are shown for the data file containing genotypes of 13 unaffected sibs of schizophrenic probands plus (the same) 211 control probands. For individual 302089, the proband is affected ("1"); there is a single dose ("1") but not a double dose ("0") of the DHFR mutation; there is both a single ("1") and a double dose ("1") of the MTHFR mutation. The number 302089 identifies the individual whose genotypes are listed, an unaffected sib; the proband, in this case, is a different individual, the affected sib of individual 302089.

TABLE 12

| SAS DATAFILE FOR SCHIZOPHRENIA SIBS AND CONTROLS | | | | | | |
|---|---|---|---|---|---|---|
| ... | | | | | | |
| ... | | | | | | |
| 09 | 302071 | 1 | 1 | 0 | 0 | 0 |
| 10 | 302073 | 1 | 0 | 0 | 1 | 0 |
| 11 | 302089 | 1 | 1 | 0 | 1 | 1 |
| 12 | 302118 | 1 | 1 | 0 | 0 | 0 |
| 13 | 302126 | 1 | 1 | 0 | 0 | 0 |
| 14 | 100001 | 0 | 1 | 0 | 0 | 0 |
| 15 | 100061 | 0 | 0 | 0 | 0 | 0 |
| 16 | 100064 | 0 | 1 | 0 | 1 | 0 |
| 17 | 100067 | 0 | 0 | 0 | 1 | 0 |
| 18 | 100073 | 0 | 1 | 0 | 0 | 0 |
| ... | | | | | | |
| ... | | | | | | |

In Tables 9–12 for individual 100061, the proband is unaffected ("0"); there is neither a single dose ("0") nor a double dose ("0") of the DRFR mutation; thiere is neither a single dose ("0") nor a double dose ("0") of the MTHFR mutation. Since the proband is unaffected, this is a control individual. The number 100061 identifies the individual whose genotypes are listed, as a control individual; the proband, in this case, is the samne individual. The identical group of control individuals is used for all four comparisons.

EXAMPLE 2

Distribution of Folate Gene Polymorphism Genotypes Among Schizophrenics, Schizophrenia Parents, Schizophrenia Sibs, and Controls Summary The DNA polymorphism-Diet-Cofactor-Development hypothesis (DDCD hypothesis, described above) postulates that schizophrenia results in part from developmental brain damage sustained in utero from the aggregate effect of maternal defects of genes related to important cofactors, e.g. folate, cobalamin, pyridoxine, potentiated by a maternal dietary deficiency of these cofactors. The maternal damage to the fetus results in part from insufficiency of these cofactors themselves and in part from resulting effects such as immune deficiency and maternal teratogens, e.g. hyperhomocysteinemia. Genes from either parent acting in the fetus may modify these damaging effects as outlined in the gene-teratogen model (described above).

The hypothesis addresses all of the unusual biological and epidemiological features of schizophrenia: e.g. the decreased amount of grey matter in brain areas, the unusual birth-month effect, the geographical differences in incidence, the socioeconomic predilection, the association with obstetrical abnormalities (low birth weight and prematurity), the decreased incidence of rheumatoid arthritis, and the association with viral epidemics (described above).

The hypothesis can be supported by finding significant association of sequence variants of folate, cobalamin, or pyridoxine genes with schizophrenia. Folate, cobalamin, and pyridoxine absorption, transport, and metabolism are complex [Rosenblatt, In: *The Metabolic and Molecular Bases of Inherited Disease*, Scriver et al. (eds), New York: McGraw-Hill, pp. 3111-3128 (1995); Benton and Rosenberg, In: *The Metabolic and Molecular Bases of Inherited Disease*, Scriver et al. (eds), New York: McGraw-Hill, pp. 3129–3149 (1995); Whyte et al., *Hypophosphatasia*, In: The Metabolic and Molecular Bases of Inherited Disease, Scriver et al. (eds), New York: McGraw-Hill pp. 4095–4111] with multiple transport proteins, enzymes, and regulatory components. A strong candidate for harboring a mutation predisposing to schizophrenia is the DHFR gene coding for the folate enzyme dihydrofolate reductase. DHFR chemically reduces dietary folate converting it into a form that can enter cellular metabolism. DHFR is also important for DNA synthesis and is known to play a major role in development in utero. A novel polymorphic 19 basepair deletion of the DHFR gene has been isolated which could be of functional significance because it affects potential transcription factor binding sites.

A second candidate is the MTHFR gene, coding for methylenetetrahydrofolate reductase, MTHFR, an important enzyme of folate metabolism. MTHFR was of particular interest because severe deficiency of enzyme activity has been associated with the "schizophrenia" phenotype [Freeman et al., *N. Engl. J. Med*., 292:491–496 (1975); Regland et al., *J. Neural Transm. Gen. Sect*., 98:143–152 (1994)] and because a common mutation, the nt677 C->T transition results in a mutated gene that encodes a heat-labile MTHFR, having decreased enzymatic activity, which in the presence of dietary folate deficiency, causes the plasma homocysteine of homozygotes to become elevated [van der Put et al., *Lancet*., 346:1070–1071 (1995); Frosst et al., *Nature Genet*., 10:111–113 (1995)]. In adults, hyperhomocysteinemia is known to cause vascular disease and to be toxic [Frosst et al., *Nature Genet*., 10:111–113 (1995)]. Therefore, homocysteine that crosses the placenta could act as a fetal teratogen during pregnancy. Maternal folate deficiency could also have a more direct teratogenic effect through fetal folate deprivation. These effects could be potentiated by abnormalities of other folate, cobalamin, or pyridoxine genes, even if these abnormalities were only minor.

Materials & Methods:

1. Subjects and Sample Collection: Patients with schizophrenia and unaffected family members of schizophrenics, were ascertained from patient facilities, patient support groups, and family support group organizations. Nearly all schizophrenia families had only a single case of schizophrenia. The patients came from different schizophrenia families than the parents and sibs. The controls were unaffected and unrelated individuals not known to be schizophrenic or related to patients with schizophrenia or spina bifida. All subjects were of Caucasian background except two of the schizophrenia patients who were of African American background.

After informed consent was obtained, 20–40 ml of blood was collected into EDTA (purple-top) vacutainers, placed on ice immediately, and transported to the laboratory where plasma, packed red cells, and buffy coat were separated by centrifugation and frozen at −80° C.

2. Detection of Alleles: DNA was isolated using the QIAmp column DNA extraction procedure or the QIAGEN Genomic-tip method (QIAGEN, Chatsworth, Calif.). Alleles for a newly detected polymorphic 19 bp deletion in the dihydrofolate reductase (DHFR) gene were determined by polymerase chain reaction (PCR) amplification of the region surrounding the deletion using specific primers (FIG. 1) and direct detection of the PCR products after separation of products on a non-denaturing polyacrylamide gel. A Cetus—Perkin-Elmer 9600 thermocycler was used. Briefly, the PCR reaction contained 200 uM dNTPs, 1.5 mM $MgCl_2$, 10 pmols of each primer, in 10 $\mu$l reaction volume. The PCR conditions used were denaturation at 94° C. for 6 min. initially, followed by 35 cycles of 94° C. for 55 sec., 60° C. for 55 sec., and 72° C. for 55 sec. and a final extension at 72° C. for 12 min.

Alleles for the 677C->T transition of the methylenetetrahydrofolate reductase (MTHFR) gene were determined by cleavage with the restriction endonuclease, Hinfl, of PCR-amplified genomic DNA from blood and separation of the products by non-denaturing polyacrylamide gel electrophoresis [Frosst et al., *Nature Genet*., 10:111–113 (1995)].

3. Sequencing the Region Around the DHFR Deletion: Using the same primers (FIG. 1), genomic DNA from individuals with 1,1 and 2,2 genotypes was amplified by PCR and the products sequenced using an ABI PRISM 377 automated sequencer. Restriction sites were identified using the MAP Program in the GCG Package. Potential transcription factor binding sites were detected with the TESS program (transcription element search software, URL:http://agave. humgen.upenn. edu/tess/index. html).

4. Data Analysis: Since the mode of inheritance of schizophrenia is unknown, binary logistic regression was used to test the DHFR deletion allele and the MTHFR heat-labile allele as genetic risk factors for schizophrenia. Either the DHFR deletion polymorphism or the MTHFR heat-labile allele could itself be a genetic risk factor for schizophrenia. The genotypes of the two folate gene polymorphisms were used as explanatory variables. Genotypes of schizophrenia patients, parents, or sibs were compared with those of controls.

Four files were constructed consisting of schizophrenia patients+controls, mothers of schizophrenia patients+controls, fathers of schizophrenia patients+controls, and sibs of schizophrenia patients+controls for input into the SAS System. Each dataset contained 6 variables. In order, these were:

1. six digit identification (ID) number;
2. response variable, i.e. affection status of the proband (0 =unaffected, i. e. control individual; 1=affected, i. e. schizophrenia patient);
3. DHFR mutation-single dose (Ds);
4. DHFR mutation-double dose (Dd);
5. MTHFR mutation-single dose (Ms); and
6. MTHFR mutation-double dose (Md).

For mutation data, 0=mutation absent, 1=mutation present.

Results

Alleles of the DHFR 19 bp Deletion Polymorphism: Amplification of the region of intron 1 of DHFR defmed by the primers in FIG. 1 gave two polymorphic bands of 232 and 213 bp after separation on a non-denaturing polyacrylamide gel (FIG. 2). Sequencing the PCR products from the two homozygotes showed that they differed by 19 bp (FIG. 3). The upper and lower bands (FIG. 2), non-deletion allele and deletion allele respectively, were designated alleles 1 and 2 respectively. Comparison with two published sequences showed that allele 1 was identical with one of them [Yang et al. *J. Mol. Biol*. 176:169–187 (1984)] indicating that allele 2 resulted from a 19 bp deletion. The other published sequence [Chen et al. *J. Biol. Chem*. 259:3933–3943 (1984)] was lacking one base pair of allele 1, an A indicated by "*" in FIG. 3. It is possible that this shorter reference sequence [Chen et al. *J. Biol. Chem*. 259:3933–3943 (1984)] resulted from a sequencing artifact.

Sequences in the 19 bp Deleted Region of DHFR Intron 1: The 19bp sequence in the deleted region (FIG. 3) of DHFR intron 1 contained sites for several restriction enzymes including Rsal and ScrFI, and potential binding sites for transcription factors including Sp1, NF-kappaB, CP1 (NF-Y), E2F, ETF and GCF in the 19 base pair region.

Binary Logistic Regression Analysis: The number of individuals with each genotype of the two polymorphisms among 38 unrelated schizophrenia probands, 35 unrelated mothers of schizophrenia probands, 15 unrelated fathers of schizophrenia probands, 13 unrelated unaffected sibs of schizophrenia probands, and 211 unrelated unaffected control probands is shown in Table 13.

TABLE 13

DISTRIBUTION OF DHFR AND MTHFR MUTATION GENOTYPES AND ALLELES AMONG CONTROLS, SCHIZOPHRENICS, AND SCHIZOPHRENIA FAMILY MEMBERS

| GenTyp | Schizophrenia | | | | |
|---|---|---|---|---|---|
| | P | M | F | S | Ctrl |
| DHFR 19 bp deletion polymorphism: | | | | | |
| 1/1 | 6 (.16) | 10 (.29) | 4 (.27) | 4 (.31) | 56 (.26) |
| 1/2 | 22 (.58) | 13 (.37) | 11 (.73) | 8 (.61) | 115 (.54) |
| 2/2 | 10 (.26) | 12 (.34) | 0 (0.0) | 1 (.08) | 40 (.19) |
| total | 38 (1.00) | 35 (1.00) | 15 (1.00) | 13 (1.00) | 211 (.99) |
| MTHFR 677C -> T transition polymorphism: | | | | | |
| 1/1 | 14 (.37) | 16 (.46) | 11 (.73) | 4 (.31) | 103 (.49) |
| 1/2 | 18 (.47) | 18 (.51) | 3 (.20) | 8 (.61) | 78 (.37) |
| 2/2 | 6 (.16) | 1 (.03) | 1 (.07) | 1 (.08) | 30 (.14) |
| total | 38 (1.00) | 35 (1.00) | 15 (1.00) | 13 (1.00) | 211 (1.00) |

P = schizophrenia patients; M = mothers of schizophrenia patients; F = fathers of schizophrenia patients; S = unaffected sibs of schizophrenia patients; Ctrl = control individuals.

The four data files were analyzed using the logistic procedure of SAS (SAS Institute Inc., 1995) and the "descending" option, which modeled the probability that RESPONSE=1, that is, the probability that the proband was affected with schizophrenia. Note that the proband was not always the individual whose genotype data were used. For example, genotype data for mothers of schizophrenic probands were used to determine the probability that their children, the probands, were affected. Use of the "best" model selection options for logistic analysis in SAS gave the best models for two and three explanatory variables, (Table 14).

TABLE 14

BINARY LOGISTIC REGRESSION RESULTS

| GENETIC RISK FACTOR Odds Ratio (p value) | MODEL: Ds Dd Ms Md |
|---|---|
| Schizophrenia Patients | |
| Ds OR(p) | 1.937 (.18) |
| Dd OR(p) | 1.263 (.59) |
| Ms OR(p) | 1.775 (.14) |
| Md OR(p) | 0.914 (.86) |
| Mothers of Schizophrenia Patients | |
| Ds OR(p) | 0.630 (.31) |
| Dd OR(p) | 2.653 (.028)* |
| Ms OR(p) | 1.439 (.34) |
| Md OR(p) | 0.143 (.065) |
| Fathers of Schizophrenia Patients | |
| Ds OR(p) | 1.178 (.79) |
| Dd OR(p) | 0.000 (.96) |
| Ms OR(p) | 0.366 (.14) |
| Md OR(p) | 0.841 (.88) |
| Unaffected Sibs of Schizophrenia Patients | |
| Ds OR(p) | 1.104 (.88) |
| Dd OR(p) | 0.337 (.31) |
| Ms OR(p) | 2.688 (.12) |
| Md OR(p) | 0.317 (.29) |

Notes For Table 14
DHFR 19 bp deletion: Ds = single dose; Dd = double dose
MTHFR 677C -> T mutation: Ms = single dose; Md = double dose Logistic regression model:

Model with four explanatory variables (Ms, Md, Ds and Dd).

OR(p)=odds ratio and the corresponding p-value for that odds ratio determination *=significant at the $p<0.05$ level.

0.000 odds ratios occurred since none of the fathers of schizophrenia patients had genotype Dd; there was a possibly quasi- complete separation in the sample points; the maximum likelihood estimate may not exist; and therefore validity of the model fit for these odds ratios was questionable.

The comparison of mothers of schizophrenia probands with control probands was statistically significant. Ds was not a significant genetic risk factor. Neither Ms nor Md in mothers was a significant genetic risk factor. However, the p-value for Md decreased and approached significance ($p=0.065$) at the $p<0.05$ level.

Predicted Probabilities of the Various Genotypes: The "probs predicted" modality of SAS, gave the predicted probability that the proband was affected with schizophrenia (response=1) given genotype data for control probands and schizophrenia patients (probands), mothers of schizophrenia probands, fathers of schizophrenia probands, or sibs of schizophrenia probands. The maximum probabilities obtained are shown in Table 15. The highest maximum predicted probability that the proband was affected was obtained for genotype data from mothers of schizophrenia probands, next for schizophrenia probands, next for fathers of schizophrenia probands, and lowest for sibs of schizophrenia probands.

TABLE 15

| MAXIMUM PREDICTED PROBABILITY | | | | |
|---|---|---|---|---|
| Model | P | M | F | S |
| Ds Dd Ms Md | 0.24 | 0.29 | 0.12 | 0.11 |

Model and explanatory variables are the same as in Table 14.

Determination of Genotypes Conferring the Highest Risk: The predicted probabilities that the proband was affected with schizophrenia given specific genotypes of control probands and schizophrenia probands, mothers of schizophrenia probands, fathers of schizophrenia probands, or sibs of schizophrenia probands were determined using the model containing all four explanatory variables (Table 16). The predicted probabilities that the proband was affected with schizophrenia were highest for maternal genotypes (Table 15). The maternal genotype with the highest risk was Dd Ms, conferring a probability of 0.29 of schizophrenia in the proband (Table 16). The Dd Ms genotype also gave the highest predicted probability, 0.24, for schizophrenia patients.

TABLE 16

PREDICTED PROBABILITIES FOR SPECIFIC GENOTYPES
Model: Ds Dd Ms Md

| Genotype | Predicted Probability | Genotype | Predicted Probability |
|---|---|---|---|
| Schizophrenia Patients: | | | |
| Dnull + Mnull | 0.07 | Ds + Ms | 0.20 |
| Dnull + Ms | 0.12 | Ds + Md | 0.19 |
| Dnull + Md | 0.11 | Dd + Ms | 0.24 |
| Ds + Mnull | 0.12 | Dd + Md | 0.23 |
| Dd + Mnull | 0.15 | | |
| Mothers of Schizophrenia Patients: | | | |
| Dnull + Mnull | 0.16 | Ds + Ms | 0.13 |
| Dnull + Ms | 0.20 | Ds + Md | 0.02 |
| Dnull + Md | 0.03 | Dd + Ms | 0.29 |
| Dd + Mnull | 0.22 | Dd + Md | 0.06 |
| Ds + Mnull | 0.10 | | |
| Fathers of Schizophrenia Patients: | | | |
| Dnull + Mnull | 0.10 | Ds + Ms | 0.05 |
| Dnull + Ms | 0.04 | Ds + Md | 0.04 |
| Dnull + Md | 0.03 | Dd + Ms | 0.0 |
| Ds + Mnull | 0.12 | Dd + Md | 0.0 |
| Dd + Mnull | 0.0 | | |
| Unaffected Sibs of Schizophrenia Patients: | | | |
| Dnull + Mnull | 0.04 | Ds + Ms | 0.11 |
| Dnull + Ms | 0.10 | Ds + Md | 0.04 |
| Dnull + Md | 0.03 | Dd + Ms | 0.04 |
| Ds + Mnull | 0.04 | Dd + Md | 0.01 |
| Dd + Mnull | 0.02 | | |

Genotypes consist of the same explanatory variables described in Table 14 except that Dnull has no copy of the DHFR deletion and Mnull has no copy of the MTHFR 677C -> T variant. Odds ratios of 0.0 were unsatisfactory as described in Table 14.

DISCUSSION

Structure and Function of the DHFR 19 bp Deletion Polymorphism: DHFR polymorphisms have been reported previously [Feder et al., *Nucl. Acids Res.* 15:5906 (1987); Detera-Wadleigh et al., *Nucl. Acids Res.* 17:6432 (1989)]. It is known that introns are important for message regulation e.g., splicing, or as sites for binding transcription factors. Since the first intron is a relatively common location for regulatory elements, it is possible that the deleted region of DHFR intron 1 could play a role in regulation of DHFR or that the deletion could be a genetic risk factor for schizophrenia because it removes potential transcription factor binding sites. Abnormalities of transcription factors and their binding sites may play a role in disease. For example, a polymorphic Spl binding site in the collagen type I alpha 1 gene has been associated with reduced bone density and osteoporosis [Grant et al., *Nature Genet.* 14:203–205 (1996)].

The Nature of the Putative Folate Genetic Risk Factors for Schizophrenia: Dd in the mother of a schizophrenia proband conferred significantly increased risk of schizophrenia in her child (Table 14). The findings that Dd was a genetic risk factor in mothers but not fathers of schizophrenia probands (Table 15) and that Dd in mothers gave a higher predicted probability than in schizophrenia patients, fathers or sibs (Tables 15 and 16) was consistent with the role of DHFR as a teratogenic locus according to the gene-teratogen model (described above). The finding that a double dose but not a single dose of the DHFR deletion in mothers was a genetic risk factor (Table 16) supported a recessive mode of action in the mother. A teratogenic locus acting in the mother can also act as a modifying or specificity locus in the fetus.

Neither Ms nor Md in mothers of schizophrenia probands showed statistical significance as genetic risk factors for schizophrenia in probands (Table 14). However Md in mothers approached statistical significance (p=0.065) and appeared to be protective (odds ratio 0.14), while Ms in mothers appeared to increase risk modestly (odds ratio 1.44, p=0.34).

Role of Genetic and Environmental Factors in Schizophrenia: Since the probability that a schizophrenia co-twin is also affected is reported [Gottesman, *Schizophrenia Genesis*, Schizophrenia Genesis- The Origins of Madness, W. H. Freeman & Co. N.Y.(1991)] to be only 48%, a large part of the risk for schizophrenia would be anticipated to come from environmental factors. Therefore, some controls should have the genetic risk factors for schizophrenia but not be affected with schizophrenia. In the present data set, 6 of 35 schizophrenia mothers and 7 of 38 schizophrenia patients had Dd Ms, the genotype conferring the highest risk, compared with 15 of 211 controls. Since this genotype gave predicted probabilities of schizophrenia in probands of 0.29 and 0.24 respectively, polymorphisms of DHFR and MTHFR could account for a considerable portion of the genetic component of the risk of schizophrenia.

Relation of DHFR to Cytogenetic and Linkage Data for Schizophrenia: As discussed above, the DHFR gene has been located on chromosome 5 at 5q11.2–13.2. A schizophrenia translocation was reported (McGillivray et al. 1990; Bassett, 1992) affecting 5q11.2–5q13.3. Also two-point lod scores of 4.64 and 2.29 were found [Sherrington et al., *Nature*, 336:164–167 (1988)] for the polymorphic markers D5576 and D5539 respectively on chromosome 5, in this region [McGillivray et al., *Am. J. Med. Genet.*, 35:10–13 (1990); Bassett, *Br. J. Psychiatry*, 161:323–334 (1992)]. Two other linkage studies found small positive lod scores in this region [Coon et al., *Biol. Psychiatry*, 34:277–289 (1993); Kendler and Diehl, *Schizophr. Bull.*, 19:261–285 (1993)], but numerous other studies excluded this region under the assumptions and models used [Kendler and Diehl, *Schizophr. Bull.*, 19:261–285 (1993)]. Recently, new studies have found suggestive evidence for a potential susceptibility locus at a different region of 5q, 5q31 [Schwab et al., *Nat.*

*Genet*. 11:325–327 (1997)] and 5q22-31 [Straub et al., *Molec Psychiatr*. 2:148–155 (1997)].

The case-control study presented herein illustrates the usefulness of the DNA polymorphism-Diet-Cofactor-Development and the gene-teratogen models described above. More importantly, the results presented herein, clearly fail to reject the specific models, i.e., that folate gene polymorphisms can play a role in the etiology of schizophrenia.

The present invention is not to be limited in scope by specific embodiments described herein. Indeed, various modifications of the invention in addition to those described herein will become apparent to those skilled in the art from the foregoing description and the accompanying figures. Such modifications are intended to fall within the scope of the appended claims.

Various publications in addition to the immediately foregoing are cited herein, the disclosures of which are incorporated by reference in their entireties.

We claim:

1. An isolated nucleic acid encoding a human dihydiofolate reductase; said nucleic acid comprising a nucleotide sequence having a 19 base-pair deletion spanning nucleoides 540 to 558 of tie nucleotide sequence of SEQ ID NO:41.

2. The isolated nucleic acid of claim 1 that comprises the nucleotide sequence of SEQ ID NO:42.

3. A vector comprising the nucleic acid of claim 1.

4. A cell comprising the vectr or claim 3.

5. A PCR primer comprising 10 nucleotides that can be used to distinguish SEQ ID NO:42 from a nucleotide sequence selected from the group consisting of SEQ ID NO:41 and SEQ ID NO:45.

6. The primer of claim 5 comprising 18 to 50 consecutive nucleotides.

7. The PCR primer of claim 5 that comprises 12 to 100 consecutive nucleotides from a nucleotide sequence selected from the group consisting of SEQ ID NO: 41, the complementary strand of SEQ ID NO: 41, SEQ ID NO:42, the complementary strand of SEQ ID NO: 42, SEQ ID NO:45, and the complementary strand of SEQ ID NO: 45.

8. The PCR primer of claim 7 wherein the 12 to 100 consecutive nucleotides are from nucleotides 350 to 530 of SEQ ID NO:41.

9. The PCR primer of claim 8 having the nucleotide sequence of 5'-CTA AAC TGC ATC GTC GCT GTG-3' (SEQ ID NO:38).

10. The PCR primer of claim 7 wlwherein the 12 to 100 consecutive nucleotides are from nucleotides 550 to 850 of the complementary strand of SEQ ID NO:41.

11. The PCR pimer of claim 10 having the nucleotide sequence of 5'-AAA AGG GGA ATC CAG TCG G-3' (SEQ ID NO:39).

12. A nucleic acid that hybridizes to the nucleotide sequence ACCTGGGCGGGACGCGCCA (SEQ ID NO:40) or a sequence complementary to SEQ ID NO:40; wherein said nucleic acid consists of 12 to 48 nucleotides; and wherein said nucleic acid does not hybridize to SEQ ID NO:42 or a sequence complementary to SEQ ID NO:42, when said hybridizing is performed under identical conditions.

13. A nucleotide probe comprising 1 nucleotides that hybridizes to the nucleotide sequence of SEQ ID NO:42, but not to the nucleotide sequence of SEQ ID NO:41, when said hybridizing is performed under identical conditions.

14. The nucleotide probe of claim 13 that comprises 18 nucleotides.

15. The nucleotide probe of claim 13 that comprises the nucleotide sequence of CCCACGGTCGGGGTGGC-CGACTCCCGGCGA (SEQ ID NO.37).

16. A nucleotide probe comprising 1 nucleotides that hybridizes to the complementary strand of the nucleotide sequence of SEQ ID NO:42, but not to the complementary strand of the nucleotide sequence of SEQ ID NO:41, when said hybridizing is performed under identical conditions.

17. The nucleotide probe of claim 16 that comprises 18 nucleotides.

18. A nucleotide probe comprising 1 nucleotides that hybridizes to the nucleotide sequence of SEQ ID NO:41, but not to the nucleoticle sequence of SEQ ID NO:42; when said hybridizing is performed under identical conditions.

19. The nucleotide probe of claim 18 that comprises 18 nucleotides.

20. The nucleotide probe of claim 18 that comprises the nucleotide sequence of CCCACGGTCGGGGTAC-CTGGGCGGGACGCGCCAGGCCGACTCCCGGCGA (SEQ ID NO:29).

21. A nucleotide probe comprising 1 nucleotides that hybridizes to the complementary strand of the nucleotide sequence of SEQ ID NO:41, but not to the complementary strand of the iiucleotide sequence of SEQ ID NO:42, when said hybridizing is performed under identical conditions.

22. The nucleotide probe of claim 21 that comprises 18 nucleotides.

23. A nucleic acid that hybridizes to the nucleotide sequence ACCTGGGCGGGACGCGCC (SEQ TD NO:46) or the complementary strand of SEQ ID NO:46; wherein said nucleic acid consists of 12 to 48 nucleotides; and wherein said nucleic acid does not hybridize to SEQ ID NO:42 or a sequence complementary to SEQ ID NO:42, when said hybridizing is perfozmed under identical conditions.

* * * * *

UNITED STATES PATENT AND TRADEMARK OFFICE

CERTIFICATE OF CORRECTION

PATENT NO. : 6,210,950 B1
APPLICATION NO. : 09/318448
DATED : April 3, 2001
INVENTOR(S) : William G. Johnson and Edward Scott Strenroos It is certified that error appears in the above-identified patent and that said Letters Patent is hereby corrected as shown below:

In the Claims:

On Column 151, line 60, in Claim 1, please change the word “nucleoides” to read --nucleotides--;

On Column 151, line 61, in Claim 1, please change the word “tie” to read --the--;

On Column 151, line 65, in Claim 4, please change the word “vectr or” to read --vector of--;

On Column 153, line 7, in Claim 10, please change the word “wlwherein” to read --wherein--;

On Column 153, line 21, in Claim 13, please change the word “1” to read --12--;

On Column 153, line 30, in Claim 16, please change the word “1” to read --12--;

On Column 154, line 5, in Claim 18, please change the word “1” to read --12--;

On Column 154, line 7, in Claim 18, please change the word “nucleoticle” to read --nucleotide--;

On Column 154, line 16, in Claim 21, please change the word “1” to read --12--;

On Column 154, line 19, in Claim 21, please change the word “iiucleotide” to read --nucleotide--;

On Column 154, line 24, in Claim 23, please change the word “TD” to read --ID--;

On Column 154, line 29, in Claim 23, please change the word “perfozmed” to read --performed--;

Signed and Sealed this

Twenty-second Day of January, 2008

JON W. DUDAS
*Director of the United States Patent and Trademark Office*